United States Patent
Paruch et al.

(10) Patent No.: US 9,902,733 B2
(45) Date of Patent: Feb. 27, 2018

(54) FUROPYRIDINES AS INHIBITORS OF PROTEIN KINASES

(71) Applicant: MASARYKOVA UNIVERZITA, Brno (CZ)

(72) Inventors: Kamil Paruch, Tisnov (CZ); Michaela Petrujova, Ostrozska Nova Ves (CZ); Vaclav Nemec, Brno-Bohunice (CZ)

(73) Assignee: MASARYKOVA UNIVERZITA, Brno (CH)

( * ) Notice: Subject to any disclaimer, the term of this patent is extended or adjusted under 35 U.S.C. 154(b) by 0 days.

(21) Appl. No.: 15/304,043

(22) PCT Filed: Apr. 29, 2015

(86) PCT No.: PCT/CZ2015/000038
§ 371 (c)(1),
(2) Date: Oct. 13, 2016

(87) PCT Pub. No.: WO2015/165428
PCT Pub. Date: Nov. 5, 2015

(65) Prior Publication Data
US 2017/0037052 A1    Feb. 9, 2017

(30) Foreign Application Priority Data
Apr. 30, 2014    (EP) .................................. 14166547

(51) Int. Cl.
*C07D 491/048*    (2006.01)
(52) U.S. Cl.
CPC ................................ *C07D 491/048* (2013.01)
(58) Field of Classification Search
CPC .................................................. C07D 491/048
See application file for complete search history.

(56) References Cited

FOREIGN PATENT DOCUMENTS

| WO | 9808847 A1 | 3/1998 |
|---|---|---|
| WO | 9940091 A1 | 8/1999 |
| WO | 2011138657 A1 | 11/2011 |

OTHER PUBLICATIONS

Saitoh, J Med Chem, 2009, 52, 6270-6286.*
Yan, PLoS One, 11(8), 1-18, 2016.*
Internernational Search Report and Written Opinion of corresponding PCT application No. PCT/CZ2015/000038, dated Jul. 28, 2015.
Shiotani, S. et al., "Furopyridines. XXII [1]. Elaboration of the C-Substituents alpha to the Heteronitrogen atom of Furo [2,3-b]-, -[3,2-b]-, -[2,3-c]- and -[3,2-c]pyridine", Journal of Heterocyclic Chemistry, Wiley-Blackwell Publishing, Inc., US, vol. 34, May 1, 1997, pp. 901-907.
Campos, Peter J., et al., A Versatile Synthesis of Pyrrololo-, Furo- and Thienopyridines via Photocyclization of 3-Amino-2-alkene Imines in an Acid Medium, Tetrahedrom, Elsevier Science Publishers, Amsterdam, NL, vol. 55, No. 49, Dec. 3, 1999, pp. 14079-14088.
Arcadi, A., et al., "Palladium-Catalyzed Reactio of 2-Hydroxyaryl and Hydroxyheteroaryl Halides with 1-Alkynes: An Improved Route to the Benezoub 3/4 Furan Ring System", Synthesis, Georg Thieme Verlag, Stuttgart, Germany, No. 9, Sep. 1, 986, pp. 749-751.
Macdonald, Dwight, et al., "Substituted 2,2-bisaryl-bicycloheptanies as novel and potent inhibitors of 5-lipoxygenase activating protein", Biorganic & Medicinal Chemistry Letters, Pergamon, Amsterdam, NL, vol. 18, No. 6, Mar. 15, 2008, pp. 2023-2027.
Saitoh, Morihisa et al., "2-{3-[4-{Alkylsulfinyl)phenyl]-1-benzofuran-5-yl}-5-methyl-1,3,4-oxadiazole Derivatives as Novel Inhibitors of Glycogen Synthase Kinase-3β with Good Brain Permeability", Journal of Medicinal Chemistry, vol. 52, No. 20, Oct. 22, 2009, pp. 6270-6286.
Abramenko, P.I., et al., "Synthesis of some methyl-substituted furo(3,2-b) pyridines", All-Union State Scientific-Research and Project Institute of Photo Chemical Industry), vol. 17, No. 6, Jan. 1, 1972, Moscow, Russia, pp. 695-696.

* cited by examiner

*Primary Examiner* — D Margaret M Seaman
(74) *Attorney, Agent, or Firm* — Notaro, Michalos & Zaccaria P.C.

(57) ABSTRACT

The invention relates to furo[3,2-b]pyridines substituted at least in position 5 as inhibitors of protein kinases, regulators or modulators, methods of preparation thereof, pharmaceutical compositions containing the compounds, and pharmaceutical use of the compounds and compositions in the treatment of the diseases such as, for example, cancer or neurodegenerative diseases.

8 Claims, No Drawings

SEQUENCE LISTING

<160> NUMBER OF SEQ ID NOS: 4

<210> SEQ ID NO 1
<211> LENGTH: 26
<212> TYPE: PRT
<213> ORGANISM: Artificial
<220> FEATURE:
<223> OTHER INFORMATION: sequence used in CLK2 assay

<400> SEQUENCE: 1

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 2
<211> LENGTH: 26
<212> TYPE: PRT
<213> ORGANISM: Artificial
<220> FEATURE:
<223> OTHER INFORMATION: sequence used in CLK4 assay

<400> SEQUENCE: 2

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 3
<211> LENGTH: 12
<212> TYPE: PRT
<213> ORGANISM: Artificial

```
<220> FEATURE:
<223> OTHER INFORMATION: sequence used in FLT3 assay

<400> SEQUENCE: 3

Glu Ala Ile Tyr Ala Ala Pro Phe Ala Lys Lys Lys
1               5                   10

<210> SEQ ID NO 4
<211> LENGTH: 14
<212> TYPE: PRT
<213> ORGANISM: Artificial
<220> FEATURE:
<223> OTHER INFORMATION: sequence used in TRKA assay

<400> SEQUENCE: 4

Lys Lys Lys Ser Pro Gly Glu Tyr Val Asn Ile Glu Phe Gly
1               5                   10
```

FUROPYRIDINES AS INHIBITORS OF PROTEIN KINASES

FIELD OF THE INVENTION

The present invention relates to substituted furo[3,2-b]pyridines as inhibitors of various protein kinases, regulators or modulators, pharmaceutical compositions containing the compounds, and pharmaceutical use of the compounds and compositions in the treatment of the diseases such as, for example, cancer, inflammation, pain, neurodegenerative diseases or viral infections.

BACKGROUND ART

Protein kinases are involved in regulation of practically all processes that are central to the growth, development, and homeostasis of eukaryotic cells. In addition, some protein kinases have an important role in oncogenesis and tumor progression and several kinase inhibitors are now approved for the treatment of cancer (D. J. Matthews and M. E. Gerritsen: *Targeting protein kinases for cancer therapy*, Wiley, 2010).

Examples of kinase inhibitors that are used in modern oncology include: imatinib (treatment of CML); dasatinib (CML with resistance to prior treatment, including imatinib); nilotinib (CML); bosutinib (CML); gefitinib (non-small cell lung cancer); erlotinib (non-small cell lung cancer and pancreatic cancer); lapatinib (breast cancer); sorafenib (metastatic renal cell carcinoma, hepatocellular cancer); vandetanib (metastatic medullary thyroid cancer); vemurafenib (inoperable or metastatic melanoma); crizotinib (non-small cell lung cancer); sunitinib (metastatic renal cell carcinoma, gastrointestinal stromal tumor that is not responding to imatinib, or pancreatic neuroendocrine tumors); pazopanib (renal cell carcinoma and advanced soft tissue sarcoma); regorafenib (metastatic colorectal cancer); cabozantinib (metastatic medullary thyroid cancer); dabrafenib (BRAF V600E mutation-positive advanced melanoma); and trametinib (in combination with dabrafenib for the treatment of BRAF V600E/K-mutant metastatic melanoma).

Various kinases are regarded as good targets for pharmacological inhibition in order to treat proliferative and/or neurodegenerative diseases. Biological and potential therapeutic significance of some selected kinases is briefly summarized below.

The regulation of splice site usage provides a versatile mechanism for controlling gene expression and for the generation of proteome diversity, playing an essential role in many biological processes. The importance of alternative splicing is further illustrated by the increasing number of human diseases that have been attributed to mis-splicing events. Appropriate spatial and temporal generation of splicing variants demands that alternative splicing be subjected to extensive regulation, similar to transcriptional control. The CLK (Cdc2-like kinase) family has been implicated in splicing control (*Experimental Cell Research* 1998, 241, 300.). Pharmacological inhibition of CLK1/Sty results in blockage of SF2/ASF-dependent splicing of beta-globin pre-mRNA in vitro by suppression of CLK-mediated phosphorylation. It also suppresses dissociation of nuclear speckles as well as CLK1/Sty-dependent alternative splicing in mammalian cells and was shown to rescue the embryonic defects induced by excessive CLK activity in *Xenopus* (*Journal of Biological Chemistry* 2004, 279, 24246.).

Alternative mRNA splicing is a mechanism to regulate protein isoform expression and is regulated by alternative splicing factors. The alternative splicing factor 45 (SPF45) is overexpressed in cancer and its overexpression enhances two processes that are important for metastasis, i.e. cell migration and invasion, dependent on biochemical regulation by CLK1 (*Nucleic Acids Research* 2013, 41, 4949.). CLK1 phosphorylates SPF45 on eight serine residues. CLK1 expression enhances, whereas CLK1 inhibition reduces, SPF45-induced exon 6 exclusion from Fas mRNA. Inhibition of CLK1 increases SPF45 degradation through a proteasome-dependent pathway. In addition, small-molecule inhibitors of specific CLKs can suppress HIV-1 gene expression and replication (*Retrovirology* 2011, 8, 47.), which could be used in concert with current drug combinations to achieve more efficient treatment of the infection. Inhibition of CLK1 can be applicable in the treatment of Alzmeimer's disease (*Current Drug Targets* 2014, 15, 539.).

DYRK (dual specificity tyrosine phosphorylation-regulated kinase) family enzymes are essential components of important signaling cascades in the pathophysiology of cancer and Alzheimer's disease and their biological expression levels regulate key signaling processes in these diseases. In particular, DYRK2 is over-expressed in adenocarcinomas of the esophagus and lung (*Cancer Research* 2003, 63, 4136.) and DYRK1A in glioblastoma where its inhibition compromised tumors' survival and produced a profound decrease in tumor burden (*Journal of Clinical Investigation* 2013, 123, 2475.). DYRK1B activation that is induced by microtubule damage triggers microtubule stabilization and promotes the mitochondrial translocation of p21Cip1/waf1 to suppress apoptosis. Its inhibition caused reduced viability of cancer cells (*ACS Chemical Biology* 2014, 9, 731.). Correspondingly, it has been understood that inhibition of DYRK kinases alone or in combination with other chemotherapeutic drugs may have tumor suppression effect and the enzymes are therefore appropriate targets for pharmacological inhibition (*Bioorgank & Medicinal Chemistry Letters* 2013, 23, 6610; *Medicinal Chemistry Research* 2014, 23, 1925.).

In addition, DYRK kinases are also over-expressed in neurodegenerative diseases such as Alzheimer's disease, Parkinson's disease, Huntington's disease, and Pick disease (*Neurobiology of Disease* 2005, 20, 392; *Cellular and Molecular Life Sciences* 2009, 66, 3235.).

HIPK2 (homeodomain-interacting protein kinase) is a tumor suppressor and functions as an evolutionary conserved regulator of signaling and gene expression. This kinase regulates a vast array of biological processes that range from the DNA damage response and apoptosis to hypoxia signaling and cell proliferation. Recent studies showed the tight control of HIPK2 by hierarchically occurring posttranslational modifications such as phosphorylation, small ubiquitin-like modifier modification, acetylation, and ubiquitination. Dysregulation of HIPK2 can result in increased proliferation of cell populations as it occurs in cancer or fibrosis. Inappropriate expression, modification, or localization of HIPK2 can be a driver for these proliferative diseases (*Journal of Molecular Medicine* 2013, 91, 1051.).

FMS-like tyrosine kinase 3 (FLT3), a receptor tyrosine kinase (RTK), is a membrane-bound receptor with an intrinsic tyrosine kinase domain. Its activation regulates a number of cellular processes (e.g. phospholipid metabolism, transcription, proliferation, and apoptosis), and through these processes, FLT3 activation plays a critical role in governing normal hematopoiesis and cellular growth Expression of FLT3 has been evaluated in hematologic malignancies. The majority of B-cell acute lymphocytic leukemia (ALL) and acute myeloid leukemia (AML) blasts (>90%) express FLT3 at various levels (*Clinical Cancer Research* 2009, 15, 4263.). Overexpression or/and activating mutation of FLT3 kinase play a major driving role in the pathogenesis of acute myeloid leukemia (AML). Hence, pharmacologic inhibitors of FLT3 are of therapeutic potential for AML treatment (*Oncologist* 2011, 16, 1162; *PLoS One* 2014, 9, e83160/1; *Leukemia Lymphoma* 2014, 55, 243.).

Tropomyosin-related kinase (TRK) is a family of three RTKs (TRK-A, TRK-B, TRK-C) regulating several signaling pathways that are important for survival and differentiation of neurons. TRK-A regulates proliferation and is important for development and maturation of the nervous system, promotes survival of cells from death. Point mutations, deletions and chromosomal rearrangements cause ligand-independent receptor dimerization and activation of TRK-A. In mutated version of TRK, abnormal function will render cells unable to undergo differentiation in response to ligand in their microenvironment, so they would continue to grow when they should differentiate, and survive when they should die. Activated TRK-A oncogenes have been associated with several human malignancies, e.g., breast, colon, prostate, thyroid carcinomas and AML (*Cell Cycle* 2005, 4, 8; *Cancer Letters* 2006, 232, 90.). In addition, inhibition of TRK can be relevant for the treatment of inflammation (*PLoS One* 2013, 8, e83380.) and pain (*Expert Opinion on Therapeutic Patients* 2009, 19, 305.).

In summary, there is a need for inhibitors of different protein kinases in order to treat or prevent disease states associated with abnormal regulation of the kinases-mediated biological processes.

DISCLOSURE OF THE INVENTION

The present invention provides substituted furo[3,2-b]pyridine compounds, methods of preparing such compounds, pharmaceutical compositions comprising one or more of such compounds, and their use in the treatment, prevention, inhibition or amelioration of one or more diseases associated with protein kinases using such compounds or pharmaceutical compositions.

The present invention provides compounds represented by the structural formula (I):

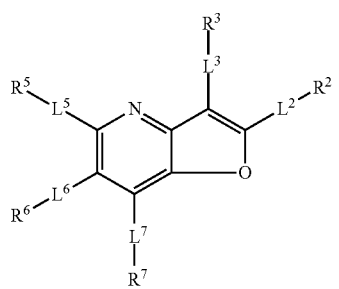

(I)

or a pharmaceutically acceptable salt, solvate or a prodrug thereof, wherein:

$L^5$ is selected from the group consisting of a bond, —N($R^{11}$)—;

$L^2$ is selected from the group consisting of a bond, —O—;

$L^3$ is selected from the group consisting of a bond, —N($R^{11}$)—, —O—;

$L^6$ is selected from the group consisting of a bond, —O—;

$L^7$ is selected from the group consisting of a bond, —N($R^{11}$)—;

$R^5$ is selected from the group consisting of $C_1$-$C_6$ alkyl; aryl; heteroaryl; biaryl; bi(heteroaryl); cycloalkylaryl; heterocyclylaryl; heteroarylaryl; arylheteroaryl; cycloalkylheteroaryl; heterocyclylheteroaryl; wherein each of the substituent moieties can be unsubstituted or optionally substituted;

$R^2$ is selected from the group consisting of H; —$CF_3$; $NH_2$; —Cl; —Br; —F; $C_1$-$C_6$ alkyl;

$R^3$ is selected from the group consisting of H; $C_1$-$C_6$ alkyl; aryl; cycloalkyl; heteroaryl; biaryl; heteroarylaryl; arylheteroaryl; wherein each of the substituent moieties can be unsubstituted or optionally substituted;

$R^6$ is selected from the group consisting of H; —$CF_3$; $NH_2$; —Cl; —Br; —F; $C_1$-$C_6$ alkyl; aryl; heteroaryl; wherein each of the substituent moieties can be unsubstituted or optionally substituted;

$R^7$ is selected from the group consisting of H; $C_1$-$C_6$ alkyl; aryl; cycloalkyl; heteroaryl; biaryl; heteroarylaryl; arylheteroaryl; wherein each of the substituent moieties can be unsubstituted or optionally substituted;

$R^{11}$ is selected from the group consisting of H, $C_1$-$C_6$ alkyl;

provided that the substituent in position 5 (L5-R5) is not oxadiazolyl or methyl-oxadiazolyl.

As used in this disclosure, the following terms, unless otherwise indicated, have the following meanings:

"alkyl" means an aliphatic hydrocarbon group which may be straight or branched and contains 1 to 6 carbon atoms, more preferably 1 to 4 carbon atoms in the chain. Examples of suitable alkyls are methyl, ethyl, propyl, isopropyl, butyl, isobutyl, tert-butyl, pentyl, isopentyl, hexyl. The alkyl can be unsubstituted or optionally substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N(H, C_1$-$C_4$ alkyl$)_2$, CHO, COO(H, $C_1$-$C_4$ alkyl), COH, C(O)N(H, $C_1$-$C_4$ alkyl), O($CH_2$)$_p$N($CH_3$)$_2$ and $NR^9R^{10}$;

"aryl" means an aromatic monocyclic or polycyclic ring system containing 6 to 14 carbon atoms, preferably 6 to 10 carbon atoms. Examples of suitable aryls are phenyl, naphthyl. The aryl can be unsubstituted or optionally substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N(H, C_1$-$C_4$ alkyl$)_2$, CHO, COO(H, $C_1$-$C_4$ alkyl), COH, C(O)N(H, $C_1$-$C_4$ alkyl), $NR^9R^{10}$, —$(CR^9R^{10})_pR^{9a}$, O($CH_2$)$_p$N($CH_3$)$_2$ and —$(CR^9R^{10})_pOR^{9a}$;

"cycloalkyl" means an aliphatic monocyclic or bicyclic ring system comprising 3 to 10 carbon atoms, preferably 5 to 7 carbon atoms. Suitable examples include cyclopentyl, cyclohexyl, cycloheptyl, 1-decalinyl, norbornyl, adamantyl. The cycloalkyl can be unsubstituted or optionally substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N(H, C_1$-$C_4$ alkyl$)_2$, CHO, COO(H, $C_1$-$C_4$ alkyl), COH, C(O)N(H, $C_1$-$C_4$ alkyl), $NR^9R^{10}$), —$(CR^9R^{10})_pR^{9a}$, O($CH_2$)$_p$N($CH_3$)$_2$ and —$(CR^9R^{10})_pOR^{9a}$;

"heterocyclyl" means an aliphatic monocyclic or bicyclic ring system containing 3 to 10 carbon atoms, preferably 4 to 8 carbon atoms, and at least one heteroatom selected from the group consisting of nitrogen, oxygen and sulfur. Suitable examples include piperazinyl and morpholinyl. Preferably, heterocyclyl is not a bicyclic ring system containing only N heteroatoms. The heterocyclyl can be unsubstituted or optionally substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N(H, C_1$-$C_4$ alkyl)$_2$, CHO, COO(H, $C_1$-$C_4$ alkyl), COH, C(O)N(H, $C_1$-$C_4$ alkyl), $NR^9R^{10}$), —$(CR^9R^{10})_pR^{9a}$, $O(CH_2)_pN(CH_3)_2$ and —$(CR^9R^{10})_pOR^{9a}$;

"heteroaryl" means an aromatic monocyclic or bicyclic ring system containing 1 to 14 carbon atoms, preferably 3 to 7 carbon atoms, most preferably 3 to 5 carbon atoms, and at least one heteroatom selected from the group consisting of nitrogen, oxygen and sulfur. Examples of suitable heteroaryls are pyrazolyl, pyridyl, pyrimidinyl, pyrazinyl, furanyl, thienyl, oxazolyl, thiazolyl, isothiazolyl, isoxazolyl, pyrrolyl, imidazolyl. Preferably, heteroaryl is not indolyl, indolinolyl or imidazopyridazinyl. The heteroaryl can be unsubstituted or optionally substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N(H, C_1$-$C_4$ alkyl)$_2$, CHO, COO(H, $C_1$-$C_4$ alkyl), COH, C(O)N(H, $C_1$-$C_4$ alkyl), $NR^9R^{10}$, —$(CR^9R^{10})_pR^{9a}$, $O(CH_2)_pN(CH_3)_2$ and —$(CR^9R^{10})_pOR^{9a}$;

"biaryl" means an aryl-aryl- group in which each of the aryls is independently as previously described. An example is biphenyl;

"bi(heteroaryl)" means an heteroaryl-heteroaryl- group in which each of the heteroaryls is independently as previously described;

"cycloalkylaryl" means a cycloalkyl-aryl- group in which the cycloalkyl and aryl are as previously described;

"heterocyclylaryl" means a heterocyclyl-aryl- group in which the heterocyclyl and aryl are as previously described;

"heteroarylaryl" means a heteroaryl-aryl- group in which the heteroaryl and aryl are as previously described;

"arylheteroaryl" means a aryl-heteroaryl- group in which the aryl and heteroaryl are as previously described;

"cycloalkylheteroaryl" means a cycloalkyl-heteroaryl- group in which the heteroaryl and cycloalkyl are as previously described;

"heterocyclylheteroaryl" means a heterocyclyl-heteroaryl- group in which the heterocyclyl and heteroaryl are as previously described;

wherein each of aryl, cycloalkyl, heterocyclyl, heteroaryl, biaryl, bi(heteroaryl), cycloalkylaryl, heterocyclylaryl, heteroarylaryl, arylheteroaryl, cycloalkylheteroaryl, and heterocyclylheteroaryl can be bound directly or via a methylene or ethylene spacer;

p is an integer in the range of from 1 to 7, more preferably from 1 to 5, even more preferably 1 to 3;

$R^9$ is H or C1-C6 alkyl, unsubstituted or optionally substituted by —OH, —$NH_2$, —$N(CH_3)_2$;

$R^{9a}$ is H or C1-C6 alkyl, unsubstituted or optionally substituted by —OH, —$NH_2$, —$N(CH_3)_2$;

$R^{10}$ is H or C1-C6 alkyl, unsubstituted or optionally substituted by —OH, —$NH_2$, —$N(CH_3)_2$.

In a preferred embodiment, $R^5$ is selected from the group consisting of aryl; heteroaryl; heterocyclylaryl; heteroarylaryl; arylheteroaryl; heterocyclylheteroaryl; wherein each of the substituent moieties can be unsubstituted or optionally substituted, preferably by at least one substituent selected from the group consisting of F, Cl, Br, methyl, ethyl, propyl, isopropyl, butyl, isobutyl, tert-butyl, methoxy, ethoxy, propoxy, isopropoxy, OH, $NH_2$, $N(CH_3)_2$, $O(CH_2)_p N(CH_3)_2$. More preferably, $R^5$ is selected from the group consisting of aryl; heteroaryl; wherein each of the substituent moieties can be unsubstituted or optionally substituted, preferably by at least one substituent selected from the group consisting of F, Cl, Br, methyl, ethyl, propyl, isopropyl, butyl, isobutyl, tert-butyl, methoxy, ethoxy, propoxy, iso-propoxy, OH, $NH_2$, $N(CH_3)_2$, $O(CH_2)_pN(CH_3)_2$. Even more preferably, the heteroaryl in $R^5$ is pyrazolyl.

In a preferred embodiment, any of $L^5$, $L^7$ is independently selected from the group consisting of a bond, —NH—.

In another preferred embodiment, any of $L^2$, $L^6$ is a bond.

In yet another preferred embodiment, $L^3$ is a bond or —O—.

In a preferred embodiment, $R^3$ is selected from the group consisting of aryl; heteroaryl; biaryl; wherein each of the substituent moieties can be unsubstituted or optionally substituted, preferably by at least one substituent selected from the group consisting of F, Cl, Br, methyl, ethyl, propyl, isopropyl, butyl, isobutyl, tert-butyl, methoxy, ethoxy, propoxy, isopropoxy, OH, $NH_2$, $N(CH_3)_2$, $O(CH_2)_p N(CH_3)_2$. Even more preferably, the aryl in $R^3$ is phenyl, naphthyl (e.g., 2-naphthyl) and the biaryl in $R^3$ is biphenyl (e.g., 3-biphenyl).

In a preferred embodiment, $R^6$ is selected from the group consisting of H; —Cl; —Br; —F; —OH; —$NH_2$; or methyl.

In a preferred embodiment, $R^2$ is selected from the group consisting of H; —Cl; —Br; —F; OH; —$NH_2$; or methyl.

In a preferred embodiment, $R^7$ is selected from the group consisting of H; $C_1$-$C_6$ alkyl; aryl; heteroaryl; wherein each of the substituent moieties can be unsubstituted or optionally substituted, preferably by at least one substituent selected from the group consisting of F, Cl, Br, methyl, ethyl, propyl, isopropyl, butyl, isobutyl, tert-butyl, methoxy, ethoxy, propoxy, isopropoxy, OH, $NH_2$, $N(CH_3)_2$, $O(CH_2)_p N(CH_3)_2$.

Preferably, at least one of $R^3$ and $R^7$ is not H when the corresponding L (i.e., $L^3$ or $L^7$, respectively) is a bond.

In a preferred embodiment, -$L^2$-$R^2$, -$L^6$-$R^6$, -$L^7$-$R^7$ are hydrogens and -$L^3$, —$R^3$ is not hydrogen.

In one preferred embodiment, -$L^2$-$R^2$, -$L^6$-$R^6$, -$L^7$-$R^7$ are hydrogens, -$L^3$-$R^3$ is aryl or biaryl (optionally substituted) and -$L^5$-$R^5$ is heteroaryl (optionally substituted).

In a preferred embodiment, any of aryl; cycloalkyl; heterocyclyl; heteroaryl; biaryl; bi(heteroaryl); cycloalkylaryl; heterocyclylaryl; heteroarylaryl; arylheteroaryl; cycloalkylheteroaryl; heterocyclylheteroaryl is unsubstituted or substituted with at least one substituent selected from the group consisting of $NH_2$, $N(CH_3)_2$, OH, methoxy, ethoxy, propoxy, isopropoxy, methyl, ethyl, propyl, isopropyl, butyl, isobutyl and tert-butyl.

In another preferred embodiment, any of -$L^2$-$R^2$, -$L^3$-$R^3$, -$L^6$-$R^6$, -$L^7$-$R^7$, -$L^5$-$R^5$ can be hydroxy($C_1$-$C_6$)alkylamino, amino($C_1$-$C_6$)alkylamino or dimethylamino($C_1$-$C_6$)alkylamino.

Pharmaceutically acceptable salts are salts with acids or bases, or acid addition salts. The acids and bases can be inorganic or organic acids and bases commonly used in the art of formulation, such as hydrochloride, hydrobromide, sulfate, bisulfate, phosphate, hydrogen phosphate, acetate, benzoate, succinate, fumarate, maleate, lactate, citrate, tartarate, gluconate, methanesulfonate, benzenesulfonate, para-toluenesulfonate, primary, secondary and tertiary amides, ammonia.

In general, the compounds described in this invention can be prepared through the general routes described below in Schemes 1-6.

Pd-catalyzed coupling of 6-chloro-2-iodopyridin-3-ol with vinyl boronates provides intermediate 1 (as shown in Scheme 1), whose copper-mediated closure provides the furopyridine system in intermediate 2. Subsequent Pd-catalyzed coupling of intermediate 2 with proper C-nucleophiles leads to compounds 3 with $R^5$ substituent attached via C—C bond.

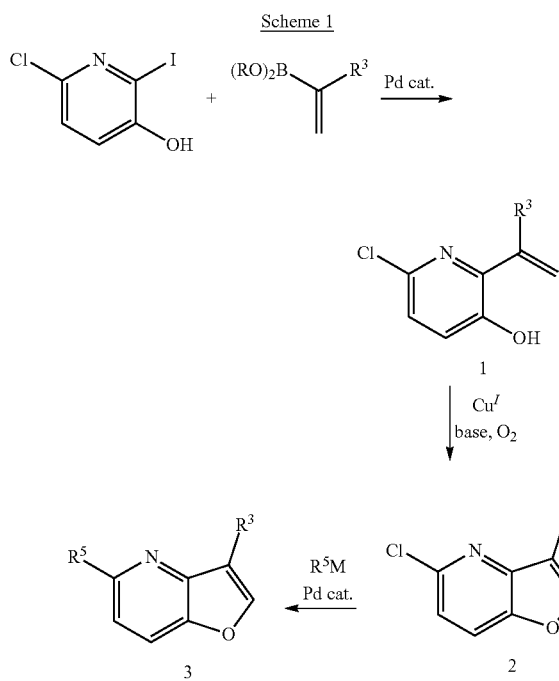

M = e.g., $B(OR)_2$, $BF_3K$, $Sn(R)_3$, MgX, ZnX

Alternatively, intermediate 2 can be subjected to amination to yield amine-containing compounds 4 depicted in Scheme 2.

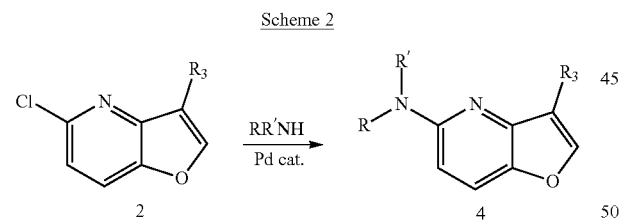

Also, 5-chlorofuro[3,2-b]pyridine can be converted into iodide 5, which can be brominated to yield intermediate 6 (Scheme 3). Sequential chemoselective Pd-catalyzed couplings provide target compounds 3 where $R^5$ and $R^3$ are different aryls or heteroaryls (Scheme 3).

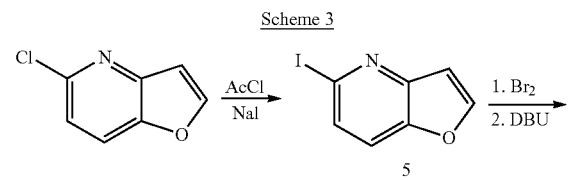

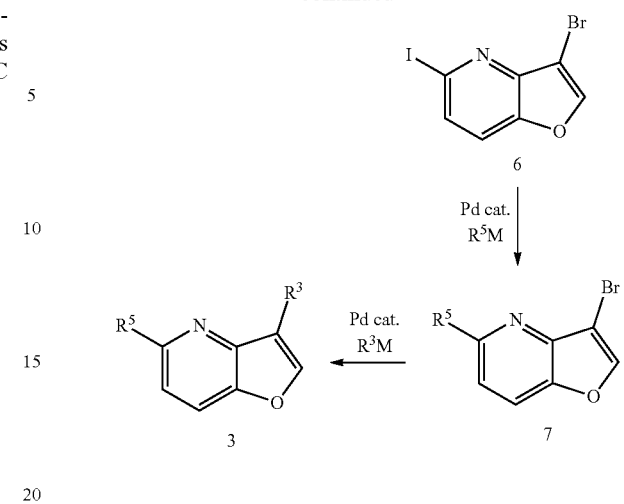

Reaction of 6-chloro-2-iodopyridin-3-ol with trimethylsilylacetylene gives the furopyridine intermediate 8, which can be subjected to a Pd-catalyzed coupling (e.g. Suzuki reaction) and subsequent N-oxidation followed by the treatment with $POCl_3$ to yield chlorinated intermediate 10, as illustrated in Scheme 4.

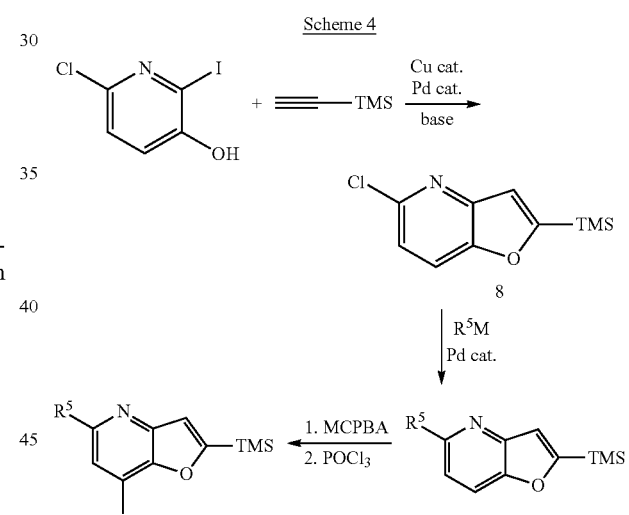

The TMS group in 10 can be removed by KF in methanol to yield intermediate 11, which can be subjected to Pd-catalyzed C—C bond formation or amination (indicated in Scheme 5) to yield compounds 12 and 13, respectively.

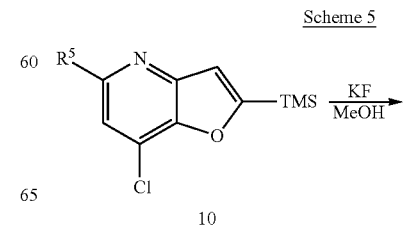

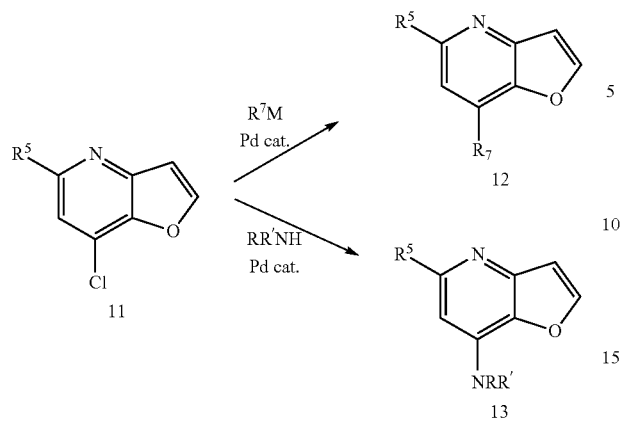

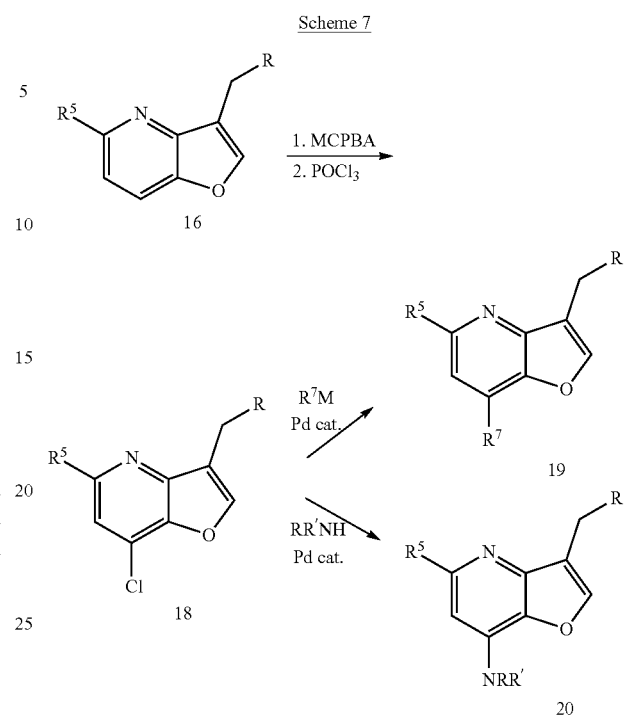

As depicted in Scheme 6, 6-chloro-2-iodopyridin-3-ol can be allylated to give intermediate 14, which can be cyclized to furopyridine intermediate 15, which upon Pd-catalyzed C—C bond formation or amination yields compounds 16 and 17, respectively.

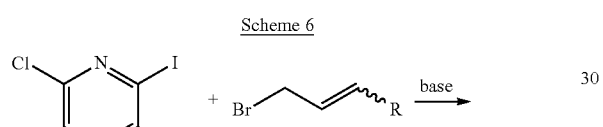

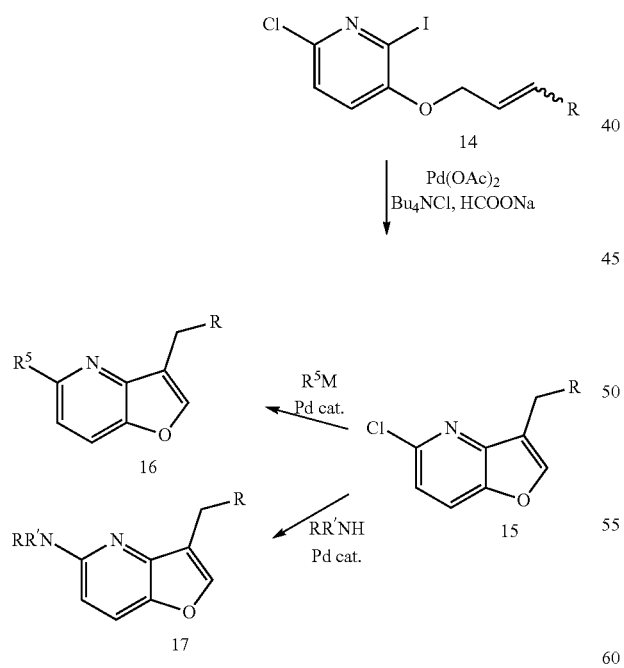

Compounds 16 can be further elaborated (shown in Scheme 7) by N-oxidation-chlorination sequence to yield chlorinated intermediate 18, which can be subjected to Pd-catalyzed C—C bond formation or amination to yield compounds 19 and 20, respectively.

In addition, iodination of 5-bromopyridin-3-ol provides intermediate 21, which can be converted into compound 22. Subsequent Pd-catalyzed coupling followed by N-oxidation and regioselective chlorination yield chloride 24 (Scheme 8).

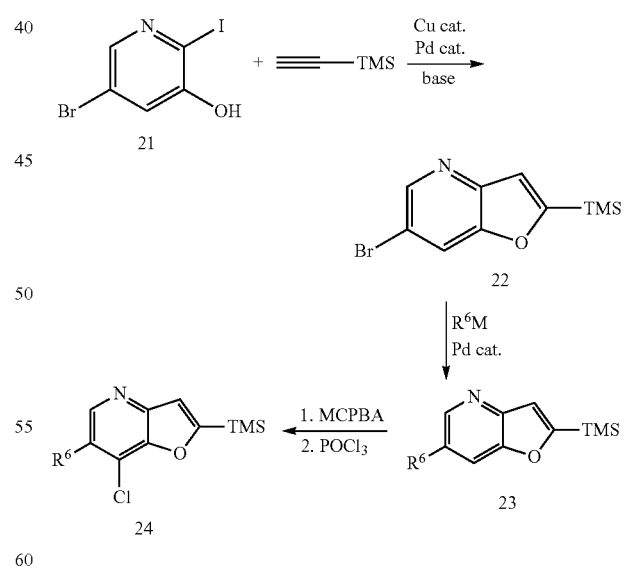

Another Pd-catalyzed coupling on intermediate 24, followed by the by N-oxidation-chlorination sequence and another Pd-catalyzed coupling provide intermediate 26. Removal of the TMS group, followed by final Pd-catalyzed coupling provide target compounds 27 with substituents at positions 7- and 5, respectively (Scheme 9).

Scheme 9

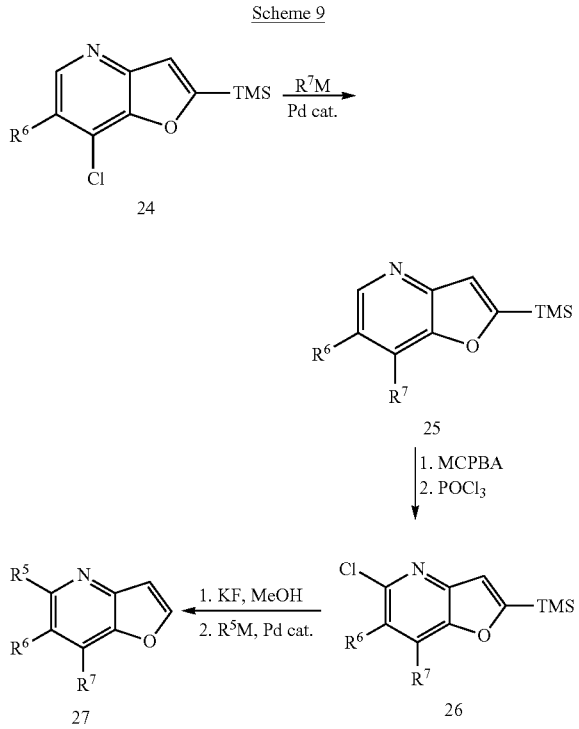

The compounds of formula (I) can be useful as protein kinase inhibitors and can be useful in the treatment and prevention of proliferative diseases, e.g. cancer, inflammation and arthritis, neurodegenerative diseases such as Alzheimer's disease, cardiovascular diseases, viral diseases, and fungal diseases. In one preferred embodiment, the protein kinase is not GSK3. In another preferred embodiment, the protein kinase is selected from CLK2, CLK4, HIPK1, HIPK2, HIPK3, FLT3, TRKA and DYRK2.

The present invention thus provides the compounds of formula (I) for use as medicaments. More specifically, it provides the compounds of formula (I) for use in the treatment and prevention of conditions selected from proliferative diseases, neurodegenerative diseases, cardiovascular diseases, pain, viral diseases, and fungal diseases.

The present invention also provides a method for treatment, inhibition, amelioration or prevention of a condition selected from proliferative diseases, neurodegenerative diseases, cardiovascular diseases, pain, viral diseases, and fungal diseases, in a patient suffering from such condition, comprising the step of administering at least one compound of formula (I) to said patient.

The present invention further includes pharmaceutical compositions comprising at least one compound of formula (I) and at least one pharmaceutically acceptable auxiliary compound. The auxiliary compounds may include, e.g., carriers, diluents, fillers, preservatives, stabilisers, binders, wetting agents, emulsifiers, buffers, etc. Suitable auxiliary compounds are well known to those skilled in the art of formulation. The pharmaceutical compositions are prepared by known methods, e.g., mixing, dissolving etc.

EXAMPLES OF CARRYING OUT THE INVENTION

Preparative Example 1

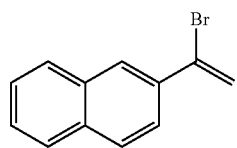

To a solution of $(PhO)_3P$ (2.09 g; 6.75 mmol) in anhydrous $CH_2Cl_2$ (10 mL) was added $Br_2$ (0.380 mL; 7.38 mmol) dropwise under Ar atmosphere at −60° C. Then triethylamine (1.10 mL; 7.89 mmol) and a solution of 2-acetonaphthone (1.03 g; 6.05 mmol) in anhydrous $CH_2Cl_2$ (5 mL) were added. The resulting reaction mixture was stirred under Ar for 18 h, while warming to 25° C., and then heated to reflux for additional 2 h. Then, the $CH_2Cl_2$ and excess of triethylamine and $Br_2$ were evaporated and the residue was purified by column chromatography on silica gel (eluent:hexane/$CH_2Cl_2$—2:1). The product was obtained as a pale orange solid (0.947 g; 67%).

$^1$H NMR (500 MHz, $CDCl_3$) δ 8.07 (d, J=1.55 Hz, 1H); 7.87-7.77 (m, 3H); 7.69-7.66 (m, 1H); 7.52-7.46 (m, 2H); 6.25 (d, J=2.10 Hz, 1H); 5.87 (d, J=2.10 Hz, 1H).

$^{13}$C NMR (126 MHz, $CDCl_3$) δ 135.9, 133.7, 133.2, 131.3, 128.8, 128.1, 127.8, 127.1, 126.9, 124.4, 118.2.

HRMS (APCI): calcd. for $C_{12}H_{10}Br$ $[M+H]^+$=232.9960; found $[M+H]^+$=232.9958.

Preparative Example 2A

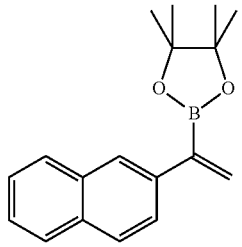 [SMILES: C=C(B1OC(C)(C)C(C)(C)O1)c1ccc2ccccc2c1]

A mixture of vinyl bromide from Preparative Example 1 (0.947 g; 4.06 mmol), bis(pinacolato)diboron (1.140 g; 4.49 mmol), $PPh_3$ (0.066 g; 0.25 mmol), potassium phenolate (0.809 g; 6.12 mmol) and $PdCl_2(PPh_3)_2$ (0.089 g; 0.13 mmol) in anhydrous toluene (20 mL) was stirred under $N_2$ at 50° C. for 24 h. The crude mixture was then cooled to 25° C., poured into water (100 mL) and extracted with EtOAc (3×80 mL). The organic extracts were washed with brine (80 mL), dried over $Na_2SO_4$, filtered, and the solvent was evaporated. The obtained oil was purified by column chromatography on silica gel (eluent:hexane/$CH_2Cl_2$—2:1) to yield the product as a pale orange solid (0.460 g; 40%).

$^1$H NMR (500 MHz, $CDCl_3$) δ 7.94 (s, 1H); 7.84-7.75 (m, 3H); 7.61 (dd, J=1.50 Hz, 8.54 Hz, 1H); 7.46-7.38 (m, 2H); 6.20 (d, J=2.29 Hz, 1H); 6.14 (d, 2.73 Hz, 1H); 1.35 (s, 12H).

$^{13}$C NMR (126 MHz, $CDCl_3$) δ 139.1, 133.8, 132.9, 131.4, 128.5, 127.8, 127.7, 126.4, 126.0, 125.8, 84.1, 25.1.

HRMS (APCI): calcd. for $C_{18}H_{22}BO_2$ $[M+H]^+$=281.1711; found $[M+H]^+$=281.1708.

Preparative Example 2B

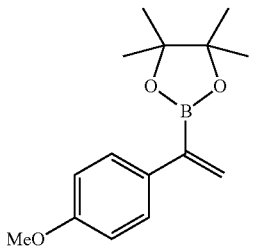 [SMILES: C=C(B1OC(C)(C)C(C)(C)O1)c1ccc(OC)cc1]

A heatgun-dried round bottom flask containing Ni(dppp)Cl$_2$ (0.251 g; 0.46 mmol) was flushed with N$_2$, anhydrous THF (24 mL) was added, followed by dropwise addition of DIBAL-H (1.0M solution in heptane; 20 mL; 20 mmol) at 25° C. The mixture was cooled to 0° C. and 4-ethynylanisole (2.0 mL; 15.4 mmol) was added slowly over 5 min. The resulting black solution was allowed to warm to 25° C. and stirred for additional 2 h. Then, 2-methoxy-4,4,5,5-tetramethyl-1,3,2-dioxaborolane (7.6 mL; 46.4 mmol) was added dropwise at 0° C. and the resulting reaction mixture was stirred under N$_2$ at 80° C. for 15 h. The reaction was then quenched by dropwise addition of water (50 mL) at 0° C., allowed to warm to 25° C. and stirred for additional 1 h. The mixture was poured into saturated aqueous solution of potassium sodium tartarate (200 mL) and extracted with Et$_2$O (3×150 mL). The extracts were washed with brine (200 mL), dried over MgSO$_4$, filtered and the solvent was evaporated. The resulting oil was purified by column chromatography on silica gel (eluent:hexane/EtOAc—10:1) to yield the product as a pale yellow solid (3.22 g; 80%).

$^1$NMR (500 MHz, CDCl$_3$) δ 7.45-7.41 (m, 2H); 6.87-6.82 (m, 2H); 5.99 (d, J=2.65 Hz, 1H); 5.94 (d, J=2.82 Hz, 1H); 3.79 (s, 3H); 1.31 (s, 12H).

$^{13}$C NMR (126 MHz, CDCl$_3$) δ 159.1, 134.2, 129.2, 128.5, 113.9, 84.0, 77.5, 77.2, 77.0, 55.5, 25.0.

HRMS (APCI): calcd. for C$_{15}$H$_{22}$BO$_3$ [M+H]$^+$= 260.1693; found [M+H]$^+$=260.1696.

Preparative Example 2C

By essentially same procedure set forth in Preparative Example 2B, using 1-(tert-butyl)-4-ethynylbenzene, the compound given below was prepared.

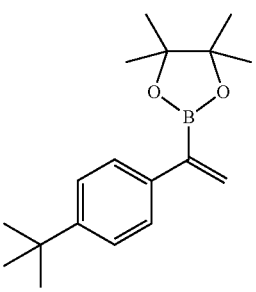 [SMILES: C=C(B1OC(C)(C)C(C)(C)O1)c1ccc(C(C)(C)C)cc1]

White solid.

$^1$H NMR (500 MHz, CDCl$_3$) δ 7.44 (d, J=8.5 Hz, 2H), 7.35 (d, J=8.5 Hz, 2H), 6.08 (d, J=2.8 Hz, 1H), 6.02 (d, J=3.0 Hz, 1H), 1.36-1.30 (m, 21H).

$^{13}$C NMR (126 MHz, CDCl$_3$) δ 150.0, 138.5, 130.2, 126.9, 125.2, 83.8, 34.6, 31.5, 25.0.

HRMS (APCI): calcd. for C$_{18}$H$_{27}$BO$_2$ [M+H]$^+$= 286.2213; found [M+H]$^+$=286.2213.

Preparative Example 3

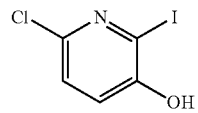

To a stirred solution of 2-chloro-5-hydroxypyridine (6.0 g, 46.3 mmol) in H$_2$O (80 mL) were added Na$_2$CO$_3$ (10.3 g, 97.3 mmol) and I$_2$ (11.8 g, 46.3 mmol). The resulting mixture was stirred at 25° C. under N$_2$ for 2 h. Then it was neutralized by HCl (1M, approx. 50 mL) to pH=7 and extracted with EtOAc (3×110 mL). The organic extracts were washed with brine (150 mL), dried over Na$_2$SO$_4$, filtered, and the solvent was evaporated. The product was obtained as a pale yellow solid (11.1 g, 94%).

$^1$H NMR (500 MHz, DMSO-d$_6$) δ 11.10 (s, 1H); 7.30 (d, J=8.40 Hz, 1H); 7.18 (d, J=8.40 Hz, 1H).

$^{13}$C NMR (126 MHz, DMSO-d$_6$) δ 153.9, 138.1, 124.0, 123.9, 107.7.

HRMS (APCI): calcd. for C$_5$H$_4$ClINO [M+H]$^+$= 255.9021; found [M+H]$^+$=255.9018.

Preparative Example 4A

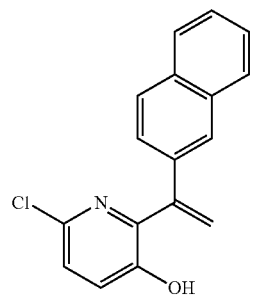 [SMILES: C=C(c1ccc2ccccc2c1)c1nc(Cl)ccc1O]

To a mixture of vinyl boronate from Preparative Example 2A (0.460 g; 1.64 mmol), pyridinol from Preparative Example 3 (0.349 g; 1.37 mmol), K$_3$PO$_4$ (1.196 g; 5.64 mmol) and PdCl$_2$.dppf (0.063 g; 0.068 mmol) were added under N$_2$ 1,2-dimethoxyethane (8 mL) and water (2 mL). The resulting reaction mixture was refluxed for 15 h. Then it was cooled to 25° C., poured into brine (80 mL) and extracted with CH$_2$Cl$_2$ (3×60 mL). The organic extracts were dried over Na$_2$SO$_4$, filtered, and the solvent was evaporated. The residue was purified by column chromatography on silica gel (eluent:CH$_2$Cl$_2$) to yield the product as a pale yellow solid (0.105 g; 27%).

$^1$H NMR (500 MHz, CDCl$_3$) δ 7.85-7.75 (m, 3H); 7.72 (d, J=1.33 Hz, 1H); 7.52 (dd, J=1.86 Hz, 8.57 Hz, 1H); 7.50-7.45 (m, 2H); 7.26-7.22 (m, 2H); 6.06 (s, 1H); 5.79 (s, 1H); 5.07 (s, 1H).

$^{13}$C NMR (126 MHz, CDCl$_3$) δ 149.6, 145.6, 143.8, 142.3, 134.9, 133.7, 133.6, 129.1, 128.7, 127.9, 127.4, 127.0, 126.9, 126.8, 125.0, 124.5, 120.9.

Preparative Example 4B

By essentially same procedure set forth in Preparative Example 4A, using 1-phenylvinylboronic acid pinacol ester instead of vinyl boronate from Preparative Example 2A, the compound given below was prepared.

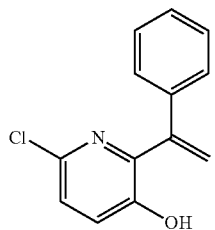 [SMILES: C=C(c1ccccc1)c1nc(Cl)ccc1O]

$^1$H NMR (500 MHz, CDCl$_3$) δ 7.39-7.31 (m, 5H); 7.23-7.18 (m, 2H); 5.93 (d, J=0.73 Hz, 1H); 5.71 (d, J=0.68 Hz, 1H); 5.00 (brs, 1H).
$^{13}$C NMR (126 MHz, CDCl$_3$) δ 149.5, 145.5, 143.8, 142.2, 137.6, 129.3, 129.3, 127.3, 127.2, 125.0, 120.1.
HRMS (APCI): calcd. for C$_{13}$H$_{11}$ClNO [M+H]$^+$= 232.0524; found [M+H]$^+$=232.0525.

Preparative Example 4C

By essentially same procedure set forth in Preparative Example 4A, using the vinyl boronate from Preparative Example 2B, the compound given below was prepared.

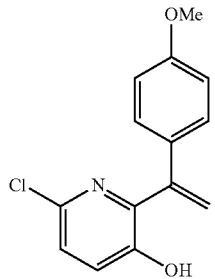 [SMILES: C=C(c1ccc(OC)cc1)c1nc(Cl)ccc1O]

$^1$H NMR (500 MHz, CDCl$_3$) δ 7.30-7.25 (m, 2H); 7.23-7.17 (m, 2H); 6.89-6.85 (m, 2H); 5.83 (d, J=0.65 Hz, 1H); 5.59 (d, J=0.52 Hz, 1H); 5.10 (brs, 1H); 3.80 (s, 3H).
$^{13}$C NMR (126 MHz, CDCl$_3$) δ 160.6, 149.5, 145.8, 143.1, 142.1, 129.8, 128.6, 127.2, 124.9, 118.3, 114.7, 55.6.
HRMS (APCI): calcd. for C$_{14}$H$_{13}$ClNO$_2$ [M+H]$^+$= 262.0629; found [M+H]$^+$=262.0631.

Preparative Example 4D

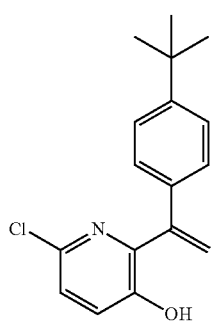 [SMILES: C=C(c1ccc(C(C)(C)C)cc1)c1nc(Cl)ccc1O]

The product from Preparative Example 3 (1.16 g, 4.53 mmol), the product from Preparative Example 2C (1.18 g, 4.12 mmol), K$_3$PO$_4$ (3.5 g, 16.5 mmol), DMF (5.5 mL) and PdCl$_2$(dppf) (150 mg, 0.206 mmol) were placed into a 50 mL round bottom flask and the mixture was stirred under N$_2$ at 80° C. for 14 h. The solvent was evaporated and the residue was loaded on silica gel and purified by column chromatography (CH$_2$Cl$_2$/hexane; 4:1). The product was obtained as a white solid (492 mg, 41%).
$^1$H NMR (500 MHz, CDCl$_3$) δ 7.42-7.37 (m, 2H), 7.32-7.28 (m, 2H), 7.24-7.20 (m, 2H), 5.92 (d, J=0.8 Hz, 1H), 5.69 (d, J=0.7 Hz, 1H), 5.04 (s, 1H), 1.32 (s, 9H).
$^{13}$C NMR (126 MHz, CDCl$_3$) δ 152.5, 149.4, 145.5, 143.4, 142.0, 134.3, 127.1, 126.8, 126.2, 124.7, 119.3, 34.8, 31.4.
HRMS (APCI): calcd. for C$_{17}$H$_{18}$ClNO [M+H]$^+$= 288.1150; found [M+H]$^+$=288.1148.

Preparative Example 4E

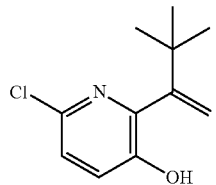

2-(3,3-dimethylbut-1-en-2-yl)-4,4,5,5-tetramethyl-1,3,2-dioxaborolane (400 mg, 1.90 mmol), DMF (7 mL), K$_3$PO$_4$ (1.2 g, 5.72 mmol), the product from Preparative Example 3 (584 mg, 2.28 mmol) and PdCl$_2$(dppf) (69 mg, 95 μmol) were placed into a 25 mL round bottom flask. The mixture was stirred under N$_2$ at 80° C. for 9 h. Then, additional PdCl$_2$(dppf) (47 mg, 64 μmol) was added and the mixture was stirred at 90° C. for additional 45 h. The solvent was evaporated and the residue was loaded on silica gel and purified by column chromatography (from EtOAc/hexane; 1:20 to EtOAc). The product was obtained as a white solid (40 mg, 10%) of limited stability.
$^1$H NMR (300 MHz, CDCl$_3$) δ 7.22 (d, J=8.5 Hz, 1H), 7.12 (d, J=8.5 Hz, 1H), 5.62 (s, 1H), 5.35 (s, 1H), 5.15 (s, 1H), 1.20 (s, 9H).
$^{13}$C NMR (126 MHz, CDCl$_3$) δ 153.4, 148.6, 147.7, 140.8, 125.8, 123.8, 116.0, 37.2, 29.6.
HRMS (APCI): calcd. for C$_{11}$H$_{14}$ClNO [M+H]$^+$= 212.0837; found [M+H]$^+$=212.0835.

Preparative Example 5A

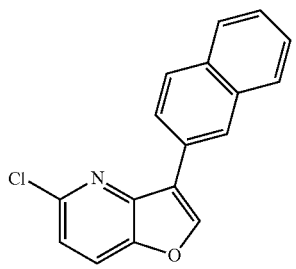 [SMILES: Clc1ccc2occ(-c3ccc4ccccc4c3)c2n1]

A mixture of the product from Preparative Example 4A (0.105 g; 0.37 mmol), copper(I) acetate (0.029 g; 0.24 mmol), 8-hydroxyquinoline (0.037 g; 0.25 mmol) and K$_2$CO$_3$ (0.067 g; 0.48 mmol) in anhydrous N,N-dimethylacetamide (1.5 mL) was stirred under O$_2$ at 140° C. for 18 h. Then the reaction mixture was concentrated under reduce pressure, the residual oil was poured into water (50 mL) and extracted with EtOAc (3×30 mL). The organic extracts were washed with brine (40 mL), dried over MgSO$_4$, filtered and the solvent was evaporated. The resulting residue was purified by column chromatography on silica gel (eluent:hexane/CH$_2$Cl$_2$—1:1) to yield the product as a pale solid product (0.037 g; 36%).

$^1$H NMR (500 MHz, CDCl$_3$) δ 8.67 (s, 1H); 8.23 (s, 1H); 8.01-7.93 (m, 2H); 7.90 (d, J=8.53 Hz, 1H); 7.85-7.82 (m, 1H); 7.75 (d, J=8.60 Hz, 1H); 7.53-7.45 (m, 2H); 7.29 (d, J=8.59 Hz, 1H).

$^{13}$C NMR (126 MHz, CDCl$_3$) δ 148.0, 147.3, 146.4, 146.0, 133.9, 133.2, 128.7, 128.7, 127.9, 127.3, 126.5, 126.4, 126.4, 124.9, 121.7, 121.3, 119.9.

HRMS (APCI): calcd. for C$_{17}$H$_{10}$ClNO [M+H]$^+$= 280.0524; found [M+H]$^+$=280.0526.

Preparative Example 5B

By essentially same procedure set forth in Preparative Example 5A, using product from Preparative Example 41B, the compound given below was prepared.

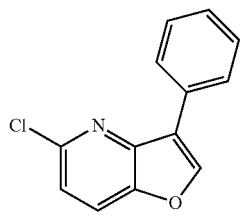 [SMILES: Clc1ccc2occ(-c3ccccc3)c2n1]

$^1$H NMR (500 MHz, CDCl$_3$) δ 8.12 (s, 1H); 8.04-7.99 (m, 2H); 7.73 (d, J=8.61 Hz, 1H); 7.49-7.43 (m, 2H); 7.37-7.32 (m, 1H); 7.27 (d, J=8.60 Hz, 1H).

$^{13}$C NMR (126 MHz, CDCl$_3$) δ 147.9, 147.3, 146.1, 145.9, 129.9, 129.1, 128.2, 127.3, 121.8, 121.3, 119.8.

HRMS (APCI): calcd. for C$_{13}$H$_9$ClNO [M+H]$^+$= 230.0367; found [M+H]$^+$=230.0365.

Preparative Example 5C

By essentially same procedure set forth in Preparative Example 5A, using the product from Preparative Example 4C, the compound given below was prepared.

$^1$H NMR (500 MHz, CDCl$_3$) δ 8.05 (s, 1H); 7.97-7.93 (m, 2H); 7.71 (d, J=8.59 Hz, 1H); 2.25 (d, J=8.59 Hz, 1H); 7.01-6.97 (m, 2H); 3.84 (s, 3H).

$^{13}$C NMR (126 MHz, CDCl$_3$) δ 159.7, 147.9, 147.1, 146.0, 145.2, 128.5, 122.4, 121.5, 121.2, 119.6, 114.6, 55.6.

HRMS (APCI): calcd. for C$_{14}$H$_{11}$ClNO$_2$ [M+H]$^+$= 260.0473; found [M+H]$^+$=260.0469.

Preparative Example 5D

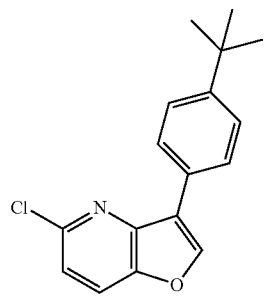 [SMILES: CC(C)(C)c1ccc(-c2coc3ccc(Cl)nc23)cc1]

The product from Preparative Example 4D (470 mg, 1.63 mmol), Cu(OAc)$_2$ (148 mg, 0.816 mmol), quinolin-8-ol (118 mg, 0.816 mmol), K$_2$CO$_3$ (248 mg, 1.79 mmol) were placed into a 50 mL round bottom flask. The flask was filled with O$_2$. Then, N,N-dimethylacetamide (4 mL) was added and the mixture was stirred at 140° C. for 75 min. The solvent was evaporated and the residue was loaded on silica gel and purified by column chromatography (CH$_2$Cl$_2$/hexane; 1:1). The product was obtained as an orange solid (378 mg, 74%).

$^1$H NMR (500 MHz, CDCl$_3$) δ 8.11 (s, 1H), 7.94 (d, J=8.5 Hz, 2H), 7.74 (d, J=8.6 Hz, 1H), 7.51 (d, J=8.5 Hz, 2H), 7.28 (d, J=8.6 Hz, 1H), 1.36 (s, 9H).

$^{13}$C NMR (126 MHz, CDCl$_3$) δ 151.2, 147.8, 147.1, 146.0, 145.7, 127.0, 126.8, 126.0, 121.7, 121.1, 119.6, 34.8, 31.5.

HRMS (APCI): calcd. for C$_{17}$H$_{16}$ClNO [M+H]$^+$= 286.0993; found [M+H]$^+$=286.0991.

Preparative Example 5E

By essentially same procedure set forth in Preparative Example 5D, using the product from Preparative Example 4E, the compound given below was prepared.

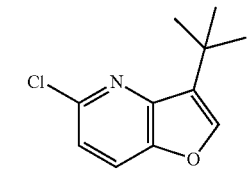

White solid.

$^1$H NMR (500 MHz, CDCl$_3$) δ 7.63 (d, J=8.6 Hz, 1H), 7.56 (s, 1H), 7.17 (d, J=8.6 Hz, 1H), 1.48 (s, 9H).

$^{13}$C NMR (126 MHz, CDCl$_3$) δ 147.7, 147.0, 145.8, 144.3, 131.0, 120.6, 118.8, 31.0, 29.6.

HRMS (APCI): calcd. for [M+H]$^+$=210.0680; found [M+H]$^+$=210.0682.

Preparative Example 6A

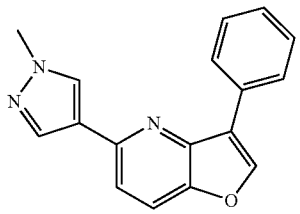 [SMILES: Cn1cc(-c2ccc3occ(-c4ccccc4)c3n2)cn1]

To a mixture of the product from Preparative Example 5B (0.052 g; 0.23 mmol), 1-methylpyrazole-4-boronic acid pinacol ester (0.059 g; 0.28 mmol), K$_3$PO$_4$ (0.227 g; 1.07 mmol) and PdCl$_2$(dppf) (0.011 g; 0.015 mmol) were added under N$_2$ 1,2-dimethoxyethane (2 mL) and water (0.5 mL). The resulting reaction mixture was refluxed for 18 h. Then it was cooled to 25° C., diluted with EtOAc (10 mL), poured into brine (25 mL) and extracted with EtOAc (3×10 mL). The organic extracts were dried over Na$_2$SO$_4$, filtered, and the solvent was evaporated. The residue was purified by column chromatography on silica gel (eluent:CH$_2$Cl$_2$/EtOAc—2:1) to yield the product as a pale orange solid (0.051 g; 81%).

$^1$H NMR (500 MHz, CDCl$_3$) δ 8.17-8.13 (m, 2H); 8.09 (s, 1H); 7.99 (d, J=5.58 Hz, 2H); 7.72 (d, J=8.61 Hz, 1H); 7.50-7.7.44 (m, 2H); 7.42 (d, J=8.60 Hz; 1H); 7.37-7.32 (m, 1H); 3.96 (s, 3H).

$^{13}$C NMR (126 MHz, CDCl$_3$) δ 148.9, 147.7, 145.9, 145.2, 137.7, 131.0, 129.1, 128.9, 127.8, 127.3, 124.4, 121.7, 119.2, 115.8, 39.4.

HRMS (APCI): calcd. for C$_{17}$H$_{14}$N$_3$O [M+H]$^+$=276.1131; found [M+H]$^+$=276.1128.

Preparative Example 6B

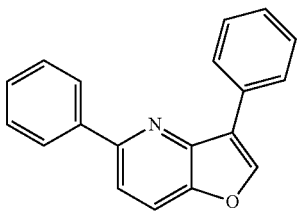 [SMILES: c1ccc(-c2ccc3occ(-c4ccccc4)c3n2)cc1]

To a mixture of the product from Preparative Example 5B (0.311 g; 1.36 mmol), phenylboronic acid pinacol ester (0.225 g; 1.85 mmol), K$_3$PO$_4$ (1.20 g; 5.64 mmol) and PdCl$_2$.dppf (0.062 g; 0.084 mmol) were added under N$_2$ 1,2-dimethoxyethane (8 mL) and water (2 mL). The reaction mixture was refluxed under N$_2$ for 19 h. Then it was cooled to 25° C., diluted with EtOAc (40 mL), poured into brine (50 mL) and extracted with EtOAc (3×40 mL). The organic extracts were dried over Na$_2$SO$_4$, filtered, and the solvent was evaporated. The residue was purified by column chromatography on silica gel (eluent:hexane/EtOAc—5:1) to yield the product as a pale yellow wax (0.262 g; 71%).

$^1$H NMR (500 MHz, CDCl$_3$) δ 8.26-8.19 (m, 2H); 8.17-8.10 (m, 3H); 7.83 (d, J=8.66 Hz, 1H); 7.73 (d, J=8.67 Hz, 1H); 7.54-7.46 (m, 4H); 7.45-7.33 (m, 2H).

$^{13}$C NMR (126 MHz, CDCl$_3$) δ 154.3, 148.3, 146.1, 145.4, 140.0, 130.9, 129.0, 128.9, 128.8, 127.9, 127.4, 127.3, 122.0, 119.2, 116.8.

HRMS (APCI): calcd. for C$_{19}$H$_{14}$NO [M+H]$^+$=272.1070; found [M+H]$^+$=272.1074.

Preparative Example 6C

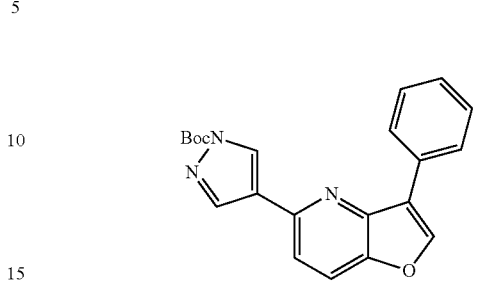

To a mixture of the product from Preparative Example 5B (0.078 g; 0.34 mmol), 1-Boc-pyrazole-4-boronic acid pinacol ester (0.122 g; 0.42 mmol), K$_3$PO$_4$ (0.282 g; 1.33 mmol) and palladium catalyst PdCl$_2$.dppf (0.018 g; 0.024 mmol) were added under N$_2$ 1,2-dimethoxyethane (2 mL) and water (0.5 mL). The reaction mixture was refluxed under N$_2$ for 15 h. Then it was cooled to 25° C., diluted with EtOAc (15 mL), poured into brine (25 mL) and extracted with EtOAc (3×15 mL). The organic extracts were dried over Na$_2$SO$_4$, filtered, and the solvent was evaporated. The residue was purified by column chromatography on silica gel (eluent:hexane/EtOAc—2:1) to yield the product as a pale yellow solid (0.047 g; 38%).

$^1$H NMR (300 MHz, CDCl$_3$) δ 8.27 (s, 1H); 8.18-8.11 (m, 3H); 7.78 (d, J=8.59 Hz, 1H); 7.53-7.44 (m, 3H); 7.40-7.32 (m, 1H); 1.68 (s, 9H).

Preparative Example 6D

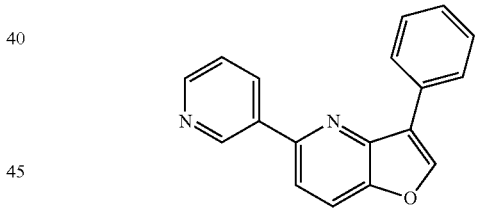

To a mixture of the product from Preparative Example 5B (0.088 g; 0.38 mmol), 3-pyridineboronic acid pinacol ester (0.098 g; 0.48 mind), K$_3$PO$_4$ (0.336 g; 1.58 mmol) and palladium catalyst PdCl$_2$.dppf (0.019 g; 0.026 mmol) were added under N$_2$ 1,2-dimethoxyethane (2 mL) and water (0.5 mL). The reaction mixture was refluxed under N$_2$ for 19 h. Then it was cooled to 25° C., diluted with EtOAc (15 mL), poured into brine (25 mL) and extracted with EtOAc (3×15 mL). The organic extracts were dried over Na$_2$SO$_4$, filtered, and the solvent was evaporated. The residue was purified by column chromatography on silica gel (eluent:CH$_2$Cl$_2$/MeOH—15:1) to yield the product as a pale brown solid (0.087 g; 83%).

$^1$H NMR (500 MHz, CDCl$_3$) δ 9.43 (brs, 1H); 8.73 (brs, 1H); 8.44 (d, J=7.88 Hz, 1H); 8.23-8.15 (m, 3H); 7.87 (d, J=8.57 Hz, 1H); 7.74 (d, J=8.61 Hz, 1H); 7.53-7.34 (m, 4H).

$^{13}$C NMR (126 MHz, CDCl$_3$) δ 151.5, 149.6, 148.7, 148.6, 146.6, 145.8, 1358, 134.8, 130.6, 129.1, 128.1, 127.3, 124.2, 122.0, 119.5, 116.7.

HRMS (APCI): calcd. for $C_{18}H_{13}N_2O$ [M+H]$^+$= 273.1022; found [M+H]$^+$=273.1022.

Preparative Example 7A

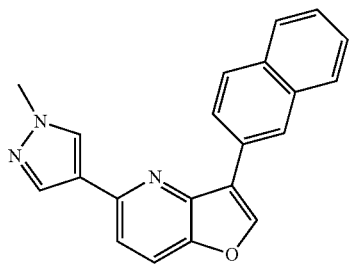 [SMILES: Cn1cc(-c2ccc3occ(-c4ccc5ccccc5c4)c3n2)cn1]

To a mixture of Preparative Example 5A (0.053 g; 0.19 mmol), 1-methylpyrazole-4-boronic acid pinacol ester (0.048 g; 0.23 mmol), $K_3PO_4$ (0.177 g; 0.83 mmol) and $PdCl_2$.dppf (0.010 g; 0.014 mmol) were added under $N_2$ 1,2-dimethoxyethane (2 mL) and water (0.5 mL). The reaction mixture was refluxed for 19 h. Then it was cooled to 25° C., diluted with EtOAc (10 mL), poured into brine (25 mL) and extracted with EtOAc (3×10 mL). The organic extracts were dried over $Na_2SO_4$, filtered and the solvent was evaporated. The residue was purified by column chromatography on silica gel (eluent:EtOAc/MeOH—20:1) to yield the product as a pale yellow solid (0.049 g; 79%).

$^1$H NMR (500 MHz, CDCl$_3$) δ 8.86 (s, 1H); 8.21 (s, 1H); 8.11-7.99 (m, 3H); 7.97-7.89 (m, 2H); 7.85 (d, J=7.82 Hz, 1H); 7.76 (d, J=8.26 Hz, 1H); 7.54-7.42 (m, 3H); 3.99 (s, 3H).

$^{13}$C NMR (126 MHz, CDCl$_3$) δ 148.9, 147.8, 145.9, 145.6, 137.8, 133.9, 133.1, 129.2, 128.6, 128.5, 128.3, 128.0, 126.5, 126.2, 125.1, 124.4, 121.6, 119.4, 116.0, 39.5.

HRMS (APCI): calcd. for $C_{21}H_{16}N_3O$ [M+H]$^+$= 326.1288; found [M+H]$^+$=326.1284.

Preparative Example 7B

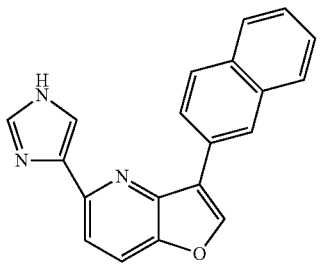 [SMILES: c1ccc2cc(-c3coc4ccc(-c5c[nH]cn5)nc34)ccc2c1]

Tert-butyl 4-(4,4,5,5-tetramethyl-1,3,2-dioxaborolan-2-yl)-1H-pyrazole-1-carboxylate (77 mg, 0.26 mmol), the product from Preparative Example 5A (61 mg, 0.22 mmol), $K_3PO_4$ (180 mg, 0.85 mmol), 1,2-dimethoxyethane (2 mL), $H_2O$ (0.5 mL) and $PdCl_2$(dppf) (1.8 mg, 0.008 mmol) were added into a 25 mL round bottom flask. The mixture was refluxed under $N_2$ for 18 h, then saturated aqueous solution of $NH_4Cl$ (15 mL) was added, the mixture was extracted with EtOAc (10 mL) and then with $CH_2Cl_2$ (2×20 mL). The organic extracts were dried over $Na_2SO_4$, filtered, and the solvents were evaporated. The residue was loaded on silica gel and purified by column chromatography (EtOAc/hexane; 5:4) to afford the product as a light yellow solid (47 mg, 69%).

$^1$H NMR (500 MHz, CDCl$_3$) δ 8.94 (s, 1H), 8.32-8.20 (m, 3H), 8.11 (d, J=8.6 Hz, 1H), 8.00-7.91 (m, 2H), 7.87 (d, J=7.8 Hz, 1H), 7.81 (d, J=8.6 Hz, 1H), 7.56-7.47 (m, 3H).

$^1$H NMR (300 MHz, DMSO-d6) δ 13.04 (b, 1H), 9.12 (s, 1H), 8.95 (s, 1H), 8.52-8.20 (m, 3H), 8.14-7.99 (m, 3H), 7.99-7.90 (m, 1H), 7.78 (d, J=8.7 Hz, 1H), 7.63-7.49 (m, 2H).

$^{13}$C NMR (126 MHz, CDCl$_3$) δ 148.6, 147.8, 146.0, 145.5, 133.8, 133.0, 128.5, 128.4, 128.2, 127.9, 126.4, 126.1, 124.9, 121.5, 119.2, 116.1.

HRMS (APCI): calcd. for $C_{20}H_{13}N_3O$ [M+H]$^+$= 312.1131; found [M+H]$^+$=312.1129.

Preparative Example 7C

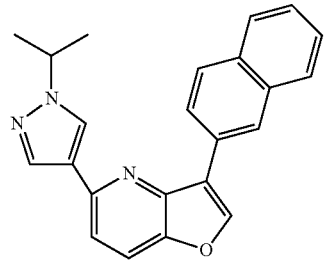 [SMILES: CC(C)n1cc(-c2ccc3occ(-c4ccc5ccccc5c4)c3n2)cn1]

1-isopropyl-4-(4,4,5,5-tetramethyl-1,3,2-dioxaborolan-2-yl)-1H-pyrazole (41 mg, 0.17 mmol), the product from Preparative Example 5A (40 mg, 0.14 mmol), $K_3PO_4$ (91 mg, 0.43 mmol), 1,2-dimethoxyethane (2 mL), $H_2O$ (0.5 mL) and $PdCl_2$(dppf) (3.1 mg, 4.3 µmol) were added into a 25 mL round bottom flask and the mixture was refluxed under $N_2$ for 2 h. The solvent was evaporated and the residue was loaded on silica gel and purified by column chromatography (EtOAc/hexane; 1:1) to yield the product as a light yellow wax (40 mg, 79%).

$^1$H NMR (500 MHz, CDCl$_3$) δ 8.91 (s, 1H), 8.23 (s, 1H), 8.13-8.07 (m, 3H), 7.98-7.92 (m, 2H), 7.87 (d, J=8.0 Hz, 1H), 7.78 (d, J=8.6 Hz, 1H), 7.55-7.47 (m, 3H), 4.60 (sep, J=13.4, 6.7 Hz, 1H), 1.62 (s, 3H), 1.60 (s, 3H).

$^{13}$C NMR (126 MHz, CDCl$_3$) δ 149.1, 147.6, 145.9, 145.3, 137.3, 133.8, 133.0, 128.4, 128.3, 127.8, 126.3, 126.0, 125.4, 125.0, 123.6, 121.5, 119.2, 115.8, 54.2, 23.1.

HRMS (APCI): calcd. for $C_{23}H_{19}N_3O$ [M+H]$^+$= 354.1601; found [M+H]$^+$=354.1596.

Preparative Example 7D

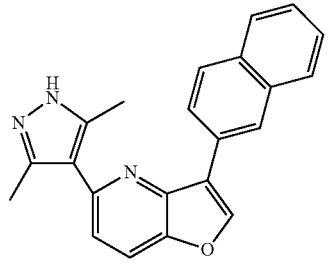 [SMILES: Cc1n[nH]c(C)c1-c1ccc2occ(-c3ccc4ccccc4c3)c2n1]

Tert-butyl 3,5-dimethyl-4-(4,4,5,5-tetramethyl-1,3,2-dioxaborolan-2-yl)-1H-pyrazole-1-carboxylate (55 mg, 0.17 mmol), the product from Preparative Example 5A (40 mg, 0.14 mmol), $K_3PO_4$ (91 mg, 0.43 mmol), 1,2-dimethoxyethane (2 mL), $H_2O$ (0.5 mL) and $PdCl_2$(dppf) (3.1 mg, 4.3

µmol) were added into a 25 mL round bottom flask and the mixture was refluxed under N₂ for 24 h. Then, additional tert-butyl 3,5-dimethyl-4-(4,4,5,5-tetramethyl-1,3,2-dioxaborolan-2-yl)-1H-pyrazole-1-carboxylate (30 mg, 0.09 mmol) and PdCl₂(dppf) (4 mg, 5.4 µmol) were added and the mixture was refluxed under N₂ for additional 24 h. The solvent was evaporated and the residue was loaded on silica gel and purified by column chromatography (EtOAc/MeOH; 30:1) and then re-chromatographed (EtOAc/hexane; 1:1). So obtained material was purified by preparative TLC (EtOAc/hexane; 1:1) and then by another preparative TLC (CH₂Cl₂/MeOH; 15:1). The product was obtained as a colorless wax (7.2 mg, 29% yield).

¹H NMR (300 MHz, CDCl₃) δ 8.99 (s, 1H), 8.28 (s, 1H), 8.06 (dd, J=8.6, 1.6 Hz, 1H), 7.99-7.79 (m, 4H), 7.57-7.43 (m, 2H), 7.39 (d, J=8.6 Hz, 1H), 2.62 (s, 6H).

¹³C NMR (126 MHz, CDCl₃) δ 150.4, 147.0, 145.8, 145.3, 144.7, 143.4, 133.8, 132.9, 128.4, 128.3, 128.2, 127.8, 126.4, 126.3, 126.0, 124.7, 121.6, 118.9, 118.8, 118.1, 12.9, 12.3.

HRMS (APCI): calcd. for $C_{22}H_{17}N_3O$ [M+H]⁺=340.1444; found [M+H]⁺=340.1441.

Preparative Example 7E

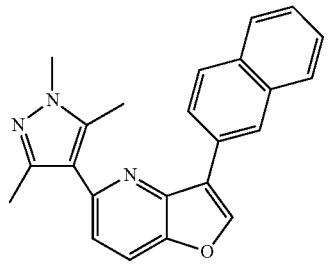 [SMILES: Cc1nn(C)c(C)c1-c1ccc2occ(-c3ccc4ccccc4c3)c2n1]

(1,3,5-trimethyl-1H-pyrazol-4-yl)boronic acid (33 mg, 0.21 mmol), the product from Preparative Example 5A (50 mg, 0.18 mmol), K₃PO₄ (133 mg, 0.63 mmol), 1,2-dimethoxyethane (2.4 mL), H₂O (0.6 mL) and PdCl₂(dppf) (6.5 mg, 8.9 mmol) were added into a 10 mL round bottom flask and the mixture was refluxed under N₂ for 18 h. Additional PdCl₂(dppf) (4 mg, 5.4 µmol) and K₃PO₄ (118 mg, 0.56 mmol) were added and the mixture was refluxed for additional 12 h. Then, another portion of PdCl₂(dppf) (4 mg, 5.4 µmol) was added and the mixture was refluxed for additional 10 h. The solvent was evaporated and the residue was loaded on silica gel and purified by column chromatography (EtOAc/hexane; from 1:1 to 2:1) and then by preparative TLC (CH₂Cl₂/MeOH; 15:1) to yield the product as a colorless wax (5 mg, 8%).

¹H NMR (500 MHz, CDCl₃) δ 8.99 (s, 1H), 8.28 (s, 1H), 8.06 (dd, J=8.5, 1.7 Hz, 1H), 7.94-7.88 (m, 2H), 7.88-7.82 (m, 2H), 7.54-7.44 (m, 2H), 7.35 (d, J=8.6 Hz, 1H), 3.85 (s, 3H), 2.59 (s, 3H), 2.51 (s, 3H).

¹³C NMR (126 MHz, CDCl₃) δ 150.7, 147.0, 145.9, 145.8, 145.3, 138.1, 133.9, 132.9, 128.4, 128.3, 128.2, 127.8, 126.4, 126.3, 126.0, 124.7, 119.2, 118.9, 118.8, 36.1, 13.7, 11.2.

HRMS (APCI): calcd. for $C_{23}H_{19}N_3O$ [M+H]⁺=354.1601; found M+H]⁺=354.1599.

Preparative Example 7F

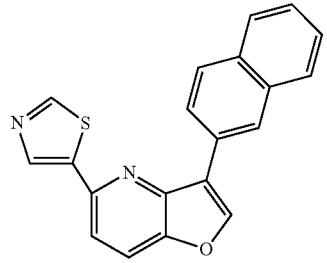 [SMILES: c1ccc2cc(-c3coc4ccc(-c5cncs5)nc34)ccc2c1]

A mixture of 5-thiazole boronic acid MIDA ester (69 mg, 0.29 mmol), the product from Preparative Example 5A (62 mg, 0.22 mmol), K₃PO₄ (165 mg, 0.78 mmol), 1,2-dimethoxyethane (2 mL), H₂O (0.5 mL) and PdCl₂(dppf) (8.1 mg, 11 µmol) was stirred at 60° C. under N₂ for 2 h and then at 80° C. for 7 h. Additional PdCl₂(dppf) (4 mg, 5.4 µmol), the mixture was refluxed for 27 h, then additional PdCl₂(PPh₃)₂ (4 mg, 5.7 µmol) was added and the mixture was refluxed for additional 24 h. Then, additional Pd(PPh₃)₄ (5 mg, 4.3 µmol) and 5-thiazole boronic acid MIDA ester (20 mg, 0.083 mmol) were added and the mixture was refluxed for additional 24 h. The solvent was evaporated and the residue was loaded on silica gel and purified by column chromatography (EtOAc/hexane; from 1:2 to 1:1) and then by preparative TLC (EtOAc/hexane; 1:1). The product was obtained as a light yellow solid (7 mg, 10%).

¹H NMR (300 MHz, CDCl₃) δ 8.98 (s, 1H), 8.88 (s, 1H), 8.41 (s, 1H), 8.30 (s, 1H), 8.07 (dd, J=8.6, 1.7 Hz, 1H), 8.03-7.84 (m, 4H), 7.74 (d, J=8.6 Hz, 1H), 7.58-7.48 (m, 2H).

¹³C NMR (126 MHz, CDCl₃) δ 154.4, 148.4, 147.0, 146.3, 146.1, 141.4, 139.7, 133.8, 133.0, 128.6, 128.5, 127.8, 127.7, 126.5, 126.5, 126.3, 124.6, 121.4, 119.5, 116.0.

HRMS (APCI): calcd. for $C_{20}H_{12}N_2OS$ [M+H]⁺=329.0743; found [M+H]⁺=329.0747.

Preparative Example 8A

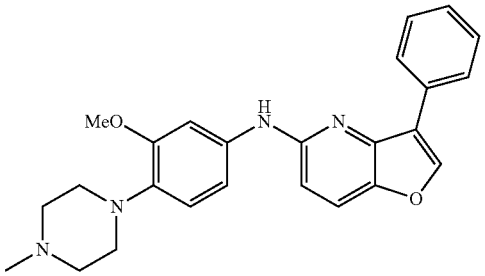 [SMILES: COc1cc(Nc2ccc3occ(-c4ccccc4)c3n2)ccc1N1CCN(C)CC1]

To a freshly prepared solution of (S)-1-[(R$_P$)-2-(dicyclohexylphosphino)ferrocenyl]ethyldi-tert-butylphosphine (0.013 g; 0.023 mmol) and Pd(OAc)₂ (0.007 g; 0.030 mmol) in anhydrous 1,2-dimethoxyethane (2 mL) were added the product from Preparative Example 5B (0.053 g; 0.23 mmol), t-BuOK (0.036 g; 0.32 mmol) and 3-methoxy-4-(4-methylpiperazin-1-yl)aniline (0.064 g; 0.29 mmol) and the resulting mixture was stirred under N₂ at 100° C. for 16 h. Then it was cooled to 25° C., diluted with EtOAc (10 mL), poured into brine (25 mL) and extracted with EtOAc (3×10 mL). The organic extracts were dried over MgSO₄, filtered and the solvent was evaporated. The residue was purified by column chromatography on silica gel (eluent:CH$_2$Cl$_2$/7N NH$_3$ in MeOH—30:1) to yield the product as a dark orange semi-solid (0.079 g; 83%).

$^1$H NMR (500 MHz, CDCl$_3$) δ 8.05-8.02 (m, 2H); 7.99 (s, 1H); 7.59 (d, J=8.93 Hz, 1H); 7.44-7.39 (m, 2H); 7.33-7.27 (m, 2H); 6.91-6.81 (m, 2H); 6.70 (d, J=8.94 Hz, 1H); 6.49 (brs, 1H); 3.80 (s, 3H); 3.10 (s, 4H); 2.68 (s, 4H); 2.38 (s, 3H).

$^{13}$C NMR (126 MHz, CDCl$_3$) δ 154.0, 153.1, 144.6, 143.7, 137.3, 136.6, 131.3, 128.9, 127.6, 127.2, 121.5, 121.0, 118.9, 112.3, 106.1, 104.8, 55.8, 55.6, 50.9, 46.2.

HRMS (APCI): calcd. for C$_{25}$H$_{27}$N$_4$O$_2$ [M+H]$^+$= 415.2129; found [M+H]$^+$=415.2129.

Preparative Example 8B

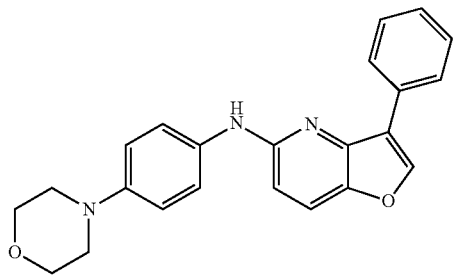 [SMILES: c1ccc(-c2coc3ccc(Nc4ccc(N5CCOCC5)cc4)nc23)cc1]

To a freshly prepared solution of (S)-1-[(R$_P$)-2-(dicyclohexylphosphino)ferrocenyl]ethyldi-tert-butylphosphine (0.007 g; 0.012 mmol) and Pd(OAc)$_2$ (0.004 g; 0.018 mmol) in anhydrous 1,2-dimethoxyethane (2 mL) were added the product from Preparative Example 5B (0.067 g; 0.29 mmol), t-BuOK (0.041 g; 0.43 mmol) and 4-morpholinoaniline (0.062 g; 0.35 mmol) and the resulting mixture was stirred under N$_2$ at 100° C. for 14 h. Then it was cooled to 25° C., diluted with EtOAc (10 mL), poured into brine (25 mL) and extracted with EtOAc (3×10 mL). The organic extracts were dried over MgSO$_4$, filtered, and the solvent was evaporated. The residue was purified by column chromatography on silica gel (eluent:CH$_2$Cl$_2$/MeOH—50:1) to yield the product as an orange solid (0.062 g; 58%).

$^1$H NMR (500 MHz, DMSO-d6) δ 8.92 (s, 1H); 8.59 (s, 1H); 8.25-8.20 (m, 2H); 7.84 (d, J=9.01 Hz, 1H); 7.72-7.66 (m, 2H); 7.54-7.47 (m, 2H); 7.38-7.31 (m, 1H); 6.98-6.91 (m, 2H); 6.79 (d, J=9.04 Hz, 1H); 3.78-3.72 (m, 4H); 3.08-3.03 (m, 4H).

$^{13}$C NMR (126 MHz, DMSO-d6) δ 153.6, 145.3, 145.0, 143.0, 141.6, 134.6, 131.0, 128.5, 127.0, 126.2, 121.0, 119.7, 118.9, 115.8, 107.7, 66.1, 49.4.

HRMS (APCI): calcd. for C$_{23}$H$_{22}$N$_3$O$_2$ [M+H]$^+$= 372.1707; found [M+H]$^+$=372.1704.

Preparative Example 8C

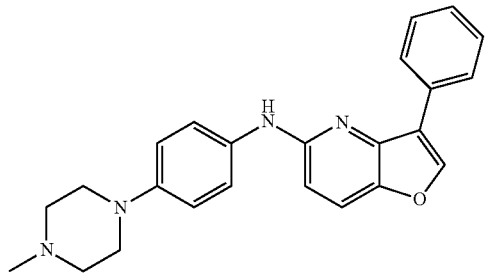 [SMILES: CN1CCN(c2ccc(Nc3ccc4occ(-c5ccccc5)c4n3)cc2)CC1]

To a freshly prepared solution of (S)-1-[(R$_P$)-2-(dicyclohexylphosphino)ferrocenyl]ethyldi-tert-butylphosphine (0.008 g; 0.014 mmol) and Pd(OAc)$_2$ (0.010 g; 0.042 mmol) in anhydrous 1,2-dimethoxyethane (2 mL) were added the product from Preparative Example 5B (0.061 g; 0.26 mmol), t-BuOK (0.038 g; 0.40 mmol) and 4-(4-methyl-1-piperazinyl)aniline (0.057 g; 0.30 mmol) and the resulting mixture was stirred under N$_2$ at 100° C. for 19 h. Then it was cooled to 25° C., diluted with EtOAc (15 mL), poured into brine (25 mL) and extracted with EtOAc (3×15 mL). The organic extracts were dried over MgSO$_4$, filtered and the solvent was evaporated. The resulting residue was purified by column chromatography on silica gel (eluent:CH$_2$Cl$_2$/7N NH$_3$ in MeOH—15:1) to yield the product as a pale brown solid (0.069 g; 68%).

$^1$H NMR (500 MHz, CDCl$_3$) δ 8.08-8.04 (m, 2H); 7.99 (s, 1H); 7.56 (d, J=8.96 Hz, 1H); 7.46-7.41 (m, 2H); 7.37-7.28 (m, 3H); 6.93 (d, J=5.55 Hz, 2H); 6.66 (d, J=8.61 Hz, 1H); 6.41 (brs, 1H); 3.18 (brs, 4H); 2.63-2.57 (m, 4H); 2.36 (s, 3H).

$^{13}$C NMR (126 MHz, CDCl$_3$) δ 147.8, 144.5, 143.8, 134.0, 131.3, 128.9, 127.5, 127.2, 122.8, 122.7, 121.3, 120.9, 117.5, 105.4, 55.4, 50.0, 46.3.

HRMS (APCI): calcd. for C$_{24}$H$_{25}$N$_4$O [M+H]$^+$= 385.2023; found [M+H]$^+$=385.2030.

Preparative Example 8D

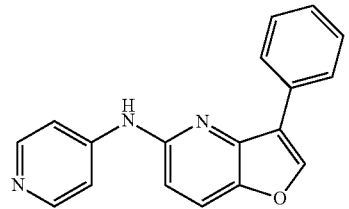 [SMILES: c1ccc(-c2coc3ccc(Nc4ccncc4)nc23)cc1]

To a freshly prepared solution of (S)-1-[(R$_P$)-2-(dicyclohexylphosphino)ferrocenyl]ethyldi-tert-butylphosphine (0.009 g; 0.016 mmol) and Pd(OAc)$_2$ (0.015 g; 0.068 mmol) in anhydrous 1,2-dimethoxyethane (2 mL) were added the product from Preparative Example 5B (0.054 g; 0.23 mmol), t-BuOK (0.033 g; 0.34 mmol) and 4-aminopyridine (0.024 g; 0.26 mmol) and the resulting mixture was stirred under N$_2$ at 100° C. for 14 h. Then it was cooled to 25° C., diluted with EtOAc (10 mL), poured into brine (25 mL) and extracted with EtOAc (3×10 mL). The organic extracts were dried over MgSO$_4$, filtered and the solvent was evaporated. The residue was purified by column chromatography on silica gel (eluent:CH$_2$Cl$_2$/7N NH$_3$ in MeOH—10:1) to yield the product as a pale yellow solid (0.034 g; 50%).

$^1$H NMR (500 MHz, DMSO-d6) δ 9.71 (s, 1H); 8.71 (s, 1H); 8.35 (d, J=5.44 Hz, 2H); 8.19 (d, J=7.31 Hz, 2H); 8.02 (d, J=8.93 Hz, 1H); 7.77 (d, J=5.66 Hz, 2H); 7.58-7.50 (m, 3H); 7.41-7.35 (m, 1H); 6.98 (d, J=8.94 Hz, 1H).

$^{13}$C NMR (126 MHz, DMSO-d6) δ 152.0, 149.7, 147.8, 145.9, 143.8, 141.8, 130.5, 128.6, 127.3, 126.3, 121.5, 120.0, 111.3, 109.2.

HRMS (APCI): calcd. for C$_{18}$H$_{14}$N$_3$O [M+H]$^+$= 288.1131; found [M+H]$^+$=288.1131.

Preparative Example 8E

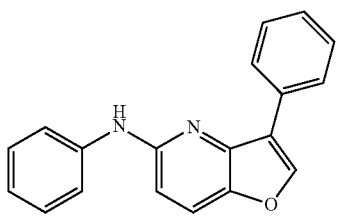 [SMILES: c1ccc(Nc2ccc3occ(-c4ccccc4)c3n2)cc1]

To a freshly prepared solution of (S)-1-[(R$_P$)-2-(dicyclohexylphosphino)ferrocenyl]ethyldi-tert-butylphosphine (0.011 g; 0.020 mmol) and palladium catalyst Pd(OAc)$_2$ (0.008 g; 0.033 mmol) in anhydrous 1,2-dimethoxyethane (2 mL) were added the product from Preparative Example 5B (0.053 g; 0.23 mmol), t-BuOK (0.032 g; 0.34 mmol) and aniline (0.025 mL; 0.27 mmol) and the resulting mixture was stirred under N$_2$ at 100° C. for 15 h. Then it was cooled to 25° C., diluted with EtOAc (10 mL), poured into brine (25 mL) and extracted with EtOAc (3×10 mL). The organic extracts were dried over MgSO$_4$, filtered and the solvent was evaporated. The residue was purified by column chromatography on silica gel (eluent:hexane/EtOAc—5:1) to yield the product as a brownish semi-solid (0.050 g; 76%).

$^1$H NMR (500 MHz, CDCl$_3$) δ 8.08-8.04 (m, 2H); 8.02 (s, 1H); 7.64 (d, J=8.96 Hz, 1H); 7.49-7.43 (m, 4H); 7.37-7.29 (m, 3H); 7.07-7.00 (m, 1H); 6.81 (d, J=8.96 Hz, 1H).

$^{13}$C NMR (126 MHz, CDCl$_3$) δ 153.4, 144.8, 144.7, 141.2, 130.9, 129.4, 129.0, 127.8, 127.2, 122.7, 121.3, 119.9, 106.5.

HRMS (APCI): calcd. for C$_{19}$H$_{15}$N$_2$O [M+H]$^+$= 287.1179; found [M+H]$^+$=287.1180.

Preparative Example 8F

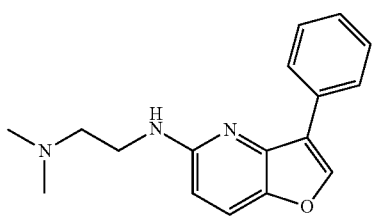 [SMILES: CN(C)CCNc1ccc2occ(-c3ccccc3)c2n1]

To a solution of the product from Preparative Example 5B (0.045 g; 0.20 mmol), (R)-BINAP (0.017 g; 0.027 mmol), Pd$_2$(dba)$_3$ (0.014 g; 0.015 mmol) and t-BuOK (0.033 g; 0.29 mmol) in anhydrous toluene (2 mL) was added N,N-dimethylethylenediamine (0.022 mL; 0.20 mmol) and the resulting mixture was stirred under N$_2$ at 80° C. for 20 h. Then it was cooled to 25° C., diluted with EtOAc (10 mL), poured into water (25 mL) and extracted with EtOAc (3×10 mL). The organic extracts were washed with brine (15 mL), dried over MgSO$_4$, filtered and the solvent was evaporated. The residue was purified by preparative TLC (eluent:CH$_2$Cl$_2$/7N NH$_3$ in MeOH—17:1) to yield the product as an orange wax (0.024 g; 43%).

$^1$H NMR (500 MHz, CDCl$_3$) δ 8.13-8.08 (m, 2H); 7.96 (s, 1H); 7.51 (d, J=8.93 Hz, 1H); 7.45-7.39 (m, 2H); 7.32-7.26 (m, 1H); 6.39 (d, J=8.93 Hz, 1H); 5.04-4.95 (m, 1H); 3.50 (dd, J=5.71 Hz, 11.41 Hz, 2H); 2.60 (t, J=6.06 Hz, 2H); 2.29 (s, 3H).

$^{13}$C NMR (126 MHz, CDCl$_3$) δ 156.9, 143.9, 143.8, 143.5, 131.7, 128.8, 127.3, 127.0, 121.1, 120.7, 105.4, 58.6, 45.6, 40.1.

HRMS (APCI): calcd. for C$_{17}$H$_{20}$N$_3$O [M+H]$^+$= 282.1601; found [M+H]$^+$=282.1600.

Preparative Example 8G

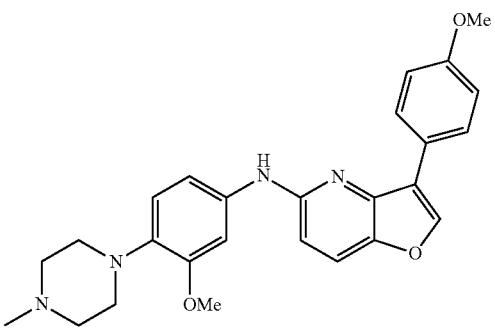 [SMILES: COc1ccc(-c2coc3ccc(Nc4ccc(N5CCN(C)CC5)c(OC)c4)nc23)cc1]

To a freshly prepared solution of (S)-1-[(R$_P$)-2-(dicyclohexylphosphino)ferrocenyl]ethyldi-tert-butylphosphine (0.011 g; 0.023 mmol) and Pd(OAc)$_2$ (0.007 g; 0.030 mmol) in anhydrous 1,2-dimethoxyethane (2 mL) were added the product from Preparative Example 5C (0.054 g; 0.22 mmol), t-BuONa (0.030 g; 0.31 mmol) and 3-methoxy-4-(4-methylpiperazin-1-yl)aniline (0.056 g; 0.25 mmol) and the resulting mixture was stirred under N$_2$ at 100° C. for 18 h. Then it was cooled to 25° C., diluted with EtOAc (10 mL), poured into brine (25 mL) and extracted with EtOAc (3×10 mL). The organic extracts were dried over MgSO$_4$, filtered, and the solvent was evaporated. The residue was purified by column chromatography on silica gel (eluent:CH$_2$Cl$_2$/7N NH$_3$ in MeOH—17:1) to yield the product as a pale orange foam (0.041 g; 42%).

$^1$H NMR (500 MHz, CDCl$_3$) δ 7.99-7.95 (m, 2H); 7.91 (s, 1H); 7.56 (d, J=8.92 Hz, 1H); 7.27-7.22 (m, 1H); 6.91-6.81 (m, 2H); 6.68 (d, J=8.93 Hz, 1H); 6.50 (brs, 1H); 3.83 (s, 3H); 3.80 (s, 3H); 3.08 (brs, 4H); 2.64 (brs, 4H); 2.36 (s, 3H).

$^{13}$C NMR (126 MHz, CDCl$_3$) δ 159.2, 153.9, 153.1, 144.4, 143.7, 137.3, 136.6, 128.4, 123.8, 121.1, 120.9, 118.8, 114.3, 112.3, 106.3, 104.8, 55.7, 55.6, 55.5, 51.1, 46.3.

HRMS (APCI): calcd. for C$_{26}$H$_{29}$N$_4$O$_3$ [M+H]$^+$= 445.2234; found [M+H]$^+$=445.2235.

Preparative Example 9

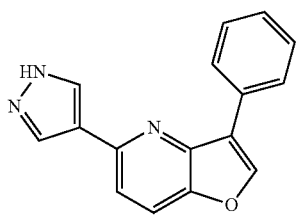 [SMILES: c1ccc(-c2coc3ccc(-c4cn[nH]c4)nc23)cc1]

To a stirred solution of the product from Preparative Example 6C (0.049 g; 0.14 mmol) in ethanol (2 mL) was added aqueous solution of HCl (3M; 0.9 mL; 2.7 mmol) and the resulting mixture was stirred under N$_2$ at 60° C. for 8 h. Then, the ethanol and HCl were evaporated and the oily residue was mixed with CH$_2$Cl$_2$ (2 mL), MeOH (1 mL) and Na$_2$CO$_3$ (200 mg) and the mixture was stirred at 25° C. After 20 min., the solvents were evaporated and the solid residue was purified by column chromatography on silica gel (eluent:CH$_2$Cl$_2$/7N NH$_3$ in MeOH—10:1) to yield the product as a pale yellow solid (0.026 g; 75%).

$^1$H NMR (500 MHz, CD$_3$OD) δ 8.36 (s, 1H); 8.31-8.08 (m, 4H); 7.85 (d, J=8.64 Hz, 1H); 7.63 (d, J=8.64 Hz, 1H); 7.49-7.44 (m, 2H); 7.36-7.31 (m, 1H).

$^{13}$C NMR (126 MHz, CD$_3$OD) δ 150.2, 149.0, 147.1, 146.8, 138.6, 132.2, 129.7, 128.6, 128.1, 122.5, 120.3, 117.2.

HRMS (APCI): calcd. for C$_{16}$H$_{12}$N$_3$O [M+H]$^+$= 262.0975; found [M+H]$^+$=262.0976.

Preparative Example 10

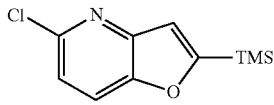 [SMILES: C[Si](C)(C)c1cc2nc(Cl)ccc2o1]

The product from Preparative Example 3 (4.5 g; 17.62 mmol) was placed into a 250 mL round bottom flask. TEA (32 mL) and 1,4-dioxane (32 mL) were added and the mixture was purged with N$_2$. Ethynyltrimethylsilane (2.25 g; 22.9 mmol), CuI (0.168 g; 0.881 mmol) and PdCl$_2$(PPh$_3$)$_2$ (0.247 mg, 0.352 mmol) were added and the mixture was stirred at 45° C. under N$_2$ for 2.5 h. The solvent was evaporated and the residue was purified by column chromatography (hexane/EtOAc; from 15:1 to 10:1) to yield the product as an orange solid (2.90 g; 73% yield).

$^1$H NMR (500 MHz, CDCl$_3$) δ 7.67 (dd, J=0.85 Hz, 8.56 Hz, 1H); 7.17 (d, J=8.56 Hz, 1H); 7.03 (d, J=0.84 Hz, 1H); 0.35 (m, 9H).

$^{13}$C NMR (126 MHz, CDCl$_3$) δ 170.8, 149.9, 148.5, 146.7, 120.7, 119.1, 116.8, −1.9.

HRMS (APCI): calcd. for C$_{10}$H$_{13}$ClNOSi [M+H]$^+$= 226.0449; found [M+H]$^+$=226.0446.

Preparative Example 11

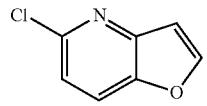

To a solution of the product from Preparative Example 10 (1.013 g; 4.49 mmol) in methanol (20 mL) was added KF (0.803 g; 13.82 mmol) and the resulting mixture was stirred under N$_2$ at 60° C. for 15 h. Then it was cooled to 25° C., poured into aqueous solution of HCl (0.1M; 100 mL) and extracted with EtOAc (3×60 mL). The organic extracts were dried over Na$_2$SO$_4$, filtered, and the solvent was evaporated. The residue was purified by column chromatography on silica gel (eluent:hexane/EtOAc—10:1) to yield the product as a pale yellow solid (0.579 g; 84%).

$^1$H NMR (500 MHz, CDCl$_3$) δ 7.84 (d, J=2.28 Hz, 1H); 7.70 (dd, J=0.84 Hz, 8.60 Hz, 1H); 7.21 (d, J=8.60 Hz, 1H); 6.90 (dd, J=0.84 Hz, 2.26 Hz, 1H).

$^{13}$C NMR (126 MHz, CDCl$_3$) δ 150.3, 147.6, 147.2, 146.9, 121.1, 119.5, 108.1.

HRMS (APCI): calcd. for C$_7$H$_5$ClNO [M+H]$^+$=154.0054; found [M+H]$^+$=154.0055.

Preparative Example 12A

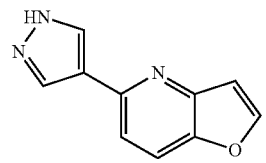 [SMILES: c1cc2nc(-c3cn[nH]c3)ccc2o1]

To a mixture of the product from Preparative Example 11 (0.201 g; 0.89 mmol), 1-Boc-pyrazole-4-boronic acid pinacol ester (0.0317 g; 1.07 mmol), K$_3$PO$_4$ (0.781 g; 3.68 mmol) and PdCl$_2$.dppf (0.039 g; 0.053 mmol) were added under N$_2$ 1,2-dimethoxyethane (4 mL) and water (1 mL). The reaction mixture was refluxed for 19 h. Then it was cooled to 25° C., diluted with EtOAc (20 mL), poured into brine (30 mL) and extracted with EtOAc (3×20 mL). The organic extracts were dried over Na$_2$SO$_4$, filtered and the solvent was evaporated. The residue was purified by column chromatography on silica gel (eluent:CH$_2$Cl$_2$/MeOH—15:1). So obtained solid was further purified by preparative TLC (eluent:CH$_2$Cl$_2$/MeOH—15:1) to yield the pale yellow crystalline product (0.080 g; 49%).

$^1$H NMR (500 MHz, CD$_3$OD) δ 8.17 (s, 2H); 8.04 (d, J=2.28 Hz, 1H); 7.89 (dd, J=0.83 Hz, 8.64 Hz, 1H); 7.62 (d, J=8.65 Hz, 1H); 6.96 (dd, J=0.85 Hz, 2.26 Hz, 1H); 4.86 (brs, 1H).

$^{13}$C NMR (126 MHz, CD$_3$OD) δ 151.4, 150.1, 148.2, 148.1, 133.4, 123.8, 120.9, 117.7, 108.2.

HRMS (APCI): calcd. for C$_{10}$H$_8$N$_3$O [M+H]$^+$=186.0662; found [M+H]$^+$=186.0659.

Preparative Example 12B

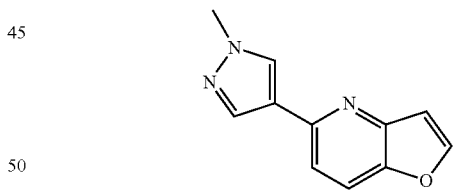

To a mixture of the product from Preparative Example 11 (0.052 g; 0.34 mmol), 1-methylpyrazole-4-boronic acid pinacol ester (0.092 g; 0.44 mmol), K$_3$PO$_4$ (0.308 g; 1.45 mmol) and PdCl$_2$.dppf (0.017 g; 0.023 mmol) were added under N$_2$ 1,2-dimethoxyethane (2 mL) and water (0.5 mL). The reaction mixture was refluxed for 14 h. Then it was cooled to 25° C., diluted with EtOAc (15 mL), poured into brine (25 mL) and extracted with EtOAc (3×15 mL). The organic extracts were dried over Na$_2$SO$_4$, filtered and the solvent was evaporated. The residue was purified by column chromatography on silica gel (eluent:CH$_2$Cl$_2$/MeOH—10:1) to yield the product as a brown solid (0.045 g; 66%).

$^1$H NMR (500 MHz, CDCl$_3$) δ 7.94 (s, 2H); 7.80 (d, J=2.21 Hz, 1H); 7.72 (d, J=8.53 Hz, 1H); 7.39 (d, J=8.59 Hz, 1H); 6.95 (d, J=1.64 Hz, 1H); 3.94 (s, 3H).

$^{13}$C NMR (126 MHz, CDCl$_3$) δ 149.3, 149.0, 147.5, 146.7, 137.7, 128.9, 124.1, 119.2, 116.0, 108.3, 39.4.

HRMS (APCI): calcd. for C$_{11}$H$_{10}$N$_3$O [M+H]$^+$=200.0818; found [M+H]$^+$=200.0817.

Preparative Example 13

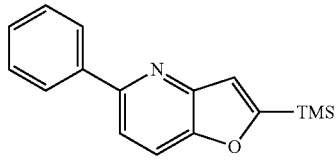 [SMILES: C[Si](C)(C)c1cc2nc(-c3ccccc3)ccc2o1]

To a mixture of the product from Preparative Example 10 (1.62 g; 7.16 mmol), phenylboronic acid (1.13 g; 9.26 mmol), triethylamine (10 mL; 71.8 mmol) and PdCl$_2$.dppf (0.160 g; 0.22 mmol) were added under N$_2$ 1,2-dimethoxyethane (12 mL) and water (3 mL). The reaction mixture was refluxed under N$_2$ for 20 h. Then it was cooled to 25° C., diluted with EtOAc (70 mL), poured into brine (90 mL) and extracted with EtOAc (3×70 mL). The organic extracts were dried over Na$_2$SO$_4$, filtered and the solvent was evaporated. The residue was purified by column chromatography on silica gel (eluent:hexane/EtOAc—15:1) to yield the product as a pale yellow solid (1.61 g; 84%).

$^1$H NMR (500 MHz, CDCl$_3$) δ 8.01-7.96 (m, 2H); 7.78 (dd, J=0.93 Hz, 8.61 Hz, 1H); 7.61 (d, J=8.62 Hz, 1H); 7.49-7.43 (m, 2H); 7.41-7.35 (m, 1H); 7.20 (d, J=0.81 Hz, 1H); 0.39-0.39 (m, 9H).

$^{13}$C NMR (126 MHz, CDCl$_3$) δ 169.5, 154.3, 150.3, 148.6, 140.3, 128.9, 128.6, 127.5, 118.7, 117.6, 116.9, −1.8.

HRMS (APCI): calcd. for C$_{16}$H$_{18}$NOSi [M+H]$^+$=268.1152; found [M+H]$^+$=268.1153.

Preparative Example 14

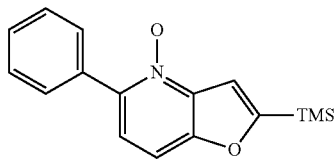

To a stirred solution of the product from Preparative Example 13 (1.61 g, 6.02 mmol) in anhydrous CH$_2$Cl$_2$ (20 ml) was added MCPBA (1.88 g, 10.9 mmol) and the resulting mixture was stirred under N$_2$ at 25° C. for 72 h. Then it was poured into saturated aqueous solution of NaHCO$_3$ (110 mL) and extracted with CH$_2$Cl$_2$ (3×60 mL). The organic extracts were washed with brine (50 mL), dried over Na$_2$SO$_4$, filtered and the solvent was evaporated. The residue was purified by column chromatography on silica gel (eluent:CH$_2$Cl$_2$/MeOH—12:1) to yield the product as a pale yellow solid (1.60 g; 94%).

$^1$H NMR (500 MHz, CDCl$_3$) δ 7.86-7.80 (m, 2H); 7.50-7.39 (m, 5H); 7.30 (d, J=8.58 Hz, 1H); 0.38-0.36 (m, 9H).

$^{13}$C NMR (126 MHz, CDCl$_3$) δ 169.0, 153.2, 144.7, 139.6, 133.1, 129.8, 129.4, 128.5, 122.2, 112.0, 110.4, −1.9.

HRMS (APCI): calcd. for C$_{16}$H$_{17}$NO$_2$Si [2M+H]$^+$=567.213; found [2M+H]$^+$=567.2134.

Preparative Example 15

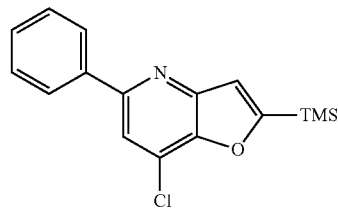 [SMILES: C[Si](C)(C)c1cc2nc(-c3ccccc3)cc(Cl)c2o1]

To a stirred solution of the product from Preparative Example 14 (0.575 g, 2.03 mmol) in CHCl$_3$ (10 ml) was added POCl$_3$ (3.4 mL; 36.5 mmol) and the resulting mixture was refluxed under N$_2$ for 1 h. Then, the CHCl$_3$ and POCl$_3$ were evaporated under reduced pressure. The dark oily residue was diluted with CH$_2$Cl$_2$ (50 mL), poured into saturated aqueous solution of NaHCO$_3$ (200 mL) and extracted with CH$_2$Cl$_2$ (3×70 mL). The organic extracts were washed with water (50 mL), brine (80 mL), dried over Na$_2$SO$_4$, filtered, and the solvent was evaporated. The residue was purified by column chromatography on silica gel (eluent:hexane/CH$_2$Cl$_2$—1:1) to yield the product as a colorless wax (0.339 g; 55%).

$^1$H NMR (500 MHz, CDCl$_3$) δ 7.99-7.94 (m, 2H); 7.63 (s, 1H); 7.49-7.44 (m, 2H); 7.42-7.37 (m, 1H); 7.20 (s, 1H); 0.41-0.38 (m, 9H).

$^{13}$C NMR (126 MHz, CDCl$_3$) δ 170.6, 155.4, 149.8, 146.8, 139.3, 129.1, 129.0, 127.4, 126.5, 118.1, 117.3, −1.8.

HRMS (APCI): calcd. for C$_{16}$H$_{16}$ClNOSi [M+H]$^+$=302.0762; found [M+H]$^+$=302.0764.

Preparative Example 16

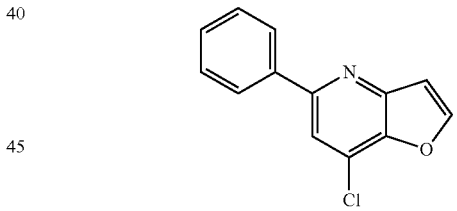

To a solution of the product from Preparative Example 15 (1.11 g; 3.68 mmol) in methanol (10 mL) was added KF (0.646 g; 11.1 mmol) and the resulting mixture was stirred under N$_2$ at 60° C. for 20 h. Then it was cooled to 25° C., poured into aqueous solution of HCl (0.1M; 40 mL) and extracted with EtOAc (3×30 mL). The organic extracts were washed with brine (30 mL), dried over Na$_2$SO$_4$, filtered and the solvent was evaporated. The residue was purified by column chromatography on silica gel (eluent:CH$_2$Cl$_2$/MeOH—20:1) to yield the product as a white solid (0.796 g; 94%).

$^1$H NMR (500 MHz, CDCl$_3$) δ 7.99-7.95 (m, 2H); 7.90 (d, J=2.18 Hz, 1H); 7.68 (s, 1H); 7.51-7.44 (m, 2H); 7.43-7.39 (m, 1H); 7.09 (d, J=2.15 Hz, 1H).

$^{13}$C NMR (126 MHz, CDCl$_3$) δ 155.8, 150.2, 148.8, 144.0, 138.8, 129.4, 129.1, 127.5, 127.0, 117.6, 109.2.

HRMS (APCI): calcd. for C$_{13}$H$_9$ClNO [M+H]$^+$=230.0367; found [M+H]$^+$=230.0365.

Preparative Example 17A

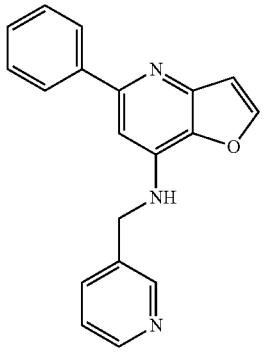 [SMILES: c1ccc(-c2cc(NCc3cccnc3)c3occc3n2)cc1]

To a solution of the product from Preparative Example 16 (0.103 g; 0.45 mmol), (R)-BINAP (0.016 g; 0.026 mmol), Pd(dba)$_2$ (0.017 g; 0.030 mmol) and t-BuOK (0.078 g; 0.69 mmol) in anhydrous toluene (3 mL) was added 3-picolylamine (0.050 mL; 0.49 mmol) and the resulting mixture was stirred under N$_2$ at 80° C. for 17 h. Then it was cooled to 25° C., diluted with EtOAc (10 mL), poured into water (25 mL) and extracted with EtOAc (3×10 mL). The organic extracts were washed with brine (15 mL), dried over MgSO$_4$, filtered, and the solvent was evaporated. The residue was purified by column chromatography on silica gel (eluent: CH$_2$Cl$_2$/MeOH—10:1) to yield the product as an orange foam (0.056 g; 42%).

$^1$H NMR (500 MHz, CDCl$_3$) δ 8.62 (d, J=59.05 Hz, 2H); 7.84 (d, J=7.29 Hz, 2H); 7.75-7.66 (m, 2H); 7.44-7.25 (m, 4H); 6.96 (d, J=2.02 Hz, 1H); 6.81 (s, 1H); 5.09 (brs, 1H); 4.63 (d, J=5.71 Hz, 2H).

$^{13}$C NMR (126 MHz, CDCl$_3$) δ 156.5, 149.5, 149.3, 147.5, 146.7, 140.8, 139.4, 136.8, 135.2, 133.7, 128.8, 128.6, 127.5, 124.0, 109.1, 99.6, 45.0.

HRMS (APCI): calcd. for C$_{19}$H$_{16}$N$_3$O [M+H]$^+$= 302.1288; found [M+H]$^+$=302.1285.

Preparative Example 17B

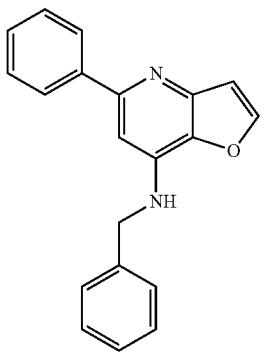 [SMILES: c1ccc(CNc2cc(-c3ccccc3)nc3ccoc23)cc1]

To a solution of the product from Preparative Example 16 (0.207 g; 0.90 mmol), (R)-BINAP (0.035 g; 0.056 mmol), Pd(dba)$_2$ (0.050 g; 0.087 mmol) and t-BuOK (0.146 g; 1.30 mmol) in anhydrous toluene (3 mL) was added benzylamine (0.120 mL; 1.10 mmol) and the resulting mixture was stirred under N$_2$ at 80° C. for 17 h. Then it was cooled to 25° C., diluted with EtOAc (10 mL), poured into water (25 mL) and extracted with EtOAc (3×10 mL). The organic extracts were washed with brine (15 mL), dried over MgSO$_4$, filtered and the solvent was evaporated. The residue was purified by column chromatography on silica gel (eluent:CH$_2$Cl$_2$/MeOH—15:1). So obtained solid was further purified by preparative TLC (eluent:CH$_2$Cl$_2$/MeOH—20:1) to yield the product as a brownish foam (0.233 g; 86%).

$^1$H NMR (500 MHz, CDCl$_3$) δ 7.90-7.85 (m, 2H); 7.69 (d, J=2.19 Hz, 1H); 7.44-7.28 (m, 8H); 6.95 (d, J=2.19 Hz, 1H); 6.85 (s, 1H); 4.96 (t, J=5.13 Hz, 1H); 4.59 (d, J=5.63 Hz, 2H).

$^{13}$C NMR (126 MHz, CDCl$_3$) δ 156.6, 147.2, 146.7, 141.2, 139.7, 138.1, 136.9, 129.1, 128.7, 128.4, 128.0, 127.7, 127.6, 109.2, 99.5, 47.4.

HRMS (APCI): calcd. for C$_{20}$H$_{17}$N$_2$O [M+H]$^+$= 301.1335; found [M+H]$^+$=301.1335.

Preparative Example 17C

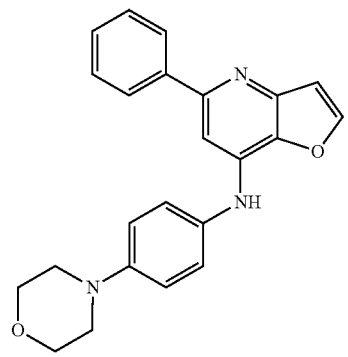 [SMILES: c1ccc(-c2cc(Nc3ccc(N4CCOCC4)cc3)c3occc3n2)cc1]

To a freshly prepared solution of xantphos (0.012 g; 0.021 mmol) and Pd$_3$(dba)$_2$ (0.022 g; to 0.024 mmol) in anhydrous 1,2-dimethoxyethane (2 mL) were added the product from Preparative Example 16 (0.049 g; 0.22 mmol), t-BuOK (0.052 g; 0.46 mmol) and 4-morpholinoaniline (0.048 g; 0.27 mmol) and the resulting mixture was stirred under N$_2$ at 100° C. for 16 h. Then it was cooled to 25° C., diluted with EtOAc (15 mL), poured into brine (25 mL) and extracted with EtOAc (3×15 mL). The organic extracts were dried over MgSO$_4$, filtered, and the solvent was evaporated. The residue was purified by column chromatography on silica gel (eluent:CH$_2$Cl$_2$/MeOH—15:1). So obtained oil was further purified by preparative TLC (eluent:CH$_2$Cl$_2$/MeOH—20:1) to yield the product as a brownish solid (0.018 g; 22%).

$^1$H NMR (500 MHz, CDCl$_3$) δ 7.86-7.83 (m, 2H); 7.74 (d, J=2.20 Hz, 1H); 7.42-7.37 (m, 2H); 7.36-7.31 (m, 1H); 7.26-7.21 (m, 2H); 7.15 (s, 1H); 6.99 (d, J=2.20 Hz, 1H); 6.97-6.93 (m, 2H); 6.34 (brs, 1H); 3.90-3.85 (m, 4H); 3.20-3.14 (m, 4H).

$^{13}$C NMR (126 MHz, CDCl$_3$) δ 156.3, 149.1, 147.5, 147.2, 140.9, 137.9, 137.0 131.4, 128.7, 128.5, 127.6, 1241, 116.9, 109.2, 100.3, 67.1, 49.8.

HRMS (APCI): calcd. for C$_{23}$H$_{22}$N$_3$O$_2$ [M+H]$^+$= 372.1707; found [M+H]$^+$=372.1707.

Preparative Examples 17D-17I

By essentially same procedure set forth in Preparative Example 17C, using proper amines instead of 4-morpholinoaniline, the compounds given below were prepared.

Preparative Example 17D

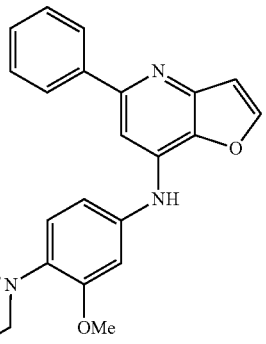

Brown semi-solid.

$^1$H NMR (500 MHz, CDCl$_3$) δ 7.87-7.83 (m, 2H); 7.74 (d, J=2.21 Hz, 1H); 7.42-7.37 (m, 2H); 7.35-7.31 (m, 1H); 7.25 (s, 1H); 6.98 (d, J=2.20 Hz, 1H); 6.95 (d, J=8.36 Hz, 1H); 6.87 (dd, J=2.33 Hz, 8.36 Hz, 1H); 6.83 (d, J=2.33 Hz, 1H); 6.38 (brs, 1H); 3.84 (s, 3H); 3.20-3.02 (m, 4H); 2.69-2.58 (m, 4H); 2.36 (s, 3H).

$^{13}$C NMR (126 MHz, CDCl$_3$) δ 156.4, 153.3, 147.6, 147.4, 140.9, 138.8, 137.4, 137.0, 134.4, 128.7, 128.5, 127.5, 119.2, 115.3, 109.3, 107.1, 100.6, 55.9, 55.6, 50.9, 46.3.

HRMS (APCI): calcd. for C$_{25}$H$_{27}$N$_4$O$_2$ [M+H]$^+$=415.2129; found [M+H]$^+$=415.2130.

Preparative Example 17E

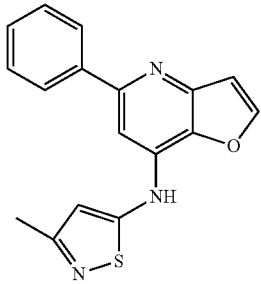 [SMILES: Cc1cc(Nc2cc(-c3ccccc3)nc3ccoc23)sn1]

Orange solid.

$^1$H NMR (500 MHz, DMSO-d$_6$) δ 8.36 (d, J=2.26 Hz, 1H); 8.01-7.97 (m, 2H); 7.93 (s, 1H); 7.61-7.50 (m, 3H); 7.48-7.43 (m, 1H); 7.38 (s, 1H); 7.21 (d, J=2.25 Hz, 1H); 2.33 (s, 3H).

$^{13}$C NMR (126 MHz, DMSO-d$_6$) δ 168.5, 153.3, 150.6, 146.5, 143.5, 138.8, 130.8, 128.7, 128.7, 126.6, 121.5, 110.7, 108.0, 53.7, 20.0.

HRMS (APCI): calcd. for C$_{17}$H$_{14}$N$_3$OS [M+H]$^+$=308.0852; found [M+H]$^+$=308.0850.

Preparative Example 17F

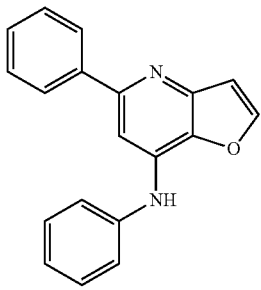 [SMILES: c1ccc(Nc2cc(-c3ccccc3)nc3ccoc23)cc1]

Pale yellow solid.

$^1$H NMR (500 MHz, CDCl$_3$) δ 7.89-7.86 (m, 2H); 7.76 (d, J=2.21 Hz, 1H); 7.44-7.29 (m, 8H); 7.18-7.14 (m, 1H); 7.00 (d, J=2.22 Hz, 1H); 6.48 (brs, 1H).

$^{13}$C NMR (126 MHz, CDCl$_3$) δ 156.4, 147.7, 147.6, 140.9, 139.5, 137.2, 136.4, 129.9, 128.8, 128.5, 127.5, 124.5, 121.8, 109.3, 101.0.

HRMS (APCI): calcd. for C$_{19}$H$_{15}$N$_2$O [M+H]$^+$=287.1179; found [M+H]$^+$=287.1178.

Preparative Example 17G

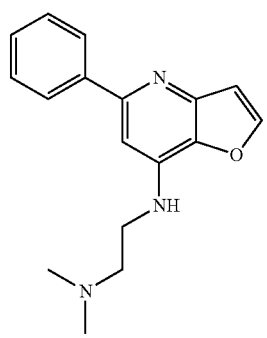 [SMILES: CN(C)CCNc1cc(-c2ccccc2)nc2ccoc12]

Orange semi-solid.

$^1$H NMR (500 MHz, CDCl$_3$) δ 7.95-7.90 (m, 2H); 7.69 (d, J=2.17 Hz, 1H); 7.46-7.40 (m, 2H); 7.38-7.33 (m, 1H); 6.94 (d, J=2.17 Hz, 1H); 6.81 (s, 1H); 5.36-5.23 (m, 1H); 3.43 (dd, J=5.19 Hz, 11.56 Hz, 2H); 2.69-2.62 (m, 2H); 2.30 (s, 6H).

$^{13}$C NMR (126 MHz, CDCl$_3$) δ 156.4, 147.1, 146.6, 141.3, 140.1, 137.0, 128.7, 128.4, 127.6, 109.0, 99.5, 57.8, 45.3, 40.2.

HRMS (APCI): calcd. for C$_{17}$H$_{20}$N$_3$O [M+H]$^+$=282.1601; found [M+H]$^+$=282.1602.

Preparative Example 17H

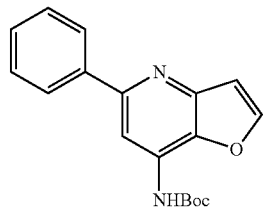 [SMILES: CC(C)(C)OC(=O)Nc1cc(-c2ccccc2)nc2ccoc12]

Pale yellow solid foam.

$^1$H NMR (500 MHz, CDCl$_3$) δ 8.41 (s, 1H); 8.03-7.98 (m, 2H); 7.76 (d, J=2.21 Hz, 1H); 7.46-7.42 (m, 2H); 7.39-7.35 (m, 1H); 7.15 (brs, 1H); 7.02 (d, J=2.21 Hz, 1H); 1.57 (s, 9H).

$^{13}$C NMR (126 MHz, CDCl$_3$) δ 156.5, 152.0, 148.1, 147.3, 140.3, 136.9, 131.4, 128.8, 128.8, 127.7, 109.4, 105.5, 82.4, 28.5.

HRMS (APCI): calcd. for C$_{18}$H$_{19}$N$_2$O$_3$ [M+H]$^+$=311.1390; found [M+H]$^+$=311.1394.

Preparative Example 17I

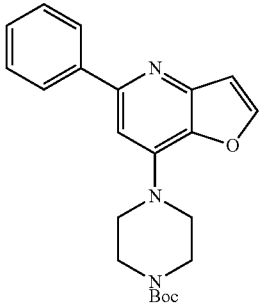 [SMILES: CC(C)(C)OC(=O)N1CCN(c2cc(-c3ccccc3)nc3ccoc23)CC1]

Orange wax.

¹H NMR (500 MHz, CDCl₃) δ 7.93-7.89 (m, 2H); 7.73 (d, J=2.22 Hz, 1H); 7.47-7.41 (m, 2H), 7.40-7.35 (m, 1H); 6.99 (d, J=1.60 Hz, 1H); 6.92 (s, 1H); 3.67-3.60 (m, 8H); 1.48 (s, 9H).

¹³C NMR (126 MHz, CDCl₃) δ 156.3, 154.9, 147.2, 142.3, 138.0, 128.8, 128.7, 127.6, 108.9, 102.9, 80.4, 48.1, 28.7.

HRMS (APCI): calcd. for $C_{22}H_{26}N_3O_3$ [M+H]⁺= 380.1969; found [M+H]⁺=380.1970.

Preparative Example 18A

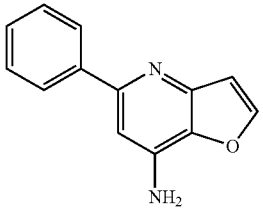 [SMILES: Nc1cc(-c2ccccc2)nc2ccoc12]

To a stirred solution of the product from Preparative Example 17H (0.031 g; 0.10 mmol) in ethanol (2 mL) was added aqueous solution of HCl (3M; 0.7 mL; 2.1 mmol) and the resulting mixture was stirred under N₂ at 60° C. for 18 h. Then the ethanol and HCl were evaporated and the oily residue was treated with CH₂Cl₂ (2 mL), MeOH (1 mL) and Na₂CO₃ (200 mg) and the mixture was stirred at 25° C. After 20 min., the solvents were evaporated and the solid residue was purified by preparative TLC (eluent:CH₂Cl₂/7N NH₃ in MeOH—50:1) to yield the product as a white solid (0.019 g; 88%).

¹H NMR (500 MHz, CDCl₃) δ 7.92-7.87 (m, 2H); 7.72 (d, J=2.20 Hz, 1H); 7.45-7.40 (m, 2H); 7.38-7.33 (m, 1H); 6.95 (d, J=2.20 Hz, 1H); 6.92 (s, 1H); 4.49 (brs, 2H).

¹³C NMR (126 MHz, CDCl₃) δ 156.1, 147.8, 147.5, 140.6, 138.5, 137.0, 128.8, 128.5, 127.5, 109.0, 103.2.

HRMS (APCI): calcd. for $C_{13}H_{11}N_2O$ [M+H]⁺= 211.0866; found [M+H]⁺=211.0866.

Preparative Example 18B

By essentially same procedure set forth in Preparative Example 18A, using the product from Preparative Example 17I, the compound given below was prepared.

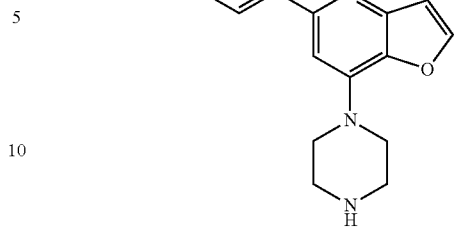

Pale yellow semi-solid.

¹H NMR (500 MHz, CDCl₃) δ 7.93-7.89 (m, 2H); 7.71 (d, J=2.21 Hz, 1H); 7.46-7.40 (m, 2H); 7.38-7.34 (m, 1H); 6.96 (d, J=2.22 Hz, 1H); 6.92 (s, 1H); 3.65-3.60 (m, 4H); 3.13-3.04 (m, 4H).

¹³C NMR (126 MHz, CDCl₃) δ 156.4, 148.4, 146.9, 142.7, 141.0, 138.2, 128.8, 128.5, 127.6, 108.9, 102.8, 49.2, 46.0.

HRMS (APCI): calcd. for $C_{17}H_{18}N_3O$ [M+H]⁺= 280.1444; found [M+H]⁺=280.1443.

Preparative Example 19A

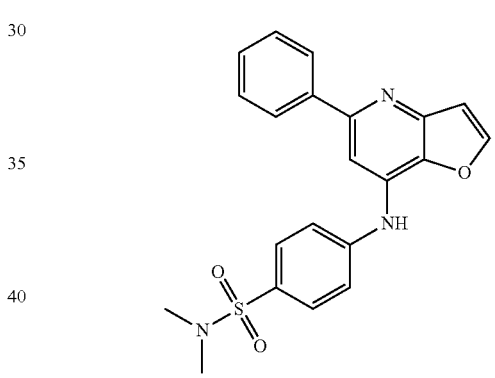

To a freshly prepared solution of (S)-1-[(R$_P$)-2-(dicyclohexylphosphino)ferrocenyl]ethyldi-tert-butylphosphine (0.012 g; 0.022 mmol) and Pd(OAc)₂ (0.008 g; 0.037 mmol) in anhydrous 1,2-dimethoxyethane (2 mL) were added the product from Preparative Example 16 (0.049 g; 0.21 mmol), t-BuOK (0.038 g; 0.34 mmol) and 4-amino-N,N-dimethylbenzenesulfonamide (0.051 g; 0.25 mmol) and the resulting mixture was stirred under N₂ at 100° C. for 16 h. Then it was diluted with EtOAc (15 mL), poured into brine (25 mL) and extracted with EtOAc (3×15 mL). The organic extracts were dried over MgSO₄, filtered and the solvent was evaporated. The residue was purified by column chromatography on silica gel (eluent:CH₂Cl₂/MeOH—15:1). So obtained oil was further purified by preparative TLC (eluent:CH₂Cl₂/MeOH—20:1) to yield the yellow semi solid product (0.036 g; 43%).

¹H NMR (500 MHz, CDCl₃) δ 7.90-7.86 (m, 2H); 7.78-7.71 (m, 3H); 7.49 (s, 1H); 7.45-7.32 (m, 5H); 7.03 (brs, 1H); 7.00 (d, J=2.15 Hz, 1H); 2.72 (s, 6H).

¹³C NMR (126 MHz, CDCl₃) δ 156.4, 148.3, 148.3, 144.5, 140.3, 137.6, 134.1, 129.8, 129.2, 128.9, 128.9, 127.5, 118.8, 109.2, 103.2, 38.2.

HRMS (APCI): calcd. for C₂₁H₂₀N₃O₃S [M+H]⁺= 394.1220; found [M+H]⁺=394.1217.

Preparative Example 19B

By essentially same procedure set forth in Preparative Example 19A, using cyclohexylamine instead of 4-amino-N,N-dimethyl-benzenesulfonamide, the compound given below was prepared.

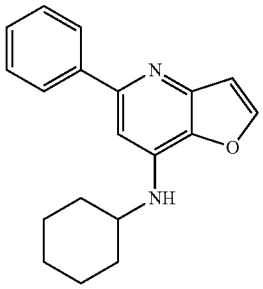 [SMILES: c1ccc(-c2cc(NC3CCCCC3)c3occc3n2)cc1]

Yellow wax.

¹H NMR (500 MHz, CDCl₃) δ 7.92-7.87 (m, 2H); 7.66 (d, J=2.17 Hz, 1H); 7.45-7.39 (m, 2H); 7.38-7.32 (m, 1H); 6.96 (d, J=2.17 Hz, 1H); 6.81 (s, 1H); 4.70 (brs, 1H); 3.65-3.52 (m, 1H); 2.16-2.05 (m, 2H); 1.84-1.75 (m, 2H); 1.71-1.62 (m, 1H); 1.48-1.36 (m, 2H); 1.35-1.19 (m, 4H).

¹³C NMR (126 MHz, CDCl₃) δ 156.0, 147.1, 146.0, 140.8, 139.4, 136.7, 128.7, 128.5, 127.6, 108.8, 99.5, 51.5, 33.4, 25.8, 25.0.

HRMS (APCI): calcd. for C₁₉H₂₁N₂O [M+H]⁺= 293.1648; found [M+H]⁺=293.1647.

Preparative Example 19C

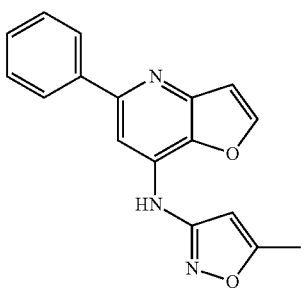 [SMILES: Cc1cc(Nc2cc(-c3ccccc3)nc3ccoc23)no1]

Degassed 1,2-dimethoxyethane (2.5 mL) was added under N₂ into a 10 mL round bottom flask containing Pd₂(dba)₃ (15.9 mg, 0.017 mmol) and SPhos (7.1 mg, 0.017 mmol). After 5 min, the product from Preparative Example 16 (40 mg, 0.17 mmol), 5-methylisoxazol-3-amine (20 mg, 0.212 mmol) and Cs₂CO₃ (125 mg, 0.383 mmol) were added. The mixture was stirred at 80° C. under N₂ for 24 h, then the temperature was elevated to 120° C. and the mixture was stirred for additional 24 h. H₂O (15 mL) was added and the mixture was extracted with EtOAc (3×25 mL). The organic phase was dried over Na₂SO₄, filtered, and then the solvent was evaporated. The residue was purified by column chromatography (CH₂Cl₂/EtOAc; 2:1) and then by preparative TLC (CH₂Cl₂/EtOAc; 2:1). The product was obtained as a colorless wax (14 mg, 30% yield).

¹H NMR (300 MHz, CDCl₃) δ 8.21 (s, 1H), 8.03 (d, J=7.9 Hz, 2H), 7.77 (d, J=1.7 Hz, 1H), 7.54-7.34 (m, 3H), 7.09-6.96 (m, 2H), 5.92 (s, 1H), 2.42 (s, 3H).

¹³C NMR (126 MHz, CDCl₃) δ 169.4, 159.5, 156.4, 147.6, 146.7, 140.0, 136.4, 132.8, 128.5, 128.4, 127.3, 109.0, 104.3, 94.8, 12.4.

HRMS (APCI): calcd. for C₁₇H₁₃N₃O₂ [M+H]⁺= 292.1081; found [M+H]⁺=292.1082.

Preparative Example 19D

By essentially same procedure set forth in Preparative Example 19C, using isoxazol-3-amine instead of 5-methyl-isoxazol-3-amine, the compound given below was prepared.

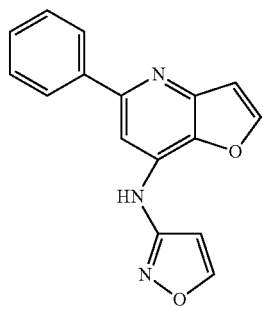 [SMILES: c1ccc(-c2cc(Nc3ccon3)c3occc3n2)cc1]

Colorless wax.

¹H NMR (500 MHz, CDCl₃) δ 8.30 (d, J=1.7 Hz, 1H), 8.28 (s, 1H), 8.07-8.01 (m, 2H), 7.78 (d, J=2.2 Hz, 1H), 7.52-7.44 (m, 2H), 7.44-7.37 (m, 1H), 7.14 (s, 1H), 7.04 (d, J=2.2 Hz, 1H), 6.28 (d, J=1.7 Hz, 1H).

¹³C NMR (126 MHz, CDCl₃) δ 158.2, 157.6, 155.8, 146.8, 146.1, 139.3, 135.6, 131.8, 127.7, 127.7, 126.6, 108.3, 103.7, 97.0.

HRMS (APCI): calcd. for C₁₆H₁₁N₃O₂ [M+H]⁺= 278.0924; found [M+H]⁺=278.0926.

Preparative Example 19E

By essentially same procedure set forth in Preparative Example 19C, using pyridin-3-amine instead of 5-methyl-isoxazol-3-amine, the compound given below was prepared.

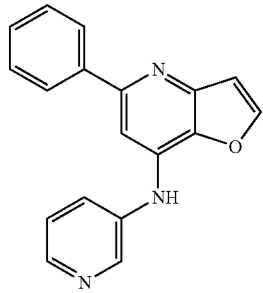 [SMILES: c1ccc(-c2cc(Nc3cccnc3)c3occc3n2)cc1]

Colorless wax.

¹H NMR (300 MHz, CDCl₃) δ 8.65 (s, 1H), 8.42 (d, J=4.2 Hz, 1H), 7.93-7.84 (m, 2H), 7.78 (d, J=2.2 Hz, 1H), 7.71-7.62 (m, 1H), 7.46-7.31 (m, 5H), 7.02 (d, J=2.2 Hz, 1H), 6.66 (s, 1H).

¹³C NMR (126 MHz, CDCl₃) δ 156.4, 148.0, 147.9, 145.3, 143.5, 140.4, 137.1, 136.4, 135.5, 128.7, 128.6, 128.2, 127.4, 124.1, 109.2, 101.1.

HRMS (APCI): calcd. for $C_{18}H_{13}N_3O$ [M+H]$^+$= 288.1131; found [M+H]$^+$=288.1132.

Preparative Example 19E

By essentially same procedure set forth in Preparative Example 19C, using 1-methyl-1H-pyrazol-4-amine instead of 5-methylisoxazol-3-amine, the compound given below was prepared.

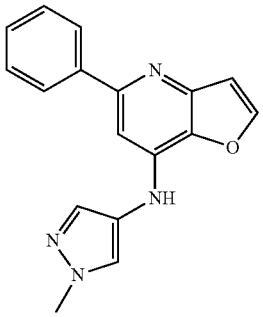 [SMILES: Cn1cc(Nc2cc(-c3ccccc3)nc3ccoc23)cn1]

Yellow wax.

$^1$H NMR (500 MHz, CDCl$_3$) δ 7.89-7.84 (m, 2H), 7.75 (d, J=2.2 Hz, 1H), 7.55 (s, 1H), 7.46-7.39 (m, 3H), 7.38-7.34 (m, 1H), 6.99 (d, J=2.2 Hz, 1H), 6.98 (s, 1H), 6.00 (s, 1H), 3.94 (s, 3H).

$^{13}$C NMR (126 MHz, CDCl$_3$) δ 156.4, 147.5, 146.9, 140.8, 138.8, 136.6, 136.1, 128.6, 128.4, 127.4, 125.9, 121.4, 109.0, 100.0, 39.7.

HRMS (APCI): calcd. for $C_{17}H_{14}N_4O$ [M+H]$^+$= 291.1240; found [M+H]$^+$=291.1237.

Preparative Example 20

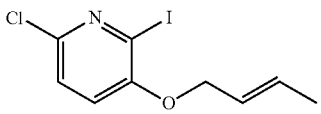

To a mixture of the product from Preparative Example 3 (4.34 g; 17.0 mmol) and K$_2$CO$_3$ (7.07 g; 51.1 mmol) in N,N-dimethylformamide (30 mL) was added under N$_2$ crotyl bromide (2.6 mL; 25.3 mmol). The resulting reaction mixture was stirred under N$_2$ at 60° C. for 2 h. Then the solvent was evaporated and the residue was suspended between H$_2$O (120 mL) and CH$_2$Cl$_2$ (90 mL). The water phase was extracted with CH$_2$Cl$_2$ (3×100 mL). The organic extracts were washed with brine (100 mL), dried over Na$_2$SO$_4$, filtered and the solvent was evaporated. The residue was purified by column chromatography on silica gel (eluent:hexane/EtOAc—1:1). So obtained pale yellow solid was washed with cold pentane (3×25 mL) to yield the white crystalline product (4.24 g; 81%).

$^1$H NMR (500 MHz, CDCl$_3$) δ 7.19-7.11 (m, 1H); 6.93 (d, J=8.46 Hz, 1H); 5.93-5.83 (m, 1H); 5.71-5.61 (m, 1H); 4.52 (d, J=5.49 Hz, 2H); 1.75 (d, J=6.42 Hz, 3H).

$^{13}$C NMR (126 MHz, CDCl$_3$) δ 154.4, 141.6, 131.7, 124.7, 123.7, 121.3, 110.0, 70.8, 18.1.

HRMS (APCI): calcd. for $C_9H_{10}ClINO$ [M+H]$^+$= 309.9490; found [M+H]$^+$=309.9488.

Preparative Example 21

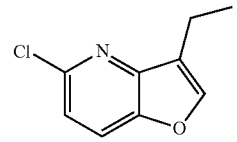

The mixture of the product from Preparative Example 20 (4.24 g; 13.7 mmol), K$_2$CO$_3$ (4.75 g; 34.4 mmol), HCOONa (0.934 g; 13.7 mmol); tetrabutylammonium chloride (4.21 g; 15.1 mmol) and Pd(OAc)$_2$ (0.185 g; 0.82 mmol) in N,N-dimethylformamide (30 mL) was stirred under N$_2$ at 80° C. for 3 h. Then the solvent was evaporated and the residue was suspended between H$_2$O (180 mL) and CH$_2$Cl$_2$ (100 mL). The aqueous phase was extracted with CH$_2$Cl$_2$ (3×100 mL). The organic extracts were washed with brine (100 mL), dried over Na$_2$SO$_4$, filtered and the solvent was evaporated. The residue was purified by column chromatography on silica gel (eluent:hexane/EtOAc—30:1) to yield the product as a pale yellow solid (0.774 g; 31%).

$^1$H NMR (500 MHz, CDCl$_3$) δ 7.66-7.62 (m, 2H); 7.19 (d, J=8.55 Hz, 1H); 2.76 (dq, J=1.23 Hz, 7.51 Hz, 2H); 1.33 (t, J=7.52 Hz, 3H).

$^{13}$C NMR (126 MHz, CDCl$_3$) δ 147.8, 147.4, 146.6, 146.2, 123.6, 120.9, 119.2, 16.0, 13.5.

HRMS (APCI): calcd. for $C_9H_9ClNO$ [M+H]$^+$=182.0367; found [M+H]$^+$=182.0365.

Preparative Example 22

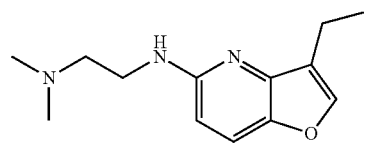 [SMILES: CCc1coc2ccc(NCCN(C)C)nc12]

To a freshly prepared solution of (S)-1-[(R$_P$)-2-(dicyclohexylphosphino)ferrocenyl]ethyldi-tert-butylphosphine (0.022 g; 0.039 mmol) and Pd(OAc)$_2$ (0.009 g; 0.039 mmol) in anhydrous 1,2-dimethoxyethane (2 mL) were added the product from Preparative Example (0.087 g; 0.48 mmol), t-BuONa (0.064 g; 0.66 mmol) and N,N-dimethylethylenediamine (0.063 mL; 0.57 mmol) and the resulting mixture was stirred under N$_2$ at 100° C. for 15 h. Then it was cooled to 25° C., diluted with EtOAc (15 mL), poured into brine (25 mL) and extracted with EtOAc (3×15 mL). The organic extracts were dried over MgSO$_4$, filtered and the solvent was evaporated. The residue was purified by column chromatography on silica gel (eluent:CH$_2$Cl$_2$/7N NH$_3$ in MeOH—15:1) to yield the product as an orange oil (0.081 g; 73%).

$^1$H NMR (500 MHz, CDCl$_3$) δ 7.46-7.41 (m, 2H); 6.32 (d, J=8.87 Hz, 1H); 5.00-4.89 (m, 1H); 3.42 (dd, J=5.69 Hz, 11.45 Hz, 2H); 2.68 (dq, J=1.14 Hz, 7.51 Hz, 2H); 2.58 (t, J=6.06 Hz, 2H); 2.28 (s, 6H); 1.31 (t, J=7.51 Hz, 3H).

$^{13}$C NMR (126 MHz, CDCl$_3$) δ 156.7, 145.3, 143.7, 143.2, 123.0, 120.4, 104.5, 58.6, 45.5, 40.2, 16.2, 13.5.

HRMS (APCI): calcd. for $C_{13}H_{20}N_3O$ [M+H]$^+$= 234.1601; found [M+H]$^+$=234.1601.

Preparative Example 23

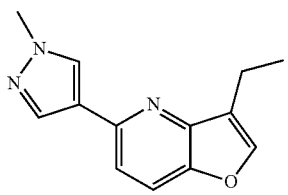 [SMILES: CCc1coc2ccc(-c3cnn(C)c3)nc12]

To a mixture of the product from Preparative Example 21 (0.053 g; 0.29 mmol), 1-methylpyrazole-4-boronic acid pinacol ester (0.074 g; 0.36 mmol), $K_3PO_4$ (0.262 g; 1.23 mmol) and $PdCl_2$.dppf (0.013 g; 0.017 mmol) were added under $N_2$ 1,2-dimethoxyethane (2 mL) and water (0.5 mL). The reaction mixture was refluxed for 19 h. Then it was cooled to 25° C., diluted with EtOAc (15 mL), poured into brine (25 mL) and extracted with EtOAc (3×15 mL). The organic extracts were dried over $Na_2SO_4$, filtered and the solvent was evaporated. The residue was purified by column chromatography on silica gel (eluent:$CH_2Cl_2$/MeOH—10:1) to yield the product as a brown semi-solid (0.055 g; 83%).

$^1$H NMR (500 MHz, $CDCl_3$) δ 8.04-7.91 (m, 2H); 7.64 (d, J=8.49 Hz, 1H); 7.58 (s, 1H); 7.36 (d, J=8.51 Hz, 1H); 3.94 (s, 3H); 2.81 (q, J=7.35 Hz, 2H); 1.37 (t, J=7.49 Hz, 3H).

$^{13}$C NMR (126 MHz, $CDCl_3$) δ 148.1, 147.5, 147.1, 145.1, 137.7, 129.0, 124.3, 123.7, 118.9, 115.7, 39.3, 16.2, 13.5.

HRMS (APCI): calcd. for $C_{13}H_{14}N_3O$ [M+H]$^+$= 228.1131; found [M+H]$^+$=228.1133.

Preparative Example 24

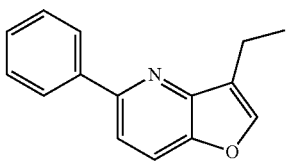 [SMILES: CCc1coc2ccc(-c3ccccc3)nc12]

To a mixture of the product from Preparative Example 21 (1.43 g; 7.85 mmol), phenylboronic acid (1.24 g; 10.2 mmol), $K_3PO_4$ (6.86 g; 32.3 mmol) and $PdCl_2$.dppf (0.530 g; 0.72 mmol) were added under $N_2$ 1,2-dimethoxyethane (50 mL) and water (10 mL). The reaction mixture was refluxed under $N_2$ for 18 h. Then it was cooled to 25° C., diluted with EtOAc (70 mL), poured into brine (100 mL) and extracted with EtOAc (3×70 mL). The organic extracts were dried over $Na_2SO_4$, filtered and the solvent was evaporated. The residue was purified by column chromatography on silica gel (eluent:hexane/EtOAc—15:1) to yield the product as a pale yellow solid (1.59 g; 91%).

$^1$H NMR (500 MHz, $CDCl_3$) δ 8.04 (d, J=7.51 Hz, 2H); 7.73 (d, J=8.54 Hz, 1H); 7.63 (d, J=8.51 Hz, 2H); 7.51-7.43 (m, 2H); 7.42-7.35 (m, 1H); 2.86 (q, J=7.48 Hz, 2H); 1.41 (t, J=7.37 Hz, 3H).

$^{13}$C NMR (126 MHz, $CDCl_3$) δ 153.8, 147.9, 147.7, 145.2, 140.4, 128.9, 128.6, 127.4, 124.1, 118.7, 116.6, 16.2, 13.6.

HRMS (APCI): calcd. for $C_{15}H_{14}NO$ [M+H]$^+$=224.107; found [M+H]$^+$=224.1068.

Preparative Example 25

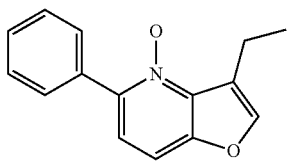

To a stirred solution of the product from Preparative Example 24 (1.59 g, 7.12 mmol) in anhydrous $CH_2Cl_2$ (20 ml) was added MCPBA (2.22 g, 12.9 mmol) and the resulting mixture was stirred under $N_2$ at 25° C. for 72 h. Then it was poured into saturated aqueous solution of $NaHCO_3$ (150 mL) and extracted with $CH_2Cl_2$ (3×80 mL). The organic extracts were washed with brine (80 mL), dried over $Na_2SO_4$, filtered, and the solvent was evaporated. The residue was purified by column chromatography on silica gel (eluent:$CH_2Cl_2$/EtOAc—5:1) to yield the product as a pale yellow solid (0.545 g; 32%).

$^1$H NMR (500 MHz, $CDCl_3$) δ 7.83-7.76 (m, 2H); 7.50-7.35 (m, 5H); 7.27 (d, J=8.60 Hz, 1H); 3.07 (q, J=7.37 Hz, 2H); 1.34 (t, J=7.41, 3H).

$^{13}$C NMR (126 MHz, $CDCl_3$) δ 151.0, 145.4, 144.0, 137.7, 133.1, 129.9, 129.3, 128.4, 122.2, 110.4, 18.1, 14.9.

HRMS (APCI): calcd. for $C_{15}H_{14}NO_2$ [M+H]$^+$= 240.1019; found [M+H]$^+$=240.1017.

Preparative Example 26

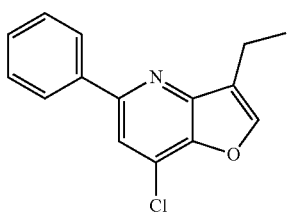 [SMILES: CCc1coc2c(Cl)cc(-c3ccccc3)nc12]

To a stirred solution of the product from Preparative Example 25 (0.713 g, 2.98 mmol) in $CHCl_3$ (15 ml) was added $POCl_3$ (6 mL, 64.4 mmol) and the resulting mixture was refluxed under $N_2$ for 1 hr. Then, the $CHCl_3$ and $POCl_3$ were evaporated under reduced pressure. The dark oily residue was diluted with $CH_2Cl_2$ (50 mL), poured into saturated aqueous solution of $NaHCO_3$ (200 mL) and extracted with $CH_2Cl_2$ (3×50 mL). The organic extracts were washed with water (50 mL), with brine (80 mL), dried over $Na_2SO_4$, filtered and the solvent was evaporated. The residue was purified by column chromatography on silica gel (eluent:hexane/$CH_2Cl_2$—2:1) to yield the product as a white solid (0.282 g; 37%).

$^1$H NMR (500 MHz, $CDCl_3$) δ 8.07-7.98 (m, 2H); 7.69-7.64 (m, 2H); 7.52-7.36 (m, 3H); 2.84 (dd, J=6.89 Hz, 14.36 Hz, 2H); 1.45-1.39 (m, 3H).

$^{13}$C NMR (126 MHz, $CDCl_3$) δ 155.0, 149.1, 145.8, 144.2, 139.3, 129.1, 129.0, 127.4, 126.3, 124.8, 117.1, 16.3, 13.5.

HRMS (APCI): calcd. for $C_{15}H_{13}ClNO$ [M+H]$^+$= 258.0680; found [M+H]$^+$=258.0678.

Preparative Example 27A

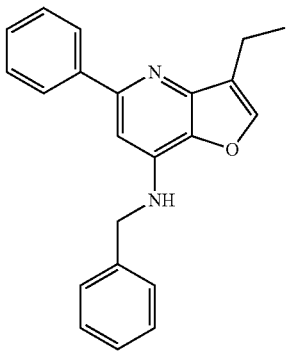

To a solution of the product from Preparative Example 26 (0.202 g; 0.78 mmol), (R)-BINAP (0.032 g; 0.052 mmol), Pd$_2$(dba)$_3$ (0.044 g; 0.048 mmol) and t-BuOK (0.146 g; 1.30 mmol) in anhydrous toluene (4 mL) was added benzylamine (0.100 mL; 0.92 mmol) and the resulting mixture was stirred under N$_2$ at 80° C. for 17 h. Then it was cooled to 25° C., diluted with EtOAc (10 mL), poured into water (25 mL) and extracted with EtOAc (3×10 mL). The organic extracts were washed with brine (15 mL), dried over MgSO$_4$, filtered and the solvent was evaporated. The residue was purified by column chromatography on silica gel (eluent:CH$_2$Cl$_2$/MeOH—20:1) to yield a brownish solid (0.168 g; 65%).

$^1$H NMR (500 MHz, CDCl$_3$) δ 7.94-7.89 (m, 2H); 7.49-7.46 (m, 1H); 7.43-7.27 (m, 8H); 6.85 (s, 1H); 4.89 (brs, 1H); 4.58 (d, J=5.67 Hz, 2H); 2.83 (dd, J=1.08 Hz, 7.49 Hz, 2H); 1.38 (t, J=7.51 Hz, 3H).

$^{13}$C NMR (126 MHz, CDCl$_3$) δ 155.7, 146.6, 143.1, 141.4, 139.6, 138.3, 137.2, 129.1, 128.7, 128.3, 128.0, 127.7, 127.6, 124.6, 99.3, 47.4, 16.4, 13.6.

HRMS (APCI): calcd. for C$_{22}$H$_{21}$N$_2$O [M+H]$^+$= 329.1648; found [M+H]$^+$=329.1650.

Preparative Example 27B

By essentially same procedure set forth in Preparative Example 27A, using N,N-dimethylethylenediamine instead of benzylamine, the compound given below was prepared.

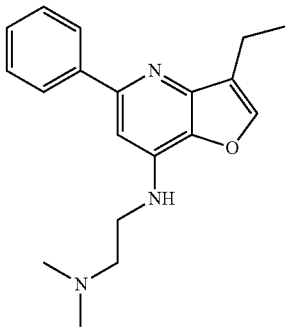 [SMILES: CCc1coc2c(NCCN(C)C)cc(-c3ccccc3)nc12]

Yellow wax.

$^1$H NMR (500 MHz, CDCl$_3$) δ 7.99-7.95 (m, 2H); 7.48-7.46 (m, 1H); 7.45-7.40 (m, 2H); 7.37-7.32 (m, 1H); 6.81 (s, 1H); 5.19-5.11 (m, 1H); 3.41 (dd, J=5.16 Hz, 11.70 Hz, 2H); 2.82 (qd, J=1.20 Hz, 7.50 Hz, 2H); 2.66-2.59 (m, 2H); 2.28 (s, 6H); 1.38 (t, J=7.51 Hz, 3H).

$^{13}$C NMR (126 MHz, CDCl$_3$) δ 155.6, 146.7, 142.9, 141.6, 139.9, 137.3, 128.7, 128.2, 127.6, 124.5, 99.3, 57.9, 45.4, 40.3, 16.4, 13.6.

HRMS (APCI): calcd. for C$_{19}$H$_{24}$N$_3$O [M+H]$^+$= 310.1914; found [M+H]$^+$=310.1915.

Preparative Example 28

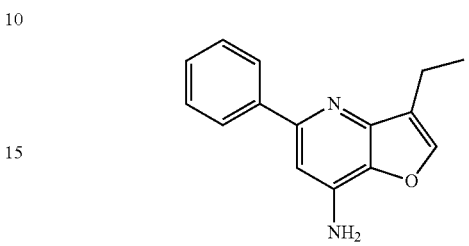

To a stirred solution of the product from Preparative Example 27A (0.052 g, 0.16 mmol) in hot EtOH (2 ml) were added Pd(OH)$_2$ (37 mg) and ammonium formate (0.059 g; 0.94 mmol) and the resulting mixture was refluxed under N$_2$ for 42 h. Then it was cooled to 25° C., filtered, and the solvent was evaporated. The residue was purified by preparative TLC (eluent:CH$_2$Cl$_2$/NH$_3$ in MeOH—50:1) to yield the product as a white solid (0.012 g; 32%).

$^1$H NMR (500 MHz, CDCl$_3$) δ 7.96 (d, J=7.43 Hz, 2H); 7.50 (s, 1H); 7.46-7.39 (m, 2H); 7.38-7.31 (m, 1H); 6.92 (s, 1H); 4.36 (brs, 2H); 2.82 (q, J=7.26 Hz, 2H); 1.38 (t, J=7.45 Hz, 3H).

$^{13}$C NMR (126 MHz, CDCl$_3$) δ 155.3, 147.7, 143.6, 140.9, 138.1, 137.4, 128.7, 128.3, 127.4, 124.5, 103.0, 16.4, 13.6.

HRMS (APCI): calcd. for C$_{15}$H$_{15}$N$_2$O [M+H]$^+$= 239.1179; found [M+H]$^+$=239.1179.

Preparative Example 29

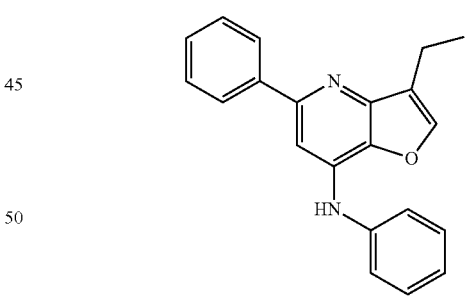

To a freshly prepared solution of xantphos (0.022 g; 0.038 mmol) and Pd$_3$(dba)$_2$ (0.042 g; 0.046 mmol) in anhydrous 1,2-dimethoxyethane (2 mL) were added the product from Preparative Example 26 (0.104 g; 0.40 mmol), t-BuOK (0.097 g; 0.86 mmol) and aniline (0.048 mL; 0.53 mmol) and the resulting mixture was stirred under N$_2$ at 100° C. for 16 h. Then it was cooled to 25° C., diluted with EtOAc (15 mL), poured into brine (25 mL) and extracted with EtOAc (3×15 mL). The organic extracts were dried over MgSO$_4$, filtered and the solvent was evaporated. The residue was purified by column chromatography on silica gel (eluent: hexane/EtOAc—15:1) to yield the product as a pale solid (0.064 g; 51%).

¹H NMR (500 MHz, CDCl₃) δ 7.96-7.91 (m, 2H); 7.56-7.53 (m, 1H); 7.45-7.27 (m, 8H); 7.17-7.12 (m, 1H); 6.40 (brs, 1H); 2.86 (qd, J=1.15 Hz, 7.50 Hz, 2H); 1.41 (t, J=7.51 Hz, 3H).

¹³C NMR (126 MHz, CDCl₃) δ 155.5, 147.7, 143.5, 141.1, 139.8, 137.6, 136.1, 129.9, 128.7, 128.4, 127.6, 124.8, 124.2, 121.5, 100.9, 16.4, 13.6.

HRMS (APCI): calcd. for $C_{21}H_{19}N_2O$ [M+H]⁺=315.1492; found [M+H]⁺=315.1492.

Preparative Example 30

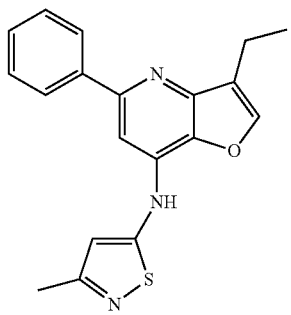 [SMILES: CCc1coc2c(Nc3cc(C)ns3)cc(-c3ccccc3)nc12]

To a freshly prepared solution of xantphos (0.023 g; 0.039 mmol) and Pd₃(dba)₂ (0.036 g; 0.039 mmol) in anhydrous 1,2-dimethoxyethane (2 mL) were added the product from Preparative Example 26 (0.104 g; 0.40 mmol), t-BuOK (0.158 g; 1.40 mmol) and 5-amino-3-methyl-isothiazole hydrochloride (0.115 g; 0.76 mmol) and the resulting mixture was stirred under N₂ at 100° C. for 22 h. Then it was cooled to 25° C., diluted with EtOAc (15 mL), poured into brine (25 mL) and extracted with EtOAc (3×15 mL). The organic extracts were dried over MgSO₄, filtered, and the solvent was evaporated. The residue was purified by column chromatography on silica gel (eluent:CH₂Cl₂/MeOH—20:1). So obtained oil was further purified by preparative TLC (eluent:CH₂Cl₂/MeOH—30:1) to yield the product as a pale orange solid (0.053 g; 39%).

¹H NMR (500 MHz, DMSO-d6) δ 8.15-8.12 (m, 1H); 8.03-7.98 (m, 2H); 7.94-7.88 (m, 1H); 7.56-7.50 (m, 3H); 7.47-7.43 (m, 1H); 7.37 (s, 1H); 2.77 (qd, J=1.05 Hz, 7.48 Hz, 2H); 2.32 (s, 3H); 1.35 (t, J=7.51 Hz, 3H).

¹³C NMR (126 MHz, DMSO-d6) δ 168.4, 152.7, 146.4, 146.0, 143.9, 138.9, 130.6, 128.7, 128.6, 126.6, 122.8, 121.5, 110.6, 53.9, 20.0, 15.5, 13.3.

HRMS (APCI): calcd. for $C_{19}H_{18}N_3OS$ [M+H]⁺=336.1165; found [M+H]⁺=336.1164.

Preparative Example 31A

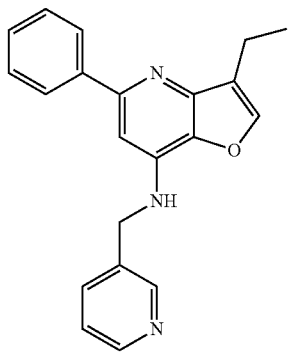 [SMILES: CCc1coc2c(NCc3cccnc3)cc(-c3ccccc3)nc12]

To a freshly prepared solution (S)-1-[(R$_P$)-2-(dicyclohexylphosphino)ferrocenyl]ethyldi-tert-butylphosphine (0.011 g; 0.021 mmol) and Pd(OAc)₂ (0.006 g; 0.028 mmol) in anhydrous 1,2-dimethoxyethane (2 mL) were added the product from Preparative Example 26 (0.109 g; 0.42 mmol), t-BuONa (0.060 g; 0.62 mmol) and 3-picolylamine (0.045 mL; 0.44 mmol) and the resulting mixture was stirred under N₂ at 100° C. for 17 h. Then it was cooled to 25° C., diluted with EtOAc (15 mL), poured into brine (25 mL) and extracted with EtOAc (3×15 mL). The organic extracts were dried over MgSO₄, filtered and the solvent was evaporated. The residue was purified by column chromatography on silica gel (eluent:CH₂Cl₂/MeOH—10:1). So obtained oil was further purified by preparative TLC (eluent:CH₂Cl₂/NH₃ in MeOH—30:1) to yield the product as a pale yellow solid (0.081 g; 58%).

¹H NMR (500 MHz, CDCl₃) δ 8.67 (s, 1H); 8.55 (d, J=4.20 Hz, 1H); 7.92-7.86 (m, 2H); 7.73-7.68 (m, 1H); 7.48 (s, 1H); 7.43-7.37 (m, 2H); 7.36-7.31 (m, 1H); 7.29-7.25 (m, 1H); 6.81 (s, 1H); 5.01-4.90 (m, 1H); 4.62 (d, J=5.83 Hz, 2H); 2.82 (qd, J=0.84 Hz, 7.45, 2H); 1.38 (t, J=7.51 Hz, 3H).

¹³C NMR (126 MHz, CDCl₃) δ 155.7, 149.5, 149.3, 146.9, 143.3, 141.1, 139.2, 137.1, 135.2, 133.9, 128.7, 128.4, 127.5, 124.6, 123.9, 99.4, 45.0, 16.4, 13.6.

HRMS (APCI): calcd. for $C_{21}H_{20}N_3O$ [M+H]⁺=330.1601; found [M+H]⁺=330.1598.

Preparative Examples 31B-31D

By essentially same procedure set forth in Preparative Example 31A, using proper amines instead of 3-picolylamine, the compounds given below were prepared.

Preparative Example 31B

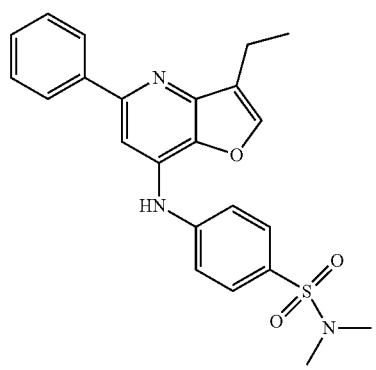 [SMILES: CCc1coc2c(Nc3ccc(S(=O)(=O)N(C)C)cc3)cc(-c3ccccc3)nc12]

Pale yellow solid.

¹H NMR (500 MHz, CDCl₃) δ 7.97-7.91 (m, 2H); 7.78-7.73 (m, 2H); 7.59-7.55 (m, 1H); 7.50 (s, 1H); 7.46-7.32 (m, 5H); 6.90 (brs, 1H); 2.86 (qd, J=0.86 Hz, 7.44 Hz, 2H); 2.76-2.70 (m, 6H); 1.40 (t, J=7.51 Hz, 3H).

¹³C NMR (126 MHz, CDCl₃) δ 155.3, 148.1, 144.6, 144.3, 140.1, 138.0, 133.9, 129.9, 129.3, 128.9, 127.6, 126.6, 124.7, 118.7, 103.1, 38.2, 16.4, 13.6.

HRMS (APCI): calcd. for $C_{23}H_{24}N_3O_3S$ [M+H]⁺=422.1533; found [M+H]⁺=422.1534.

Preparative Example 31C

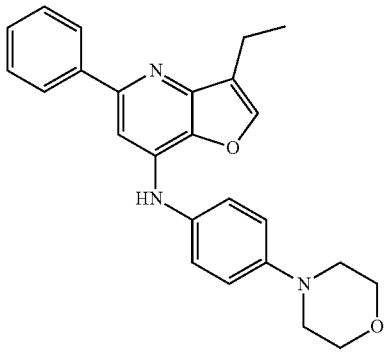 [SMILES: CCc1coc2c(Nc3ccc(N4CCOCC4)cc3)cc(-c3ccccc3)nc12]

Brown solid.
$^1$H NMR (500 MHz, CDCl$_3$) δ 7.92-7.86 (m, 2H); 7.55-7.52 (m, 1H); 7.42-7.30 (m, 4H); 7.23-7.20 (m, 1H); 7.17-7.13 (m, 1H); 6.98-6.92 (m, 2H); 6.31 (brs, 1H); 3.90-3.84 (m, 4H); 3.20-3.14 (m, 4H); 2.87 (q, J=7.42 Hz, 2H); 1.39 (t, J=7.50 Hz, 3H).
$^{13}$C NMR (126 MHz, CDCl$_3$) δ 155.3, 149.0, 143.5, 137.3, 131.6, 128.7, 128.5, 127.7, 124.6, 124.6, 124.5, 123.8, 117.0, 116.4, 100.3, 67.1, 49.8, 16.5, 13.6.
HRMS (APCI): calcd. for C$_{25}$H$_{26}$N$_3$O$_2$ [M+H]$^+$=400.2020; found [M+H]$^+$=400.2019.

Preparative Example 31D

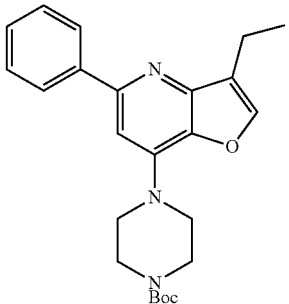 [SMILES: CCc1coc2c(N3CCN(C(=O)OC(C)(C)C)CC3)cc(-c3ccccc3)nc12]

Brown solid foam.
$^1$H NMR (500 MHz, CDCl$_3$) δ 7.98-7.93 (m, 2H); 7.53-7.50 (m, 1H); 7.46-7.40 (m, 2H); 7.39-7.33 (m, 1H); 6.92 (s, 1H); 3.66-3.56 (m, 8H); 2.84 (q, J=7.39 Hz, 2H); 1.48 (s, 9H); 1.38 (t, J=7.51 Hz, 3H).
$^{13}$C NMR (126 MHz, CDCl$_3$) δ 155.4, 154.9, 143.0, 142.2, 138.4, 128.8, 128.5, 127.6, 124.2, 102.8, 80.4, 48.1, 28.6, 16.3, 13.6.
HRMS (APCI): calcd. for C$_{24}$H$_{30}$N$_3$O$_3$ [M+H]$^+$=408.2282; found [M+H]$^+$=408.2281.

Preparative Example 32

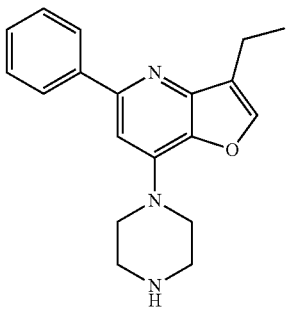 [SMILES: CCc1coc2c(N3CCNCC3)cc(-c3ccccc3)nc12]

To a stirred solution of the product from Preparative Example 31D (0.088 g; 0.22 mmol) in ethanol (2 mL) was added aqueous HCl (3M; 1.4 mL; 4.2 mmol) and the resulting mixture was stirred under N$_2$ at 60° C. for 17 h. Then, the ethanol and HCl were evaporated and the oily residue was mixed with CH$_2$Cl$_2$ (2 mL), MeOH (1 mL) and Na$_2$CO$_3$ (200 mg) and the mixture was stirred at 25° C. After 20 min., the solvents were evaporated and the solid residue was purified by column chromatography on silica gel (eluent:CH$_2$Cl$_2$/7N NH$_3$ in MeOH—15:1) to yield the product as a pale solid (0.048 g; 72%).
$^1$H NMR (500 MHz, CDCl$_3$) δ 7.99-7.94 (m, 2H); 7.51-7.48 (m, 1H); 7.46-7.40 (m, 2H); 7.38-7.32 (m, 1H); 6.93 (s, 1H); 3.63-3.56 (m, 4H); 3.11-3.04 (m, 4H); 2.82 (qd, J=1.22 Hz, 7.50 Hz, 2H); 2.04 (brs, 1H); 1.37 (t, J=7.51 Hz, 3H).
$^{13}$C NMR (126 MHz, CDCl$_3$) δ 155.4, 148.4, 142.7, 142.6, 141.3, 138.5, 128.7, 128.3, 127.5, 124.2, 102.5, 49.3, 46.1, 16.3, 13.6.
HRMS (APCI): calcd. for C$_{19}$H$_{22}$N$_3$O [M+H]$^+$=308.1757; found [M+H]$^+$=308.1755.

Preparative Example 33

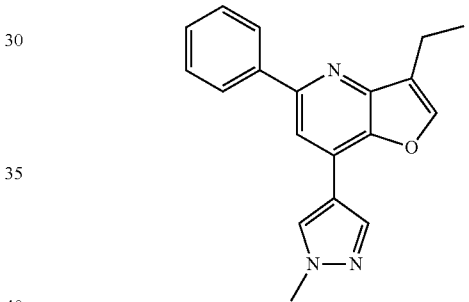

To a mixture of the product from Preparative Example 26 (0.047 g; 0.18 mmol), 1-methylpyrazole-4-boronic acid pinacol ester (0.045 g; 0.22 mmol), K$_3$PO$_4$ (0.163 g; 0.77 mmol) and PdCl$_2$(dppf) (0.009 g; 0.013 mmol) were added under N$_2$ 1,2-dimethoxyethane (2 mL) and water (0.5 mL). The reaction mixture was refluxed for 15 hrs. Then it was cooled to 25° C., diluted with EtOAc (15 mL), poured into brine (20 mL) and extracted with EtOAc (3×15 mL). The organic extracts were dried over Na$_2$SO$_4$, filtered and the solvent was evaporated. The residue was purified by column chromatography on silica gel (eluent:CH$_2$Cl$_2$/EtOAc—10:1). So obtained oil was further purified by preparative TLC (eluent:CH$_2$Cl$_2$) to yield the product as a white solid (0.024 g; 43%).
$^1$H NMR (500 MHz, CDCl$_3$) δ 8.14 (d, J=3.08 Hz, 2H); 8.07-8.02 (m, 2H); 7.73 (s, 1H); 7.67-7.64 (m, 1H); 7.50.7.44 (m, 2H); 7.41-7.36 (m, 1H); 3.99 (s, 3H); 2.87 (qd, J=1.10 Hz, 7.49 Hz, 2H); 1.41 (t, J=7.52 Hz, 3H).
$^{13}$C NMR (126 MHz, CDCl$_3$) δ 154.4, 148.2, 144.7, 144.2, 140.4, 138.4, 130.5, 128.9, 128.6, 127.5, 124.3, 124.2, 116.1, 112.5, 39.5, 16.3, 13.6.
HRMS (APCI): calcd. for C$_{19}$H$_{18}$N$_3$O [M+H]$^+$=304.1444; found [M+H]$^+$=304.1444.

Preparative Example 34A

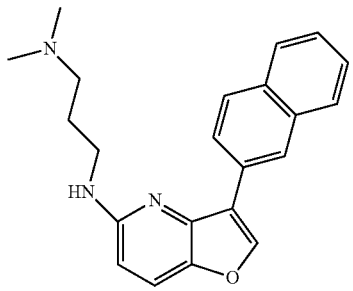 [SMILES: CN(C)CCCNc1ccc2occ(-c3ccc4ccccc4c3)c2n1]

Into a 10 mL flask were placed 1,2-dimethoxyethane (3 mL), Pd(OAc)$_2$ (1.8 mg, 0.008 mmol) and CyPF(t-Bu) (4.4 mg, 0.008 mmol) and the mixture was stirred at 25° C. under N$_2$ for 5 mm. Then, the product from Preparative Example 5A (55 mg, 0.20 mmol), N$^1$,N$^1$-dimethylpropane-1,3-diamine (24 mg, 0.24 mmol) and t-BuONa (28 mg, 0.30 mmol) were added and the mixture was refluxed for 22 h. Brine (30 mL) was added and the mixture was extracted with EtOAc (30+20+20 mL). The organic phase was dried over Na$_2$SO$_4$, filtered, and the solvent was evaporated. The residue was purified by preparative TLC on silica gel (CH$_2$Cl$_2$/7M solution of NH$_3$ in MeOH; 30:1). The product was obtained as a green solid (24 mg, 35%).

$^1$H NMR (500 MHz, CDCl$_3$) δ 8.09 (s, 1H), 8.04 (dd, J=8.5, 1.7 Hz, 1H), 7.94-7.86 (m, 2H), 7.84 (d, J=7.9 Hz, 1H), 7.56 (d, J=8.9 Hz, 1H), 7.52-7.43 (m, 2H), 6.42 (d, J=8.9 Hz, 1H), 3.56 (t, J=6.6 Hz, 2H), 2.53 (t, J=6.9 Hz, 2H), 2.31 (s, 6H), 1.94 (p, J=6.8 Hz, 2H).

$^{13}$C NMR (126 MHz, CDCl$_3$) δ 156.9, 144.02, 143.7, 143.4, 133.8, 132.6, 128.9, 128.3, 128.1, 127.7, 126.1, 125.8, 125.7, 124.8, 120.7, 120.6, 105.0, 58.0, 45.4, 41.5, 27.0.

HRMS (ESI): calcd. for C$_{22}$H$_{23}$N$_3$O [M+H]$^+$=346.1914; found [M+H]$^+$=346.1912.

Preparative Example 34B

By essentially same procedure set forth in Preparative Example 34A, using 2-methoxyethanamine instead of N$^1$,N$^1$-dimethylpropane-1,3-diamine, the compound given below was prepared.

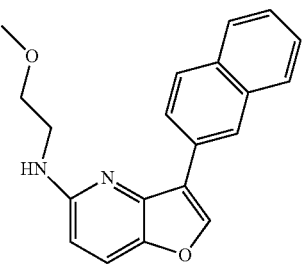 [SMILES: COCCNc1ccc2occ(-c3ccc4ccccc4c3)c2n1]

Dark red solid.

$^1$H NMR (500 MHz, CDCl$_3$) δ 8.84 (s, 1H), 8.10 (s, 1H), 8.04 (dd, J=8.5, 1.7 Hz, 1H), 7.96-7.87 (m, 2H), 7.87-7.81 (m, 1H), 7.59 (d, J=8.9 Hz, 1H), 7.53-7.44 (m, 2H), 6.46 (d, J=8.9 Hz, 1H), 3.72 (s, 4H), 3.43 (s, 3H).

$^{13}$C NMR (126 MHz, CDCl$_3$) δ 156.5, 144.3, 143.9, 133.9, 132.8, 128.8, 128.4, 128.2, 127.8, 126.2, 125.9, 125.8, 124.9, 121.0, 120.8, 105.6, 71.6, 58.9, 42.4.

HRMS (APCI): calcd. for C$_{20}$H$_{18}$N$_2$O$_2$ [M+H]$^+$= 319.1441; found [M+H]$^+$=319.1437.

Preparative Example 35

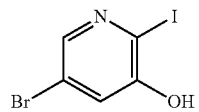

5-bromopyridin-3-ol (1.1 g, 6.3 mmol), iodine (1.6 g, 6.3 mmol), Na$_2$CO$_3$ (1.4 g, 13.2 g) and H$_2$O (21 mL) were placed into a 100 mL round bottom flask. The mixture was stirred under N$_2$ at 25° C. for 3 h. The mixture was neutralized with 1M aqueous solution of HCl and extracted with EtOAc (60+40+40 mL). The organic phase was washed with brine (50 mL), dried over MgSO$_4$ and filtered. The product was obtained as a brown solid (1.89 g; 100%).

$^1$H NMR (300 MHz, CDCl$_3$) δ 8.08 (d, J=2.1 Hz, 1H), 7.38 (d, J=2.1 Hz, 1H), 5.39 (s, 1H).

Preparative Example 36

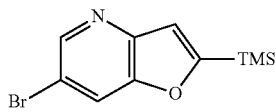

The product from Preparative Example 35 (1.88 g, 6.27 mmol), 1,4-dioxane (12 mL) and TEA (12 mL) were placed into a 100 mL round bottom flask. The mixture was purged with N$_2$, then ethynyltrimethylsilane (1.15 mL, 8.15 mmol), PdCl$_2$(PPh$_3$)$_2$ (132 mg, 0.188 mmol) and CuI (71 mg, 0.376 mmol) were added. The mixture was stirred under N$_2$ at 45° C. for 3 h. The solvent was evaporated and the residue was purified by column chromatography on silica gel (EtOAc/hexane; 1:15). The product was obtained as an orange solid (1.04 g, 61%).

$^1$H NMR (500 MHz, CDCl$_3$) δ 8.58 (d, J=1.9 Hz, 1H), 7.91 (dd, J=1.9, 1.0 Hz, 1H), 7.10 (d, J=1.0 Hz, 1H), 0.37 (s, 9H).

$^{13}$C NMR (126 MHz, CDCl$_3$) δ 170.2, 150.9, 147.1, 146.8, 121.1, 117.1, 115.2, −1.9.

HRMS (APCI): calcd. for C$_{10}$H$_{12}$BrNOSi [M+H]$^+$= 269.9944; found [M+H]$^+$=269.9954.

Preparative Example 37

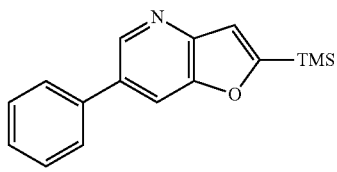 [SMILES: C[Si](C)(C)c1cc2ncc(-c3ccccc3)cc2o1]

The product from Preparative Example 36 (47 mg, 0.174 mmol), phenylboronic acid (28 mg, 0.226 mmol), 1,2-dimethoxyethane (8 mL), TEA (1 mL) and H$_2$O (2 mL) were placed into a 25 mL round bottom flask and the mixture was purged with N$_2$. Then, PdCl$_2$(dppf) (3.8 mg, 5.2 μmol) was added and the mixture was refluxed under N$_2$ for 75 mm. After addition of brine (25 mL), the mixture was extracted with EtOAc (3×20 mL). The organic phase was dried over MgSO₄, filtered, and the solvent was evaporated. The residue was purified by column chromatography on silica gel (EtOAc/hexane; 1:10). The product was obtained as a white solid (39 mg, 84%).

¹H NMR (300 MHz, CDCl₃) δ 8.78 (d, J=1.8 Hz, 1H), 7.93 (d, J=0.7 Hz, 1H), 7.69-7.59 (m, 2H), 7.55-7.35 (m, 3H), 7.17 (d, J=0.8 Hz, 1H), 0.40 (s, 9H).

¹³C NMR (126 MHz, CDCl₃) δ 169.6, 151.2, 147.5, 145.1, 138.5, 132.9, 129.7, 129.2, 127.9, 127.6, 117.1, 116.4, 115.5, −1.8.

HRMS (APCI): calcd. for C₁₆H₁₇NOSi [M+H]⁺= 268.1152; found [M+H]⁺=268.1160.

Preparative Example 38

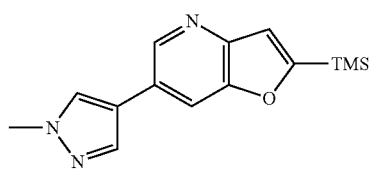 [SMILES: Cn1cc(-c2cnc3cc([Si](C)(C)C)oc3c2)cn1]

The product from Preparative Example 36 (47 mg, 0.174 mmol), 1-methyl-4-(4,4,5,5-tetramethyl-1,3,2-dioxaborolan-2-yl)-1H-pyrazole (47 mg, 0.226 mmol), 1,2-dimethoxyethane (8 mL), TEA (1 mL) and H₂O (2 mL) were placed into a 25 mL round bottom flask and the mixture was purged with N₂. Then, PdCl₂(dppf) (3.8 mg, 5.2 µmol) was added and the mixture was refluxed under N₂ for 70 min. After addition of brine (25 mL), the mixture was extracted with EtOAc (3×20 mL). The organic phase was dried over MgSO₄, filtered, and the solvent was evaporated. The residue was purified by column chromatography on silica gel (CH₂Cl₂/MeOH; 20:1). The product was obtained as a yellow wax (51 mg, 99%).

¹H NMR (500 MHz, CDCl₃) δ 8.67 (d, J=1.7 Hz, 1H), 7.79 (m, 2H), 7.68 (s, 1H), 7.12 (d, J=1.0 Hz, 1H), 3.97 (s, 3H), 0.37 (s, 9H).

¹³C NMR (126 MHz, CDCl₃) δ 168.9, 151.3, 146.7, 143.8, 137.1, 127.3, 124.6, 120.5, 117.2, 114.6, 39.3, −1.9.

HRMS (APCI): calcd. for C₁₄H₁₇N₃OSi [M+H]⁺= 272.1214; found [M+H]⁺=272.1219.

Preparative Example 39

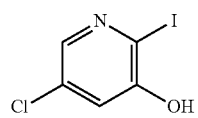

5-chloropyridin-3-ol (5.12 g, 39.7 mmol), iodine (10.1 g, 39.7 mmol), Na₂CO₃ (8.83 g, 83.3 mmol) and H₂O (80 mL) were placed into a 500 mL round bottom flask and the mixture was stirred under N₂ at 25° C. for 3.5 h. The mixture was neutralized with 1M aqueous solution of HCl (ca. 120 mL) and extracted with EtOAc (120+70+70 mL). The organic phase was washed with brine (80 mL), dried over MgSO₄ and filtered. The product was obtained as a brown solid (10.13 g; 100%).

¹H NMR (300 MHz, DMSO) δ 11.38 (s, 1H), 7.95 (d, J=2.3 Hz, 1H), 7.17 (d, J=2.3 Hz, 1H).

Preparative Example 40

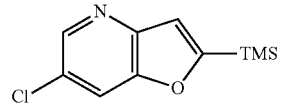 [SMILES: C[Si](C)(C)c1cc2ncc(Cl)cc2o1]

The product from Preparative Example 39 (8.34 g, 32.7 mmol), ethynyltrimethylsilane (6.0 mL, 42.5 mmol), PdCl₂(PPh₃)₂ (688 mg, 0.98 mmol), CuI (373 mg, 1.96 mmol), 1,4-dioxane (25 mL) and TEA (25 mL) were placed into a 250 mL round bottom flask. The mixture was stirred under N₂ at 45° C. for 2.5 h. The solvent was evaporated and the residue was purified by column chromatography on silica gel (EtOAc/hexane; 1:15). The product was obtained as an orange solid (4.37 g, 59%).

¹H NMR (500 MHz, CDCl₃) δ 8.52 (dd, J=1.9, 1.4 Hz, 1H), 7.81-7.76 (m, 1H), 7.16-7.12 (m, 1H), 0.40 (d, J=1.0 Hz, 9H).

¹³C NMR (126 MHz, CDCl₃) δ 170.3, 150.5, 146.9, 144.9, 127.2, 118.3, 117.1, −1.9.

HRMS (APCI): calcd. for C₁₀H₁₂ClNOSi [M+H]⁺= 226.0449; found [M+H]⁺=226.0458.

Preparative Example 41

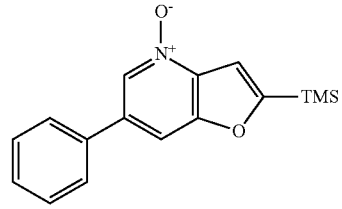 [SMILES: C[Si](C)(C)c1cc2c(cc(-c3ccccc3)c[n+]2[O-])o1]

The product from Preparative Example 37 (1.60 g, 5.98 mmol), CH₂Cl₂ (12 mL) and mCPBA (1.86 g, 10.8 mmol) were placed into a 100 mL round bottom flask and the mixture was stirred under N₂ at 25° C. for 3 h. The mixture was neutralized with saturated aqueous solution of NaHCO₃ (30 mL) and extracted with CH₂Cl₂ (3×25 mL). The organic phase was dried over MgSO₄ and filtered. The solvent was evaporated and the residue was purified by column chromatography on silica gel (EtOAc/acetone; 9:1). The product was obtained as a white solid (1.38 g, 82%).

¹H NMR (500 MHz, CDCl₃) δ 8.46 (d, J=1.1 Hz, 1H), 7.62 (m, 1H), 7.57 (m, 2H), 7.49 (m, 2H), 7.45 (m, 1H), 7.41 (d, J=0.9 Hz, 1H), 0.39 (s, 9H).

¹³C NMR (126 MHz, CDCl₃) δ 169.6, 154.5, 137.7, 136.3, 135.3, 133.4, 129.5, 129.0, 127.4, 111.1, 109.3, −2.0.

HRMS (APCI): calcd. for C₁₆H₁₇NO₂Si [M+H]⁺= 284.1101; found [M+H]⁺=284.1099.

Preparative Example 42

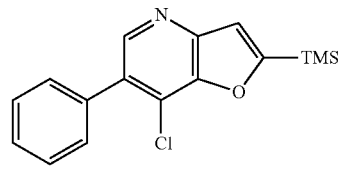 [SMILES: C[Si](C)(C)c1cc2ncc(-c3ccccc3)c(Cl)c2o1]

The product from Preparative Example 41 (1.35 g, 4.75 mmol), chloroform (10 mL) and POCl₃ (7.96 mL, 8.54 mmol) were placed into a 100 mL round bottom flask and the mixture was refluxed under N₂ for 1 h. The solvent and POCl₃ were evaporated and the residue was mixed with saturated aqueous solution of NaHCO₃ (50 mL) and extracted with CH₂Cl₂ (50+25+25 mL). The organic phase was dried over MgSO₄ and filtered. The solvent was evaporated and the residue was purified by column chromatography on silica gel (EtOAc/CH₂Cl₂; 1:20). The product was obtained as a white solid (0.824 g, 57%).

$^1$H NMR (500 MHz, CDCl₃) δ 8.49 (s, 1H), 7.55-7.42 (m, 5H), 7.20 (s, 1H), 0.42 (s, 9H).

$^{13}$C NMR (126 MHz, CDCl₃) δ 170.4, 148.3, 147.9, 147.6, 135.6, 132.0, 130.1, 128.5, 128.3, 124.3, 117.7, −1.8.

HRMS (APCI): calcd for C₁₆H₁₆ClNOSi [M+H]⁺= 302.0762; found [M+H]⁺=302.0765.

The structural integrity of this compound was also confirmed by X-ray crystallography.

Preparative Example 43

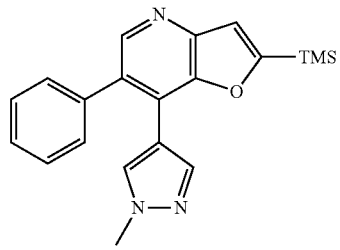 [SMILES: Cn1cc(-c2c(-c3ccccc3)cnc3cc([Si](C)(C)C)oc23)cn1]

Pd(OAc)₂ (16.7 mg, 74 μmol), SPhos (40 mg, 99 μmol) and 1-butanol (5 mL) were placed into a 25 mL flask and stirred for 5 min. The product from Preparative Example 42 (750 mg, 2.48 mmol), 1-methyl-4-(4,4,5,5-tetramethyl-1,3,2-dioxaborolan-2-yl)-1H-pyrazole (724 mg, 3.48 mmol), TEA (10.4 mL, 74 mmol) and H₂O (1 mL) were added and the mixture was refluxed for 15 h. The solvent was evaporated and the residue was purified by column chromatography on silica gel (EtOAc/CH₂Cl₂; 1:10). The product was obtained as a pale yellow solid (427 mg, 50%).

$^1$H NMR (500 MHz, CDCl₃) δ 8.41 (s, 1H), 7.58 (s, 1H), 7.47-7.41 (m, 3H), 7.38-7.32 (m, 2H), 7.27 (s, 1H), 7.20 (s, 1H), 3.84 (s, 3H), 0.42 (s, 9H).

$^{13}$C NMR (126 MHz, CDCl₃) δ 168.5, 148.0, 147.8, 147.6, 140.9, 139.1, 131.4, 130.3, 130.1, 128.9, 128.0, 122.5, 117.5, 114.3, 39.2, −1.7.

HRMS (APCI): calcd. for C₂₀H₂₁N₃OSi [M+H]⁺= 348.1527; found [M+H]⁺=348.1529.

Preparative Example 44

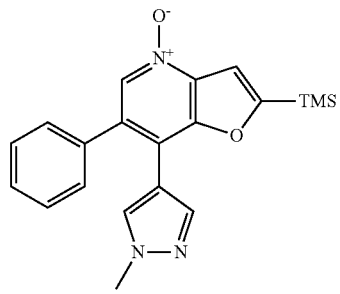 [SMILES: Cn1cc(-c2c(-c3ccccc3)c[n+]([O-])c3cc([Si](C)(C)C)oc23)cn1]

The product from Preparative Example 43 (420 mg, 1.21 mmol), CH₂Cl₂ (5 mL) and mCPBA (375 mg, 2.18 mmol) were placed into a 25 mL round bottom flask and the mixture was stirred under N₂ at 25° C. for 1 h. The mixture was mixed with saturated aqueous solution of NaHCO₃ (40 mL), brine (30 mL) was added and the mixture was extracted with CH₂Cl₂ (50+25+25 mL). The organic phase was dried over MgSO₄ and filtered. The solvent was evaporated and the residue was purified by column chromatography on silica gel (EtOAc/acetone; 2:1). The product was obtained as a light yellow semi-solid (357 mg, 81%).

$^1$H NMR (500 MHz, CDCl₃) δ 8.13 (s, 1H), 7.49 (s, 1H), 7.47-7.42 (m, 4H), 7.34-7.28 (m, 2H), 7.15 (s, 1H), 3.82 (s, 3H), 0.42 (s, 9H).

$^{13}$C NMR (126 MHz, CDCl₃) δ 168.8, 151.0, 140.1, 137.5, 136.8, 135.5, 132.2, 130.6, 129.7, 129.1, 128.8, 116.2, 113.5, 111.4, 39.2, −1.9.

HRMS (APCI): calcd. for C₂₀H₂₁N₃O₂Si [M+H]⁺= 364.1476; found [M+H]⁺=364.1478.

Preparative Example 45

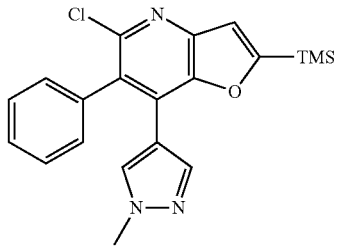 [SMILES: Cn1cc(-c2c(-c3ccccc3)c(Cl)nc3cc([Si](C)(C)C)oc23)cn1]

The product from Preparative Example 44 (351 mg, 0.966 mmol) and POCl₃ (4 mL) were placed into a 25 mL round bottom flask and the mixture was stirred under N₂ at 100° C. for 25 min. The POCl₃ was evaporated, the residue was mixed with saturated aqueous solution of NaHCO₃ (25 mL) and extracted with CH₂Cl₂ (20+15+15 mL). The organic phase was dried over MgSO₄ and filtered. The solvent was evaporated and the residue was purified by column chromatography on silica gel (EtOAc/hexane; 1:1). The product was obtained as a white solid (316 mg, 86%).

$^1$H NMR (500 MHz, CDCl₃) δ 7.53-7.47 (m, 4H), 7.28-7.26 (m, 1H), 7.26-7.25 (m, 1H), 7.13 (s, 1H), 6.96 (s, 1H), 3.78 (s, 3H), 0.42 (s, 9H).

$^{13}$C NMR (126 MHz, CDCl₃) δ 169.6, 147.4, 147.3, 146.9, 140.9, 138.5, 131.6, 130.3, 129.2, 128.5, 127.8, 126.0, 116.9, 114.5, 39.2, −1.8.

HRMS (APCI): calcd. for C₂₀H₂₀ClN₃OSi [M+H]⁺= 382.1137; found [M+H]⁺=382.1141.

Preparative Example 46

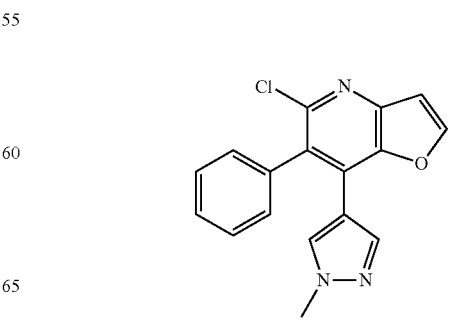

The product from Preparative Example 45 (285 mg, 0.746 mmol), KF (130 mg, 2.24 mmol) and MeOH (16 mL) were placed into a 50 mL round bottom flask and the mixture was stirred under $N_2$ at 62° C. for 43 h. The solvent was evaporated and the residue was purified by column chromatography on silica gel (EtOAc/hexane; 1:1). The product was obtained as a white solid (213 mg, 92%).

$^1$H NMR (500 MHz, CDCl$_3$) δ 7.93 (d, J=2.3 Hz, 1H), 7.52-7.47 (m, 3H), 7.31-7.26 (m, 3H), 7.21 (s, 1H), 7.00 (d, J=2.3 Hz, 1H), 3.80 (s, 3H).

$^{13}$C NMR (126 MHz, CDCl$_3$) δ 149.4, 148.0, 146.0, 144.4, 140.7, 138.2, 131.9, 130.3, 129.2, 128.6, 128.3, 126.6, 114.0, 108.3, 39.2.

HRMS (APCI): calcd. for $C_{18}H_{12}ClN_3O$ [M+H]$^+$= 310.0742; found [M+H]$^+$=310.0750.

Preparative Example 47

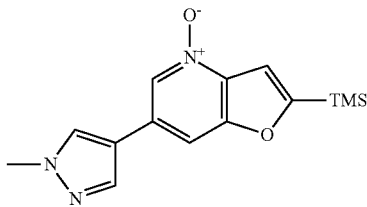 [SMILES: Cn1cc(-c2cc3oc([Si](C)(C)C)cc3[n+]([O-])c2)cn1]

The product from Preparative Example 38 (2.36 g, 8.7 mmol), CH$_2$Cl$_2$ (15 mL) and mCPBA (2.1 g, 15.7 mmol) were placed into a 100 mL round bottom flask and the mixture was stirred under $N_2$ at 25° C. for 45 h. Then, additional mCBPA (0.62 g, 3.6 mmol) was added and the mixture was stirred for additional 4 h. The mixture was mixed with saturated aqueous solution of NaHCO$_3$ (20 mL), brine (30 mL) was added, and the mixture was extracted with CH$_2$Cl$_2$ (3×70 mL). The organic phase was dried over MgSO$_4$ and filtered. The solvent was evaporated and the residue was purified by column chromatography on silica gel (EtOAc/MeOH; from 20:1 to 5:1). The product was obtained as a light yellow solid (1.67 g, 66%).

$^1$H NMR (300 MHz, CDCl$_3$) δ 8.36 (d, J=0.9 Hz, 1H), 7.76 (s, 1H), 7.63 (s, 1H), 7.49 (s, 1H), 7.36 (d, 1H), 3.98 (s, 3H), 0.38 (s, 9H).

$^{13}$C NMR (126 MHz, CDCl$_3$) δ 168.9, 154.6, 137.1, 131.9, 127.6, 126.8, 118.6, 111.1, 107.4, 39.5, −2.0.

HRMS (APCI): calcd. for $C_{14}H_{17}N_3O_2Si$ [2M+H]$^+$= 575.2253; found [2M+H]$^+$=575.2255.

Preparative Example 48

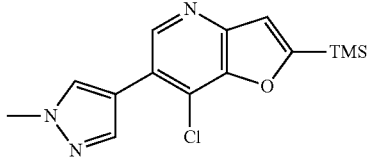 [SMILES: Cn1cc(-c2cnc3cc([Si](C)(C)C)oc3c2Cl)cn1]

The product from Preparative Example 47 (1.67 g, 5.81 mmol), chloroform (12 mL) and POCl$_3$ (9.75 mL, 105 mmol) were placed into a 100 mL round bottom flask and the mixture was refluxed under $N_2$ for 45 min. The solvent and POCl$_3$ were evaporated and the residue was mixed with saturated aqueous solution of NaHCO$_3$ (40 mL) and extracted with CH$_2$Cl$_2$ (50+30+30 mL). The organic phase was dried over MgSO$_4$ and filtered. The solvent was evaporated and the residue was purified by column chromatography on silica gel (CH$_2$Cl$_2$/MeOH; 14:1). The product was obtained as a white solid (1.15 g, 65%).

$^1$H NMR (500 MHz, CDCl$_3$) δ 8.58 (s, 1H), 7.87 (s, J=0.6 Hz, 1H), 7.83 (s, 1H), 7.15 (s, 1H), 4.00 (s, 3H), 0.40 (s, 9H).

$^{13}$C NMR (126 MHz, CDCl$_3$) δ 169.9, 148.2, 147.3, 146.4, 139.0, 129.8, 123.5, 123.2, 117.7, 116.5, 39.3, −1.9.

HRMS (APCI): calcd. for $C_{14}H_{16}N_3OSi$ [M+H]$^+$= 306.0824; found [M+H]$^+$=306.0825.

Preparative Example 49

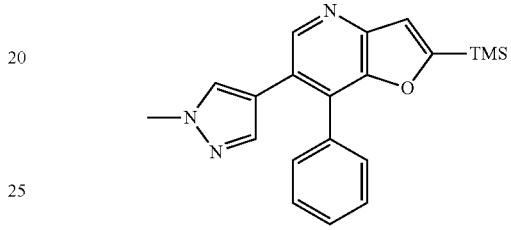

Pd(OAc)$_2$ (25 mg, 113 μmol), SPhos (62 mg, 150 μmol) and 1-butanol (8 mL) were placed into a 50 mL flask and stirred for 5 mm. The product from Preparative Example 48 (1.15 g, 3.76 mmol), phenylboronic acid (688 mg, 5.64 mmol), TEA (15.7 mL, 113 mmol) and H$_2$O (1.6 mL) were added and the mixture was refluxed under $N_2$ for 90 mm. The solvent was evaporated and the residue was purified by column chromatography on silica gel (EtOAc/MeOH; from 20:1 to 15:1). The product was obtained as a light grey solid (1.32 g, 100%).

$^1$H NMR (500 MHz, CDCl$_3$) δ 8.64 (s, 1H), 7.45-7.39 (m, 5H), 7.25 (d, J=0.6 Hz, 1H), 7.17 (s, 1H), 7.04 (s, 1H), 3.81 (s, 3H), 0.32 (s, 9H).

$^{13}$C NMR (126 MHz, CDCl$_3$) δ 169.0, 149.3, 147.1, 146.8, 139.1, 133.5, 130.1, 130.1, 129.2, 128.5, 128.5, 122.8, 118.7, 117.3, 39.0, −1.8.

HRMS (APCI): calcd. for $C_{20}H_{21}N_3OSi$ [M+H]$^+$= 348.1527; found [M+H]$^+$=348.1530.

Preparative Example 50

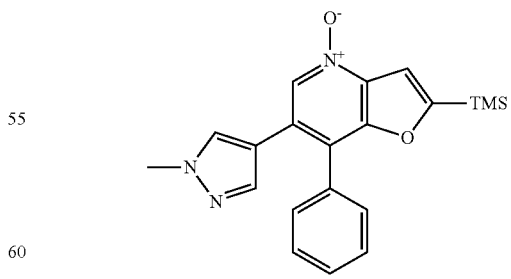

The product from Preparative Example 49 (1.3 g, 3.74 mmol), CH$_2$Cl$_2$ (10 mL) and mCPBA (1.16 g, 6.73 mmol) were placed into a 50 mL round bottom flask and the mixture was stirred under $N_2$ at 25° C. for 135 min. The mixture was mixed with saturated aqueous solution of NaHCO$_3$ (40 mL)

and then extracted with CH$_2$Cl$_2$ (50+40+40 mL). The organic phase was dried over MgSO$_4$ and filtered. The solvent was evaporated and the residue was purified by column chromatography on silica gel (EtOAc/MeOH; from 10:1 to 7:1). The product was obtained as a white semi-solid (1.13 g, 83%).

$^1$H NMR (500 MHz, CDCl$_3$) δ 8.33 (s, 1H), 7.47-7.40 (m, 4H), 7.40-7.33 (m, 2H), 7.21 (s, 1H), 7.00 (s, 1H), 3.81 (s, 3H), 0.31 (s, 9H).

$^{13}$C NMR (126 MHz, CDCl$_3$) δ 169.2, 152.6, 138.9, 136.9, 134.2, 132.4, 130.2, 129.5, 128.8, 128.7, 125.3, 123.3, 116.9, 111.2, 39.2, -2.0.

HRMS (APCI): calcd. for C$_{20}$H$_{21}$N$_3$O$_2$Si [M+H]$^+$= 364.1476; found [M+H]$^+$=364.1479.

Preparative Example 51

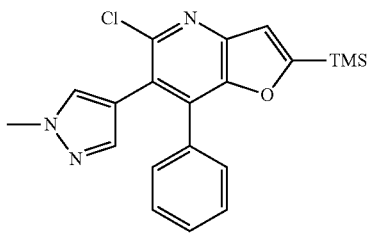 [SMILES: Cn1cc(-c2c(Cl)nc3cc([Si](C)(C)C)oc3c2-c2ccccc2)cn1]

The product from Preparative Example 50 (1.13 g, 3.11 mmol) and POCl$_3$ (6 mL) were placed into a 50 mL round bottom flask and the mixture was stirred under N$_2$ at 100° C. for 20 mm. The POCl$_3$ was evaporated, the residue was mixed with saturated aqueous solution of NaHCO$_3$ (100 mL) and extracted with CH$_2$Cl$_2$ (60+40+40 mL). The organic phase was dried over MgSO$_4$ and filtered. The solvent was evaporated and the residue was purified by column chromatography on silica gel (EtOAc/hexane; 1:2). The product was obtained as a white solid (1.02 g, 86%).

$^1$H NMR (300 MHz, CDCl$_3$) δ 7.38-7.32 (m, 3H), 7.31-7.26 (m, 3H), 7.14 (s, 1H), 7.10 (s, 1H), 3.83 (s, 3H), 0.32 (s, 9H).

$^{13}$C NMR (126 MHz, CDCl$_3$) δ 170.8, 148.5, 147.6, 146.6, 141.0, 134.6, 133.4, 131.2, 130.2, 128.5, 128.2, 121.5, 116.7, 116.5, 39.0, -1.9.

HRMS (APCI): calcd. for C$_{20}$H$_{20}$ClN$_3$OSi [M+H]$^+$= 382.1137; found [M+H]$^+$=382.1141.

Preparative Example 52

By essentially same procedure set forth in Preparative Example 46, using the product from Preparative Example 51, the compound given below was prepared.

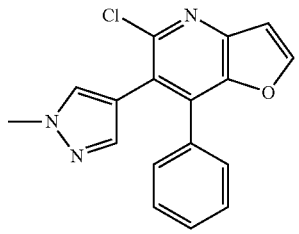 [SMILES: Cn1cc(-c2c(Cl)nc3ccoc3c2-c2ccccc2)cn1]

White solid.

$^1$H NMR (500 MHz, CDCl$_3$) δ 7.83 (d, J=2.3 Hz, 1H), 7.38-7.35 (m, 3H), 7.29-7.26 (m, 3H), 7.17 (s, 1H), 6.98 (d, J=2.3 Hz, 1H), 3.83 (s, 3H).

$^{13}$C NMR (126 MHz, CDCl$_3$) δ 150.3, 148.0, 145.6, 140.9, 135.2, 133.0, 131.1, 130.0, 128.8, 128.4, 122.2, 116.2, 108.1, 39.1.

HRMS (APCI): calcd. for C$_{17}$H$_{12}$ClN$_3$O [M+H]$^+$= 310.0742; found [M+H]$^+$=310.0746.

Preparative Example 53

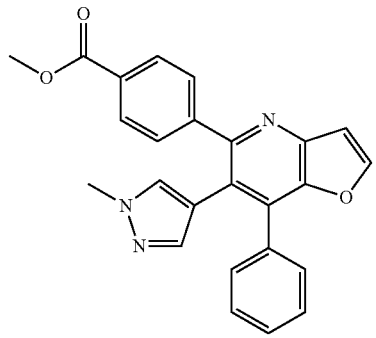 [SMILES: COC(=O)c1ccc(-c2nc3ccoc3c(-c3ccccc3)c2-c2cnn(C)c2)cc1]

The product from Preparative Example 52 (30 mg, 0.969 mmol), 1,2-dimethoxyethane (2 mL), K$_3$PO$_4$ (61.7 mg, 0.291 mmol), (4-(methoxycarbonyl)phenyl)boronic acid (26.1 mg, 0.145 mmol) and PdCl$_2$(dppf) (4.3 mg, 5.8 µmol) were placed into a 25 mL round bottom flask. The mixture was refluxed under N$_2$ for 25 h, then additional PdCl$_2$(dppf) (5 mg, 6 µmol) and H$_2$O (0.4 mL) were added and the mixture was refluxed for additional 14 h. The solvent was evaporated and the residue was purified by column chromatography on silica gel (EtOAc/hexane; 1:1). The product was obtained as a colorless wax (17 mg, 43%).

$^1$H NMR (500 MHz, CDCl$_3$) δ 8.00-7.94 (m, 2H), 7.85 (d, J=1.7 Hz, 1H), 7.48-7.43 (m, 2H), 7.39-7.35 (m, 3H), 7.32-7.27 (m, 2H), 7.08 (s, 1H), 6.80 (s, 1H), 6.63 (s, 1H), 3.91 (s, 3H), 3.65 (s, 3H).

$^{13}$C NMR (126 MHz, CDCl$_3$) δ 171.2, 167.1, 155.4, 149.9, 146.5, 146.2, 145.8, 140.7, 133.3, 133.1, 130.9, 130.1, 129.9, 129.3, 129.1, 128.5, 128.4, 121.9, 117.5, 108.6, 52.2, 38.9.

HRMS (APCI): calcd. for C$_{25}$H$_{19}$N$_3$O$_3$ [M+H]$^+$= 410.1499; found [M+H]$^+$=410.1492.

Preparative Example 54

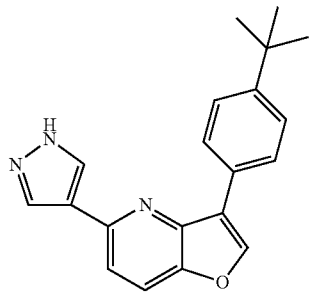 [SMILES: CC(C)(C)c1ccc(-c2coc3ccc(-c4cn[nH]c4)nc23)cc1]

The product from Preparative Example 5D (40 mg, 0.14 mmol), tert-butyl 4-(4,4,5,5-tetramethyl-1,3,2-dioxaborolan-2-yl)-1H-pyrazole-1-carboxylate (49 mg, 0.168 mmol), K$_3$PO$_4$ (104 mg, 0.49 mmol), 1,2-dimethoxyethane (2.4 mL), H$_2$O (0.6 mL) and PdCl$_2$(dppf) (6.2 mg, 8.4 µmol) were placed into a 10 mL round bottom flask and the mixture was refluxed under N₂ for 22 h. Then, additional PdCl₂(dppf) (8 mg, 10.9 μmol) was added and the mixture was refluxed for additional 4 h. The solvent was evaporated and the residue was purified by column chromatography on silica gel (EtOAc/hexane; 1:1). The product was obtained as a white solid (18.5 mg, 42%).

¹H NMR (500 MHz, DMSO-d6) δ 13.04 (s, 1H), 8.74 (s, 1H), 8.52-8.10 (m, 4H), 8.05 (d, J=8.6 Hz, 1H), 7.73 (d, J=8.7 Hz, 1H), 7.54 (d, J=8.2 Hz, 2H), 1.35 (s, 9H).

¹³C NMR (126 MHz, DMSO-d6) δ 149.8, 148.8, 146.7, 146.1, 144.8, 128.7, 127.7, 126.3, 125.4, 122.4, 119.9, 119.5, 115.9, 34.3, 31.1.

HRMS (APCI): calcd. for C₂₀H₁₉N₃O [M+H]⁺= 318.1601; found [M+H]⁺=318.1599.

Preparative Example 55

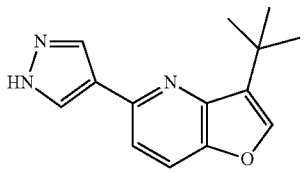 [SMILES: CC(C)(C)c1coc2ccc(-c3cn[nH]c3)nc12]

The product from Preparative Example 5E (11 mg, 52.5 μmol), degassed 1,2-dimethoxyethane (2 mL) and H₂O (0.5 mL) were placed into a 5 mL round bottom flask. Then, K₃PO₄ (39 mg, 0.184 mmol), tert-butyl 4-(4,4,5,5-tetramethyl-1,3,2-dioxaborolan-2-yl)-1H-pyrazole-1-carboxylate (18.5 mg, 63 μmol) and PdCl₂(dppf) (2 mg, 2.6 μmol) were added and the mixture was stirred under N₂ at 60° C. for 16 h. Then, additional PdCl₂(dppf) (2 mg, 2.6 μmol), the mixture was refluxed for additional 5 h, another portion of PdCl₂(dppf) (2 mg, 2.6 μmol) and the mixture was refluxed for additional 4 h. The solvent was evaporated and the residue was purified by column chromatography on silica gel (EtOAc/hexane; 1:1). The product was obtained as a yellow wax (2 mg, 15%).

¹H NMR (500 MHz, CDCl₃) δ 8.24 (b, J=47.6 Hz, 2H), 7.66 (d, J=8.2 Hz, 1H), 7.52 (s, 1H), 7.37 (d, J=8.1 Hz, 1H), 1.52 (s, 9H).

¹³C NMR (126 MHz, CDCl₃) δ 8147.7, 143.5, 131.1, 118.7, 115.2, 31.2, 29.8.

HRMS (APCI): calcd. for C₁₄H₁₅N₃O [M+H]⁺= 242.1288; found [M+H]⁺=242.1292.

Preparative Example 56

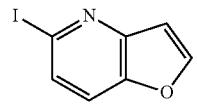

The product from Preparative Example 11 (1.78 g, 11.6 mmol) and degassed 1,4-dioxane (62 mL) were placed into a 250 mL round bottom flask, then AcCl (0.825 mL, 11.6 mmol) was added and the mixture was stirred under N₂ at 25° C. After 3 mm, NaI (17.4 g, 116 mmol) was added, the flask was wrapped with aluminum foil and the mixture was stirred at 106° C. for 70 h. Additional portions of AcCl were added at these times: 15 h, (0.70 mL, 98 mmol); 24 h, (0.80 mL, 11.2 mmol); 40 h (0.80 mL, 11.2 mmol); 48 h (0.825 mL, 11.6 mmol; 64 h (0.825 mL, 11.6 mmol). The solvent was evaporated, the residue was mixed with saturated solution of NaHCO₃ (50 mL) and with Na₂S₂O₃ (5 g), and extracted with CH₂Cl₂ (3×90 mL). The organic phase was dried over MgSO₄ and filtered. The mixture was concentrated to the volume of 75 mL and hexane (25 mL) was added. To the solution, upon cooling in ice bath, HCl (15 mL, 1M solution in Et₂O) was added. The precipitate was collected by filtration. To the solid, TEA (1.9 mL, 14 mmol) and CH₂Cl₂ (20 mL) were added, the mixture was cooled in ice bath, H₂O (60 mL) was added, and the mixture was extracted with CH₂Cl₂ (3×60 mL). The organic phase was dried over MgSO₄, filtered, and the solvent was evaporated. The product was obtained as a white solid (1.90 g, 67%).

¹H NMR (500 MHz, CDCl₃) δ 7.81 (d, J=2.3 Hz, 1H), 7.60 (d, J=8.5 Hz, 1H), 7.47 (dd, J=8.5, 0.9 Hz, 1H), 6.96 (dd, J=2.3, 0.9 Hz, 1H).

¹³C NMR (126 MHz, CDCl₃) δ 149.7, 149.5, 147.5, 129.5, 120.4, 112.0, 108.0.

HRMS (APCI): calcd. for C₇H₄INO [M+H]⁺=245.9410; found [M+H]⁺=245.9407.

Preparative Example 57

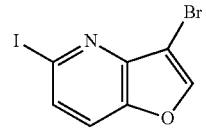 [SMILES: Brc1coc2ccc(I)nc12]

The product from Preparative Example 56 (1.86 g, 7.60 mmol) and CCl₄ (20 mL) were placed into a 100 mL round bottom flask and the mixture was cooled to −18° C. Then, bromine (6.49 mL, 114 mmol) was added slowly. The mixture was stirred under N₂ while allowed to warm up to 25° C. for 90 min. The mixture was poured into a mixture of water (100 mL), ice (50 mL) and Na₂S₂O₅ (30 g). The resulting mixture was extracted with CH₂Cl₂ (2×100 mL) and EtOAc (100 mL). The organic phase was washed with brine (100 mL), dried over MgSO₄, filtered, and the solvent was evaporated. Toluene (24 mL) and DBU (3.4 mL, 22.8 mmol) were added to the residue and the mixture was stirred under N₂ at 80° C. for 45 min. The solvent was evaporated and the residue was and purified by column chromatography on silica gel (EtOAc/hexane; from 1:7 to 1:5). The product was obtained as a white solid (1.77 g, 72%).

¹H NMR (500 MHz, CDCl₃) δ 7.85 (s, 1H), 7.69 (d, J=8.5 Hz, 1H), 7.47 (d, J=8.5 Hz, 1H).

¹³C NMR (126 MHz, CDCl₃) δ 147.4, 147.2, 146.8, 131.1, 120.9, 113.0, 98.9.

HRMS (APCI): calcd. for C₇H₃BrINO [M+H]⁺= 323.8515; found [M+H]⁺=323.8512.

Preparative Example 58

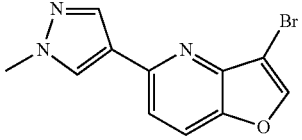 [SMILES: Cn1cc(-c2ccc3occ(Br)c3n2)cn1]

A mixture of the product from Preparative Example 57 (167 mg, 0.515 mmol), 1-methyl-4-(4,4,5,5-tetramethyl-1,3,2-dioxaborolan-2-yl)-1H-pyrazole (113 mg, 0.54 mmol), K₃PO₄ (383 mg, 1.80 mmol), and PdCl₂(dppf) (18.8 mg, 26

μmol) in 1,2-dimethoxyethane (2 mL) and H₂O (0.5 mL) was stirred under N₂ at 25° C. for 2.5 h. The solvent was evaporated and the residue was purified by column chromatography on silica gel (hexane/EtOAc; 2:3). The product was obtained as an orange solid (80 mg; 56%).

¹H NMR (500 MHz, CDCl₃) δ 8.04 (s, 1H), 7.97 (s, 1H), 7.85 (s, 1H), 7.73 (d, J=8.6 Hz, 1H), 7.46 (d, J=8.6 Hz, 1H), 3.96 (s, 3H).

¹³C NMR (126 MHz, CDCl₃) δ 149.9, 146.6, 146.3, 144.6, 137.6, 129.3, 123.6, 119.6, 116.9, 99.6, 39.3.

HRMS (APCI): calcd. for C₁₁H₈BrN₃O [M+H]⁺= 277.9924; found [M+H]⁺=277.9920.

Preparative Example 59

By essentially same procedure set forth in Preparative Example 58, using tert-butyl 4-(4,4,5,5-tetramethyl-1,3,2-dioxaborolan-2-yl)-1H-pyrazole-1-carboxylate instead of 1-methyl-4-(4,4,5,5-tetramethyl-1,3,2-dioxaborolan-2-yl)-1H-pyrazole, the compound given below was prepared.

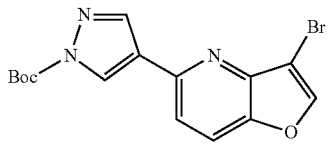 [SMILES: CC(C)(C)OC(=O)n1cc(-c2ccc3occ(Br)c3n2)cn1]

White solid.

¹H NMR (500 MHz, CDCl₃) δ 8.65 (s, 1H), 8.27 (s, 1H), 7.90 (s, 1H), 7.79 (d, J=8.6 Hz, 1H), 7.54 (d, J=8.6 Hz, 1H), 1.69 (s, 9H).

¹³C NMR (126 MHz, CDCl₃) δ 148.2, 147.6, 147.1, 146.7, 145.0, 142.5, 128.7, 125.7, 119.8, 117.5, 99.7, 86.0, 28.1.

HRMS (APCI): calcd. for C₁₅H₁₄BrN₃O₃ [M+H]⁺= 364.0291; found [M+H]⁺=364.0294. The structural integrity of this compound was also confirmed by X-ray crystallography.

Preparative Example 60

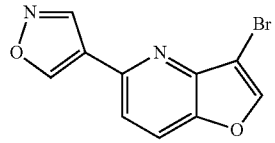 [SMILES: Brc1coc2ccc(-c3cnoc3)nc12]

A mixture of the product from Preparative Example 57 (127 mg, 0.393 mmol), K₃PO₄ (292 mg, 1.38 mmol), 4-(4,4,5,5-tetramethyl-1,3,2-dioxaborolan-2-yl)isoxazole (80.5 mg, 0.413 mmol), and PdCl₂(dppf) (14.4 mg, 19.7 μmol) in 1,2-dimethoxyethane (2.8 mL) and H₂O (0.7 mL) was stirred under N₂ at 40° C. for 25 h. The solvent was evaporated and the residue was purified by column chromatography on silica gel (CH₂Cl₂/EtOAc; 20:1). The product was obtained as a white solid (51 mg; 49%).

¹H NMR (500 MHz, CDCl₃) δ 9.00 (s, 1H), 8.88 (s, 1H), 7.93 (s, 1H), 7.82 (d, J=8.6 Hz, 1H), 7.50 (d, J=8.6 Hz, 1H).

¹³C NMR (126 MHz, CDCl₃) δ 155.7, 148.4, 147.5, 146.8, 146.1, 145.3, 122.2, 119.9, 117.8, 99.7.

HRMS (APCI): calcd. for C₁₀H₅BrN₂O2 [M+H]⁺= 264.9607; found [M+H]⁺=264.9603.

Preparative Example 61

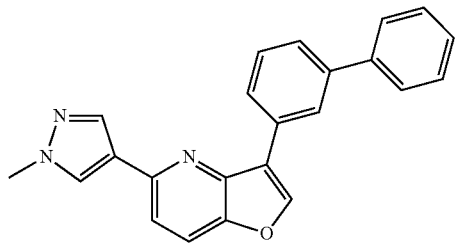 [SMILES: Cn1cc(-c2ccc3occ(-c4cccc(-c5ccccc5)c4)c3n2)cn1]

Degassed 1-butanol (2.0 mL) and H₂O (0.4 mL) were placed into a 10 mL round bottom flask, Pd(OAc)₂ (1 mg, 4 μmol) and SPhos (2.2 mg, 5.4 μmol) were added and the mixture was stirred at 25° C. for 3 mm. Then, the product from Preparative Example 58 (25 mg, 90 μmol), [1,1'-biphenyl]-3-ylboronic acid (25 mg, 0.126 mmol) and TEA (1.0 mL, 7.2 mmol) were added. The mixture was stirred under N₂ at 40° C. for 1 h, then at 50° C. for 2 h. The solvent was evaporated and the residue purified by column chromatography on silica gel (hexane/EtOAc; 1:1) and then by preparative TLC (hexane/acetone; 10:7). The product was obtained as a white solid (7 mg; 22%).

¹H NMR (500 MHz, CDCl₃) δ 8.57-8.53 (m, 1H), 8.18 (s, 1H), 8.14-8.10 (m, 1H), 8.03 (s, 1H), 8.00 (s, 1H), 7.77 (d, J=8.6 Hz, 1H), 7.75-7.71 (m, 2H), 7.63-7.54 (m, 2H), 7.53-7.44 (m, 3H), 7.42-7.37 (m, 1H), 3.99 (s, 3H).

¹³C NMR (126 MHz, CDCl₃) δ 148.8, 147.6, 145.8, 145.2, 141.7, 141.4, 137.7, 131.3, 129.2, 128.9, 128.9, 127.5, 127.3, 126.5, 126.2, 125.9, 124.3, 121.4, 119.2, 115.7, 39.3.

HRMS (APCI): calcd. for C₂₃H₁₇N₃O [M+H]⁺= 352.1444; found [M+H]⁺=352.1449.

Preparative Example 62

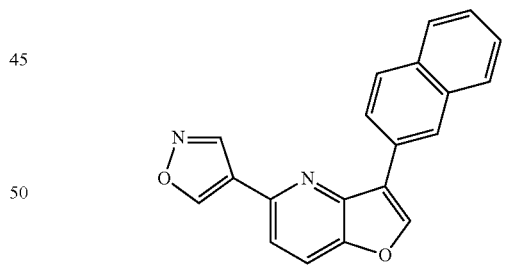

The product from Preparative Example 60 (21 mg, 79.2 μmol), Pd(OAc)₂ (1 mg, 4 μmol), SPhos (2 mg, 4.8 μmol), naphthalen-2-ylboronic acid (17.7 mg, 103 μmol), 1-butanol (2 mL), H₂O (0.4 mL) and TEA (1.0 mL, 7.17 mmol) were placed into a 10 mL round bottom flask. The mixture was stirred under N₂ at 45° C. for 3 h. The solvent was evaporated, the residue was purified by column chromatography (hexane/EtOAc; 3:1) and then by preparative TLC (CH₂Cl₂/EtOAc; 30:1). The product was obtained as a colorless wax (2.5 mg; 10%).

¹H NMR (500 MHz, CDCl₃) δ 9.02 (s, 1H), 8.94 (s, 1H), 8.87 (s, 1H), 8.30 (s, 1H), 8.09 (dd, J=8.5, 1.6 Hz, 1H), 8.00-7.93 (m, 2H), 7.91-7.85 (m, 2H), 7.57-7.50 (m, 3H).

$^{13}$C NMR (126 MHz, CDCl$_3$) δ 155.2, 148.5, 146.5, 146.1, 145.1, 133.8, 133.1, 128.5, 128.5, 127.9, 127.7, 126.6, 126.4, 126.3, 124.8, 122.8, 121.6, 119.5, 116.9.

HRMS (APCI): calcd. for C$_{20}$H$_{12}$N$_2$O$_2$ [M+]$^+$=313.0972; found [M+H]$^+$=313.0975.

Preparative Example 63

By essentially same procedure set forth in Preparative Example 61, using [1,1'-biphenyl]-4-ylboronic acid instead of [1,1'-biphenyl]-3-ylboronic acid, the compound given below was prepared.

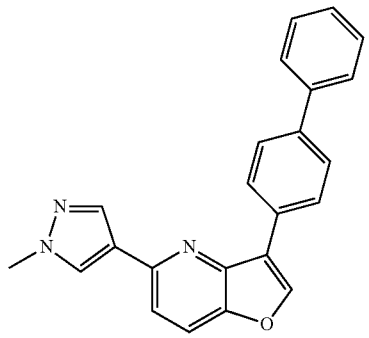 [SMILES: Cn1cc(-c2ccc3occ(-c4ccc(-c5ccccc5)cc4)c3n2)cn1]

White solid.
$^1$H NMR (500 MHz, CDCl$_3$) δ 8.28-8.24 (m, 2H), 8.16 (s, 1H), 8.04 (d, J=2.9 Hz, 2H), 7.77 (d, J=8.6 Hz, 1H), 7.76-7.72 (m, 2H), 7.70-7.66 (m, 2H), 7.50-7.45 (m, 3H), 7.40-7.35 (m, 1H), 4.00 (s, 3H).
$^{13}$C NMR (126 MHz, CDCl$_3$) δ 148.8, 147.6, 145.8, 145.1, 141.0, 140.5, 137.7, 129.9, 129.0, 128.9, 127.6, 127.5, 127.4, 127.1, 124.3, 121.3, 119.2, 115.8, 39.3.

HRMS (APCI): calcd. for C$_{23}$H$_{17}$N$_3$O [M+H]$^+$= 352.1441; found [M+H]$^+$=352.1442.

Preparative Example 64

By essentially same procedure set forth in Preparative Example 61, using [1,1'-biphenyl]-2-ylboronic acid instead of [1,1'-biphenyl]-3-ylboronic acid, the compound given below was prepared.

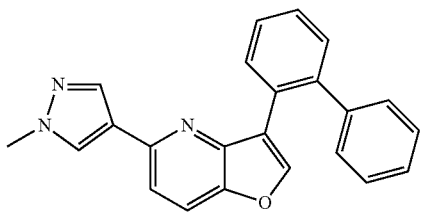 [SMILES: Cn1cc(-c2ccc3occ(-c4ccccc4-c4ccccc4)c3n2)cn1]

Colorless wax.
$^1$H NMR (500 MHz, CDCl$_3$) δ 8.18 (d, J=7.6 Hz, 1H), 7.98-7.91 (m, 2H), 7.67 (d, J=8.6 Hz, 1H), 7.54-7.48 (m, 1H), 7.47-7.42 (m, 2H), 7.38 (d, J=8.6 Hz, 1H), 7.35-7.30 (m, 2H), 7.30-7.22 (m, 3H), 7.17 (s, 1H), 3.97 (s, 3H).
$^{13}$C NMR (126 MHz, CDCl$_3$) δ 148.5, 147.5, 146.6, 146.1, 142.2, 141.6, 137.7, 130.9, 130.6, 129.5, 129.1, 128.6, 128.3, 127.8, 127.6, 127.1, 124.1, 120.8, 119.0, 115.5, 39.3.

HRMS (APCI): calcd. for C$_{23}$H$_{17}$N$_3$O [M+H]$^+$= 352.1444; found [M+H]$^+$=352.1448.

Preparative Example 65

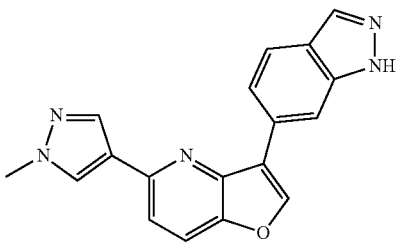 [SMILES: Cn1cc(-c2ccc3occ(-c4ccc5cn[nH]c5c4)c3n2)cn1]

Degassed 1-BuOH (2.5 mL) and H$_2$O (0.5 mL) were placed into a 10 mL round bottom flask, then the product from Preparative Example 58 (40 mg, 144 μmol), 6-(4,4,5,5-tetramethyl-1,3,2-dioxaborolan-2-yl)-1H-indazole (49.2 mg, 0.201 mmol), Pd(PPh$_3$)$_4$ (8.3 mg, 7.2 μmol) and K$_3$PO$_4$ (92 mg, 0.432 mmol) were added. The mixture was stirred under N$_2$ at 90° C. for 18 h. The solvent was evaporated and the residue was purified by column chromatography on silica gel (MeOH/EtOAc; 1:10) and then by preparative TLC (CH$_2$Cl$_2$/acetone; 3:2). The product was obtained as a white solid (10 mg; 22%).

$^1$H NMR (500 MHz, acetone-d6) δ 12.35 (b, 1H), 9.06 (d, J=1.0 Hz, 1H), 8.66 (s, 1H), 8.27 (s, 1H), 8.14 (s, 1H), 8.06 (d, J=0.9 Hz, 1H), 7.95 (d, J=8.7 Hz, 1H), 7.89-7.84 (m, 2H), 7.68 (d, J=8.6 Hz, 1H), 3.98 (s, 3H).
$^{13}$C NMR (126 MHz, acetone-d6) δ 150.2, 148.5, 147.3, 146.5, 142.0, 138.4, 134.8, 129.9, 129.9, 124.9, 123.6, 122.0, 121.6, 120.5, 120.3, 116.8, 109.7, 39.4.

HRMS (APCI): calcd. for C$_{18}$H$_{12}$N$_5$O [M+H]$^+$= 316.1193; found [M+H]$^+$=316.1197.

Preparative Example 66

Degased 1-butanol (2.0 mL) and H$_2$O (0.4 mL) were placed into a 5 mL round bottom flask. Then, the product from Preparative Example 58 (30 mg, 108 μmol), (4-carbamoylphenyl)boronic acid (26.7 mg, 0.162 mmol), Pd(PPh$_3$)$_4$ (6.2 mg, 5.4 μmol) and K$_3$PO$_4$ (68.6 mg, 0.323 mmol) were added. The mixture was stirred under N$_2$ at 80° C. for 45 mm. The solvent was evaporated and the residue was purified by column chromatography on silica gel (MeOH/EtOAc; 1:10) and then by preparative TLC (MeOH/EtOAc; 1:10). The product was obtained as a white solid (12 mg; 35%).

$^1$H NMR (500 MHz, acetone-d6) δ 8.68 (s, 1H), 8.50-8.45 (m, 2H), 8.28 (s, 1H), 8.10-8.05 (m, 3H), 7.95 (d, J=8.7 Hz, 1H), 7.69 (d, J=8.7 Hz, 1H), 3.97 (s, 3H).

$^{13}$C NMR (126 MHz, acetone-d6) δ 168.8, 150.5, 148.5, 147.8, 146.2, 138.2, 135.1, 134.3, 130.0, 128.9, 127.6, 124.8, 121.3, 120.4, 116.9, 39.4.

HRMS (APCI): calcd. for $C_{18}H_{14}N_4O_2$ [M+H]$^+$= 319.1190; found [M+H]$^+$=319.1187.

Preparative Example 67

By essentially same procedure set forth in Preparative Example 66, using (3-chloro-4-methoxyphenyl)boronic acid instead of (4-carbamoylphenyl)boronic acid, the compound given below was prepared.

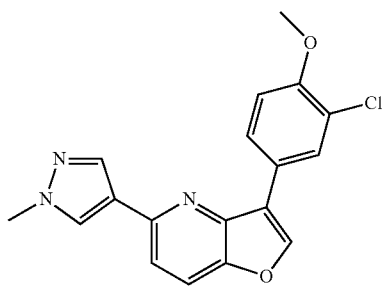 [SMILES: COc1ccc(-c2coc3ccc(-c4cnn(C)c4)nc23)cc1Cl]

White solid.

$^1$H NMR (500 MHz, acetone-d6) δ 8.56 (s, 1H), 8.43 (d, J=2.1 Hz, 1H), 8.34 (dd, J=8.6, 2.2 Hz, 1H), 8.22 (s, 1H), 8.07 (d, J=0.6 Hz, 1H), 7.92 (d, J=8.7 Hz, 1H), 7.66 (d, J=8.7 Hz, 1H), 7.25 (d, J=8.6 Hz, 1H), 3.97 (d, J=2.0 Hz, 6H).

$^{13}$C NMR (126 MHz, acetone-d6) δ 155.5, 150.2, 148.3, 146.5, 146.2, 138.2, 129.8, 129.3, 127.6, 125.6, 124.8, 123.1, 120.4, 120.3, 116.8, 113.7, 56.7, 39.4.

HRMS (APCI): calcd. for $C_{18}H_{14}ClN_3O_2$ [M+H]$^+$= 340.0847; found [M+H]$^+$=340.0842.

Preparative Example 68

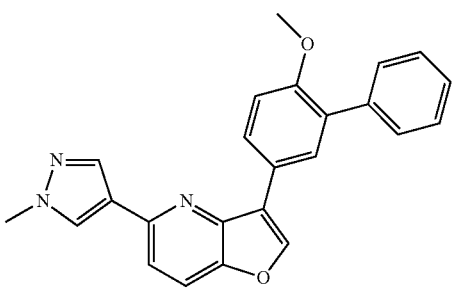 [SMILES: COc1ccc(-c2coc3ccc(-c4cnn(C)c4)nc23)cc1-c1ccccc1]

Degassed 1-butanol (2.0 mL) and H$_2$O (0.4 mL) were placed into a 10 mL round bottom flask. Then, the product from Preparative Example 67 (25 mg, 0.074 mmol), phenylboronic acid (11.7 mg, 95.7 μmol), Pd(OAc)$_2$ (1.0 mg, 3.7 μmol), SPhos (1.8 mg, 44 μmol) and K$_3$PO$_4$ (46.9 mg, 0.220 mmol) were added. The mixture was stirred under N$_2$ at 80° C. for 4 h. The solvent was evaporated and the residue was purified by column chromatography on silica gel (EtOAc) and then by preparative TLC (CH$_2$Cl$_2$/EtOAc; 2:1; 3 runs). The product was obtained as a colorless wax (9 mg; 32%).

$^1$H NMR (300 MHz, acetone-d6) δ 8.56 (s, 1H), 8.43-8.33 (m, 2H), 8.19 (s, 1H), 8.05 (d, J=0.6 Hz, 1H), 7.90 (d, J=8.7 Hz, 1H), 7.70-7.61 (m, 3H), 7.50-7.33 (m, 3H), 7.24 (d, J=8.5 Hz, 1H), 3.96 (s, 3H), 3.89 (s, 3H).

$^{13}$C NMR (75 MHz, acetone-d6) δ 157.2, 150.0, 148.4, 146.6, 146.2, 139.9, 138.2, 131.7, 130.6, 130.4, 129.8, 129.0, 128.3, 127.9, 125.0, 124.8, 121.5, 120.1, 116.6, 112.9, 56.2, 39.4.

HRMS (APCI): calcd. for $C_{24}H_{19}N_3O_2$ [M+H]$^+$= 382.1550; found [M+H]$^+$=382.1547.

Preparative Example 69

By essentially same procedure set forth in Preparative Example 66, using (4-formylphenyl)boronic acid MIDA ester instead of (4-carbamoylphenyl)boronic acid, the compound given below was prepared.

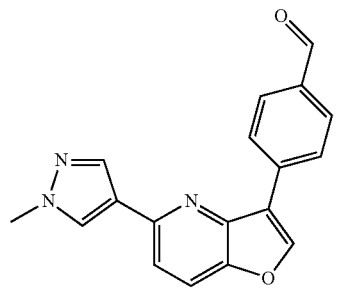 [SMILES: Cn1cc(-c2ccc3occ(-c4ccc(C=O)cc4)c3n2)cn1]

White solid.

$^1$H NMR (500 MHz, acetone-d6) δ 10.11 (s, 1H), 8.78 (s, 1H), 8.65 (d, J=8.3 Hz, 2H), 8.32 (s, 1H), 8.11 (s, 1H), 8.09-8.04 (m, 2H), 7.99 (d, J=8.7 Hz, 1H), 7.73 (d, J=8.7 Hz, 1H), 3.99 (s, 3H).

$^{13}$C NMR (126 MHz, acetone-d6) δ 192.6, 192.5, 150.7, 148.6, 148.6, 146.0, 138.3, 136.7, 130.9, 130.1, 128.2, 124.7, 121.0, 120.5, 117.1, 39.4.

HRMS (APCI): calcd. for $C_{18}H_{13}N_3O_2$ [M+H]$^+$= 304.1081; found [M+H]$^+$=304.1079.

Preparative Example 70

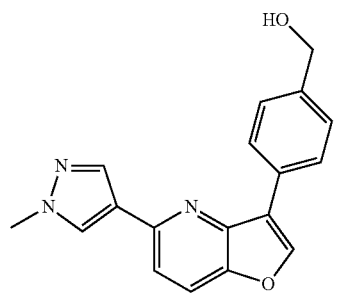 [SMILES: Cn1cc(-c2ccc3occ(-c4ccc(CO)cc4)c3n2)cn1]

The product from Preparative Example 69 (31 mg, 0.102 mmol), NaBH$_4$ (8 mg, 0.204 mmol) and MeOH (7 mL) were placed into a 10 mL round bottom flask. The mixture was stirred under N$_2$ at 25° C. for 90 min. Aqueous saturated solution of NH$_4$Cl (10 mL) was added and the mixture was extracted with EtOAc (2×20 mL). The organic phase was washed with brine (10 mL), dried over MgSO$_4$ and filtered. The solvent was evaporated and the residue was purified by column chromatography on silica gel (MeOH/EtOAc; 1:12). The product was obtained as a white solid (26 mg; 84%).

$^1$H NMR (500 MHz, acetone-d6) δ 8.54 (s, 1H), 8.33-8.29 (m, 2H), 8.25 (s, 1H), 8.06 (d, J=0.6 Hz, 1H), 7.92 (d, J=8.7 Hz, 1H), 7.66 (d, J=8.7 Hz, 1H), 7.52-7.47 (m, 2H), 4.72-4.68 (m, 2H), 3.96 (s, 3H).

$^{13}$C NMR (126 MHz, acetone-d6) δ 150.2, 148.4, 146.7, 146.5, 142.9, 138.2, 130.6, 129.9, 127.8, 127.8, 124.9, 122.0, 120.2, 116.7, 64.7, 39.4.

HRMS (APCI): calcd. for $C_{18}H_{15}N_3O_2$ [M+H]$^+$= 306.1237; found [M+H]$^+$=306.1242.

Preparative Example 71

By essentially same procedure set forth in Preparative Example 66, using (4-(methylsulfonyl)phenyl)boronic acid instead of (4-carbamoylphenyl)boronic acid, the compound given below was prepared.

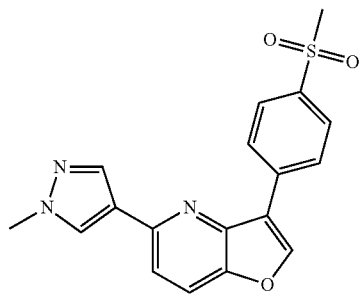 [SMILES: Cn1cc(-c2ccc3occ(-c4ccc(S(C)(=O)=O)cc4)c3n2)cn1]

White solid.

$^1$H NMR (300 MHz, acetone-d6) δ 8.78 (s, 1H), 8.70-8.63 (m, 2H), 8.31 (s, 1H), 8.12-8.02 (m, 3H), 7.98 (d, J=8.7 Hz, 1H), 7.71 (d, J=8.7 Hz, 1H), 3.97 (s, 3H), 3.17 (s, 3H).

$^{13}$C NMR (75 MHz, acetone-d6) δ 150.7, 148.7, 148.5, 145.9, 141.0, 138.2, 137.4, 130.1, 128.7, 128.3, 124.6, 120.6, 120.4, 117.1, 44.6, 39.4.

HRMS (APCI): calcd. for $C_{18}H_{15}N_3O_3S$ [M+H]$^+$= 354.0907; found [M+H]$^+$=354.0901.

Preparative Example 72

By essentially same procedure set forth in Preparative Example 66, using (4-(methylthio)phenyl)boronic acid instead of (4-carbamoylphenyl)boronic acid, the compound given below was prepared.

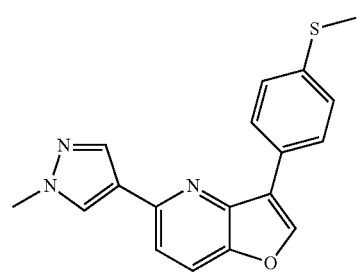

White solid.

$^1$H NMR (500 MHz, acetone-d6) δ 8.55 (s, 1H), 8.35-8.29 (m, 2H), 8.24 (s, 1H), 8.06 (d, J=0.5 Hz, 1H), 7.91 (d, J=8.7 Hz, 1H), 7.65 (d, J=8.6 Hz, 1H), 7.43-7.38 (m, 2H), 3.96 (s, 3H), 2.55 (s, 3H).

$^{13}$C NMR (126 MHz, acetone-d6) δ 150.2, 148.4, 146.7, 146.4, 139.0, 138.2, 129.9, 128.8, 128.3, 127.5, 124.9, 121.5, 120.2, 116.7, 39.4, 15.7.

HRMS (ACPI): calcd. for $C_{18}H_{25}N_3OS$ [M+H]$^+$= 322.1009; found [M+H]$^+$=322.1003.

Preparative Example 73

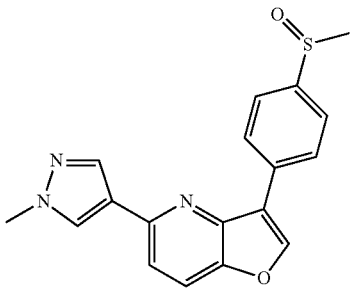

The product from Preparative Example 72 (13 mg, 40.4 μmol) and CH$_2$Cl$_2$ (2 mL) were placed into a 5 mL round bottom flask. The mixture was cooled to 0° C., then mCPBA (7.0 mg, 40.4 mmol) was added and the mixture was stirred under N$_2$ at 0° C. for 45 min. Aqueous saturated solution of NaHCO$_3$ (5 mL) and H$_2$O (5 mL) were added and the mixture was extracted with CH$_2$Cl$_2$ (2×10 mL). The organic phase was dried over MgSO$_4$ and filtered. The solvent was evaporated and the residue was purified by preparative TLC on silica gel (EtOAc/MeOH; 20:1). The product was obtained as a yellow wax (5 mg; 38%).

$^1$H NMR (300 MHz, acetone-d6) δ 8.70 (s, 1H), 8.63-8.55 (m, 2H), 8.29 (s, 1H), 8.09 (s, 1H), 7.96 (d, J=8.7 Hz, 1H), 7.81 (d, J=8.6 Hz, 2H), 7.69 (d, J=8.7 Hz, 1H), 3.97 (s, 3H), 2.76 (s, 3H).

$^{13}$C NMR (75 MHz, acetone-d6) δ 150.4, 148.4, 147.8, 147.1, 146.1, 138.2, 134.6, 130.0, 128.4, 124.8, 124.7, 120.9, 120.4, 116.9, 44.4, 39.3.

HRMS (APCI): calcd. for $C_{18}H_{15}N_3O_3S$ [M+H]$^+$= 338.0958; found [M+H]$^+$=338.0955.

Preparative Example 74

By essentially same procedure set forth in Preparative Example 66, using (3-(tert-butyl)phenyl)boronic acid instead of (4-carbamoylphenyl)boronic acid, the compound given below was prepared.

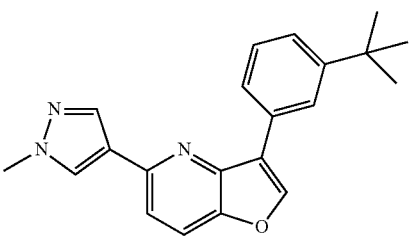 [SMILES: Cn1cc(-c2ccc3occ(-c4cccc(C(C)(C)C)c4)c3n2)cn1]

Colorless wax.

$^1$H NMR (500 MHz, CDCl$_3$) δ 8.41 (d, J=0.9 Hz, 1H), 8.12 (s, 1H), 8.04 (s, 1H), 7.97 (s, 1H), 7.84 (m, 1H), 7.74 (d, J=8.6 Hz, 1H), 7.42 (m, 3H), 3.97 (s, 3H), 1.44 (s, 9H).

$^{13}$C NMR (126 MHz, CDCl$_3$) δ 151.7, 148.6, 147.6, 145.9, 145.0, 137.7, 130.4, 128.8, 128.5, 124.8, 124.7, 124.4, 124.1, 122.0, 119.1, 115.6, 35.0, 31.6, 31.0.

HRMS (APCI): calcd. for $C_{21}H_{21}N_3O$ [M+H]$^+$= 332.1757; found [M+H]$^+$=332.1754.

Preparative Example 75

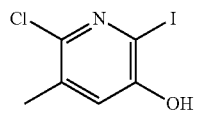

6-chloro-5-methylpyridin-3-ol (2.51 g, 17.5 mmol), iodine (4.44 g, 17.5 mmol), H$_2$O (35 mL), THF (30 mL) and Na$_2$CO$_3$ (3.90 g, 36.8 mmol) were placed into a 100 mL round bottom flask. The mixture was stirred under N$_2$ at 25° C. for 18 h. The solvent was evaporated and the solution was neutralized with 1M aqueous solution of HCl (38 mL). Then, saturated aqueous solution of NH$_4$Cl (30 mL) and H$_2$O (100 mL) were added and the mixture was extracted with CH$_2$Cl$_2$ (80 mL) and EtOAc (2×80 mL). The organic phase was washed with brine (30 mL), dried over MgSO$_4$, filtered, and the solvent was evaporated. The product was obtained as a white solid (4.24 g; 90%).

$^1$H NMR (500 MHz, CDCl$_3$) δ 7.12 (d, J=0.7 Hz, 1H), 2.31 (d, J=0.7 Hz, 3H).

$^{13}$C NMR (126 MHz, CDCl$_3$) δ 124.8, 19.3.

HRMS (APCI): calcd. for $C_6H_5ClINO$ [M+H]$^+$= 269.9178; found [M+H]$^+$=269.9179.

Preparative Example 76

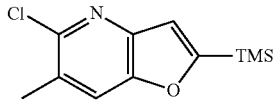

The product from Preparative Example 75 (2.2 g, 8.16 mmol), degassed 1,4-dioxane (17 mL) and TEA (17 mL) were placed into a 100 mL round bottom flask. Then, ethynyltrimethylsilane (1.49 mL, 10.6 mmol), CuI (78 mg, 0.408 mmol) and PdCl$_2$(PPh$_3$)$_2$ (114 mg, 0.163 mmol) were added. The mixture was stirred under N$_2$ at 45° C. for 3 h. The solvent was evaporated and the residue was purified by column chromatography on silica gel (hexane/EtOAc; 10:1). The product was obtained as an orange solid (930 mg, 47%).

$^1$H NMR (500 MHz, CDCl$_3$) δ 7.62 (s, 1H), 7.01 (d, J=0.8 Hz, 1H), 2.48 (s, 3H), 0.36 (s, 9H).

$^{13}$C NMR (126 MHz, CDCl$_3$) δ 169.5, 150.4, 147.1, 146.1, 127.3, 121.1, 116.5, 20.6, −1.9.

HRMS (APCI): calcd. for $C_{11}H_{14}ClNOSi$ [M+H]$^+$= 240.0606; found [M+H]$^+$=240.0604.

Preparative Example 77

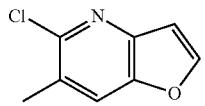

The product from Preparative Example 76 (0.90 g, 3.75 mmol), MeOH (28 mL) and KF (654 mg, 11.3 mmol) were placed into a 100 mL round bottom flask. The mixture was stirred under N$_2$ at 25° C. for 14 h, then at 60° C. for additional 8 h. The solvent was evaporated and the residue was purified by column chromatography on silica gel (hexane/EtOAc; from 10:1 to 5:1). The product was obtained as a white solid (560 mg, 88%).

$^1$H NMR (500 MHz, CDCl$_3$) δ 7.79 (d, J=2.0 Hz, 1H), 7.65 (s, 1H), 6.89 (m, 1H), 2.49 (s, 3H).

$^{13}$C NMR (126 MHz, CDCl$_3$) δ 149.3, 147.6, 147.4, 145.3, 127.8, 121.4, 107.7, 20.6.

HRMS (APCI): calcd. for $C_8H_6ClNO$ [M+H]$^+$=168.0211; found [M+H]$^+$=168.0209.

Preparative Example 78

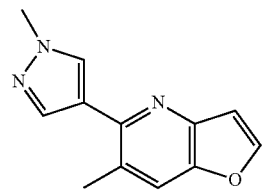 [SMILES: Cc1cc2occc2nc1-c1cnn(C)c1]

Degassed 1,2-dimethoxyethane (4.0 mL) and H$_2$O (1.0 mL) were placed into a 25 mL round bottom flask. Then, the product from Preparative Example 77 (160 mg, 0.94 mmol), 1-methyl-4-(4,4,5,5-tetramethyl-1,3,2-dioxaborolan-2-yl)-1H-pyrazole (294 mg, 1.42 mmol), PdCl$_2$(dppf) (34 mg, 47 µmol) and K$_3$PO$_4$ (599 mg, 2.82 mmol) were added. The mixture was stirred under N$_2$ at 80° C. for 5 h. The solvent was evaporated and the residue was purified by column chromatography on silica gel (EtOAc/MeOH; from 1:0 to 10:1) and then by another column chromatography (EtOAc). The product was obtained as a white solid (120 mg; 60%).

$^1$H NMR (500 MHz, CDCl$_3$) δ 7.90 (s, 1H), 7.82 (s, 1H), 7.76 (d, J=2.3 Hz, 1H), 7.60 (s, 1H), 6.92 (dd, J=2.2, 0.9 Hz, 1H), 3.97 (s, 3H), 2.56 (s, 3H).

$^{13}$C NMR (126 MHz, CDCl$_3$) δ 148.6, 146.9, 145.3, 139.3, 137.0, 130.3, 126.6, 123.2, 120.4, 108.0, 39.1, 21.6.

HRMS (APCI): calcd. for $C_{12}H_{11}N_3O$ [M+H]$^+$= 214.0975; found [M+H]$^+$=214.0972.

Preparative Example 79

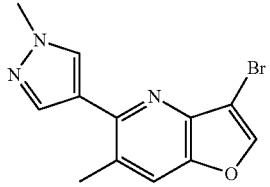 [SMILES: Cc1cc2occ(Br)c2nc1-c1cnn(C)c1]

The product from Preparative Example 78 (115 mg, 0.54 mmol) and CCl$_4$ (5 mL) were placed into a 100 mL round bottom flask. The mixture was cooled to −18° C., then bromine (0.56 mL, 10.8 mmol) was added slowly. The mixture was allowed to warm to 12° C. and stirred under N$_2$ for 60 mm. The mixture was poured into a mixture of water (30 mL), ice (20 mL) and Na$_2$S$_2$O$_5$ (2 g). The resulting mixture was extracted with CH$_2$Cl$_2$ (20 mL) and EtOAc (2×15 mL). The organic phase was dried over MgSO$_4$, filtered, and the solvent was evaporated. Toluene (12 mL)

and DBU (0.241 mL, 1.62 mmol) were added to the residue and the mixture was stirred under $N_2$ at 80° C. for 45 min. The solvent was evaporated and the residue was purified by column chromatography on silica gel (EtOAc/hexane; 1:1) and then by preparative TLC (EtOAc/hexane; 2:1). The product was obtained as a white solid (19 mg, 12%).

$^1$H NMR (500 MHz, CDCl$_3$) δ 7.93 (d, J=2.3 Hz, 2H), 7.80 (s, 1H), 7.61 (s, 1H), 3.98 (s, 3H), 2.60 (s, 3H).

$^{13}$C NMR (126 MHz, CDCl$_3$) δ 149.2, 146.5, 146.1, 142.5, 139.3, 130.9, 127.9, 122.98 (s), 121.0, 99.5, 39.2, 21.7.

HRMS (APCI): calcd. for $C_{12}H_{10}BrN_3O$ [M+H]$^+$= 292.0080; found [M+H]$^+$=292.0075.

Preparative Example 80

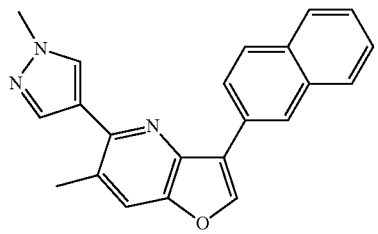 [SMILES: Cc1cc2occ(-c3ccc4ccccc4c3)c2nc1-c1cnn(C)c1]

Degassed 1-butanol (2.0 mL) and $H_2O$ (0.4 mL) were placed into a 10 mL round bottom flask. Then, the product from Preparative Example 79 (15 mg, 51.3 μmol), naphthalen-2-ylboronic acid (13.3 mg, 77 μmol), Pd(PPh$_3$)$_4$ (3.0 mg, 2.6 μmol) and K$_3$PO$_4$ (32.7 mg, 0.154 mmol) were added. The mixture was stirred under $N_2$ at 80° C. for 70 mm. The solvent was evaporated and the residue was purified by column chromatography on silica gel (EtOAc/CH$_2$Cl$_2$; 1:2) and then by preparative TLC (EtOAc/CH$_2$Cl$_2$; 2:3). The product was obtained as a colorless wax (8.5 mg; 49% yield).

$^1$H NMR (300 MHz, CDCl$_3$) δ 8.88 (s, 1H), 8.18 (s, 1H), 8.14-8.07 (m, 2H), 7.97-7.84 (m, 4H), 7.64 (d, J=0.5 Hz, 1H), 7.55-7.44 (m, 2H), 4.03 (s, 3H), 2.64 (s, 3H).

$^{13}$C NMR (75 MHz, CDCl$_3$) δ 148.1, 148.0, 144.9, 143.9, 139.8, 133.9, 133.0, 130.5, 128.6, 128.5, 128.4, 127.9, 126.5, 126.4, 126.3, 126.1, 125.0, 123.9, 121.4, 120.7, 39.3, 21.9.

HRMS (APCI): calcd. for $C_{22}H_{17}N_3O$ [M+H]$^+$= 340.1444; found [M+H]$^+$=340.1440.

Preparative Example 81

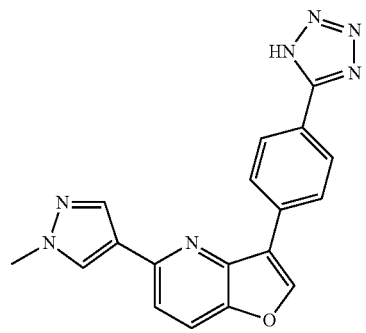 [SMILES: Cn1cc(-c2ccc3occ(-c4ccc(-c5nnn[nH]5)cc4)c3n2)cn1]

Degassed 1-butanol (2.0 mL) and $H_2O$ (0.4 mL) were placed into a 10 mL round bottom flask. Then, the product from Preparative Example 58 (23.8 mg, 85.6 μmol), (4-(1H-tetrazol-5-yl)phenyl)boronic acid (19.5 mg, 0.103 mmol), Pd(PPh$_3$)$_4$ (5.0 mg, 4.3 μmol) and K$_3$PO$_4$ (54.5 mg, 0.257 mmol) were added. The mixture was refluxed under $N_2$ for 150 min. The solvent was evaporated and the residue purified by column chromatography on silica gel (EtOAc/MeOH; from 3:1 to 2:1) and then by preparative TLC (THF/MeOH; 2:1). The product was obtained as a colorless semi-solid (12 mg; 41%).

$^1$H NMR (300 MHz, CD$_3$OD) δ 8.44 (s, 1H), 8.37-8.30 (m, 2H), 8.20-8.13 (m, 3H), 8.05 (d, J=0.7 Hz, 1H), 7.83 (d, J=8.7 Hz, 1H), 7.57 (d, J=8.7 Hz, 1H), 3.96 (s, 3H).

$^{13}$C NMR (75 MHz, CD$_3$OD) δ 149.9, 148.9, 147.3, 146.6, 138.4, 132.7, 130.7, 130.0, 128.2, 127.9, 126.5, 125.4, 122.0, 120.3, 116.9, 39.1.

HRMS (APCI): calcd. for $C_{18}H_{13}N_7O$ [M+H]$^+$= 344.1254; found [M+H]$^+$=344.1252.

ASSAYS

In vitro essays were performed by the company Merck Millipore in their KinaseProfiler radiometric protein kinase assay as paid commercial service. The compounds IC$_{50}$ values for inhibition of individual protein kinases were determined. Dose-response curves were plotted from inhibition data generated, each in duplicate, from 10 point serial dilutions of inhibitory compounds. Concentration of compound was plotted against % kinase activity. To generate IC$_{50}$ values, the dose-response curves were fitted to a standard sigmoidal curve and IC$_{50}$ values were derived by standard nonlinear regression analysis.

All tested compounds were prepared in 100% DMSO to final assay concentrations either 0.5 mM (for the concentration row A, see below) or 0.05 mM (for the concentration row B). This working stock of the compound was added to the assay well as the first component in the reaction, followed by the remaining components as detailed below. The stock solution was added to the individual assay wells in such amounts that the concentrations of the compound were either in the row A (0.001 μM, 0.003 μM, 0.01 μM, 0.03 μM, 0.1 μM, 0.3 μM, 1.0 μM, 3.0 μM, and 10.0 μM) or in the row B (0.0001 μM, 0.0003 μM, 0.001 μM, 0.003 μM, 0.01 μM, 0.03 μM, 0.1 μM, 0.3 μM, and 1.0 μM). There was no pre-incubation step between the compound and the kinase prior to initiation of the reaction.

The positive control wells contained all components of the reaction, except the compound of interest; however, DMSO (at a final concentration of 2%) was included in these wells to control for solvent effects. The blank wells contained all components of the reaction, with staurosporine as a reference inhibitor replacing the compound of interest. This abolished kinase activity and established the base-line (0% kinase activity remaining).

CLK2 Assay

CLK2 (h) was diluted in the buffer (20 mM MOPS (3-(N-morpholino)propanesulfonic acid), 1 mM EDTA (ethylendiaminotetraacetic acid), 0.01% Brij-35 (detergent), 5% Glycerol, 0.1% β-mercaptoethanol, 1 mg/mL BSAs) to the concentration of 1.01 mg/mL prior to addition to the reaction mix.

The above stock solution of CLK2(h) was added to a mixture containing 8 mM MOPS pH 7.0, 0.2 mM EDTA, and 20 μM YRRAAVPPSPSLSRHSSPHQS(p) EDEEE in such amount that the resulting concentration of CLK2(h) was 2.1 nM. This mixture was added to the stock solution of the tested compound. The reaction was initiated by the addition of the MgATP mix in such amount that the resulting concentration of Mg acetate in the reaction mixture was 10 mM and [γ-$^{33}$P-ATP] (specific activity approx. 500 cpm/pmol) was 15 μM. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

CLK4 Assay

CLK4 (h) was diluted in the buffer (20 mM MOPS, 1 mM EDTA, 0.01% Brij-35, 5% Glycerol, 0.1% β-mercaptoethanol, 1 mg/mL BSAs) to the concentration of 1.01 mg/mL prior to addition to the reaction mix.

The above stock solution of CLK4(h) was added to a mixture containing 8 mM MOPS pH 7.0, 0.2 mM EDTA, and 200 μM YRRAAVPPSPSLSRHSSPHQS(p) EDEEE in such amount that the resulting concentration of CLK4(h) was 140.8 nM. This mixture was added to the stock solution of the tested compound. The reaction was initiated by the addition of the MgATP mix in such amount that the resulting concentration of Mg acetate in the reaction mixture was 10 mM and [γ-$^{33}$P-ATP] (specific activity approx. 500 cpm/pmol) was 15 μM. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

HIPK1 Assay

HIPK1(h) was diluted in the buffer (20 mM MOPS, 1 mM EDTA, 0.01% Brij-35, 5% Glycerol, 0.1% β-mercaptoethanol, 1 mg/mL BSAs) to the concentration of 1.01 mg/mL prior to addition to the reaction mix.

The above stock solution of HIPK1(h) was added to a mixture containing 8 mM MOPS pH 7.0, 0.2 mM EDTA, and 0.33 mg/mL myelin basic protein in such amount that the resulting concentration of HIPK1(h) was 4.7 nM. This mixture was added to the stock solution of the tested compound. The reaction was initiated by the addition of the MgATP mix in such amount that the resulting concentration of Mg acetate in the reaction mixture was 10 mM and [γ-$^{33}$P-ATP] (specific activity approx. 500 cpm/pmol) was 45 μM. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

HIPK2 Assay

HIPK2(h) was diluted in the buffer (20 mM MOPS, 1 mM EDTA, 0.01% Brij-35, 5% Glycerol, 0.1% β-mercaptoethanol, 1 mg/mL BSAs) to the concentration of 1.01 mg/mL prior to addition to the reaction mix.

The above stock solution of HIPK2(h) was added to a mixture containing 8 mM MOPS pH 7.0, 0.2 mM EDTA, and 0.33 mg/mL myelin basic protein in such amount that the resulting concentration of HIPK2(h) was 1.4 nM. This mixture was added to the stock solution of the tested compound. The reaction was initiated by the addition of the MgATP mix in such amount that the resulting concentration of Mg acetate in the reaction mixture was 10 mM and [γ-$^{33}$P-ATP] (specific activity approx. 500 cpm/pmol) was 10 μM. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

HIPK3 Assay

HIPK3(h) was diluted in the buffer (20 mM MOPS, 1 mM EDTA, 0.01% Brij-35, 5% Glycerol, 0.1% β-mercaptoethanol, 1 mg/mL BSAs) to the concentration of 1.01 mg/mL prior to addition to the reaction mix.

The above stock solution of HIPK3(h) was added to a mixture containing 8 mM MOPS pH 7.0, 0.2 mM EDTA, and 1.0 mg/mL myelin basic protein in such amount that the resulting concentration of HIPK3(h) was 6.4 nM. This mixture was added to the stock solution of the tested compound. The reaction was initiated by the addition of the MgATP mix in such amount that the resulting concentration of Mg acetate in the reaction mixture was 10 mM and [γ-$^{33}$P-ATP] (specific activity approx. 500 cpm/pmol) was 15 μM. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

FLT3 Assay

FLT3(h) was diluted in the buffer (20 mM MOPS, 1 mM EDTA, 0.01% Brij-35, 5% Glycerol, 0.1% β-mercaptoethanol, 1 mg/mL BSAs) to the concentration of 1.01 mg/mL prior to addition to the reaction mix.

The above stock solution of Flt3(h) was added to a mixture containing 8 mM MOPS pH 7.0, 0.2 mM EDTA, and 50 μM EAIYAAPFAKKK, in such amount that the resulting concentration of FLT3(h) was 28.3 nM. This mixture was added to the stock solution of the tested compound. The reaction was initiated by the addition of the MgATP mix in such amount that the resulting concentration of Mg acetate in the reaction mixture was 10 mM and [γ-$^{33}$P-ATP] (specific activity approx. 500 cpm/pmol) was 200 μM. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

TRKA Assay

TRKA(h) was diluted in the buffer (20 mM MOPS, 1 mM EDTA, 0.01% Brij-35, 5% Glycerol, 0.1% β-mercaptoethanol, 1 mg/mL BSAs) to the concentration of 1.01 mg/mL prior to addition to the reaction mix.

The above stock solution of TRKA(h) was added to a mixture containing 8 mM MOPS pH 7.0, 0.2 mM EDTA, and 250 μM KKKSPGEYVNIEFG, in such amount that the resulting concentration of TRKA(h) was 28.2 nM. This mixture was added to the stock solution of the tested compound. The reaction was initiated by the addition of the MgATP mix in such amount that the resulting concentration of Mg acetate in the reaction mixture was 10 mM and [γ-$^{33}$P-ATP] (specific activity approx. 500 cpm/pmol) was 120 μM. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.

RESULTS

| compound | CLK2 | CLK4 | FLT3 | HIPK1 | HIPK2 | HIPK3 | DYRK2 | TRKA |
|---|---|---|---|---|---|---|---|---|
| 6A | B | A | | B | B | C | C | |
| 6D | C | B | | C | C | | | |
| 7A | A | A | | B | B | B | | |
| 7B | A | A | | A | A | A | C | |
| 7C | C | C | | | C | | | |
| 7D | C | C | | C | B | C | | |
| 7F | B | B | | B | A | | | |
| 8B | B | | B | | | | | C |
| 8C | | C | C | | | | | C |
| 8D | | | C | | | | | |
| 8E | | C | C | | | | | C |
| 9 | A | A | | A | A | B | C | |
| 12B | C | B | | | | | | |
| 17E | | | C | | | | | C |
| 23 | B | B | | | | | C | |
| 54 | C | C | | B | B | | | |
| 55 | B | B | | | | | | |
| 61 | A | A | | B | A | | C | |
| 62 | C | C | | B | B | | | |
| 65 | A | | | B | | | B | |
| 66 | B | | | B | | | C | |
| 70 | B | | | B | | | C | |
| 71 | B | | | C | | | C | |
| 73 | C | | | | | | C | |
| 74 | B | | C | | | | | |
| 80 | B | | | | | | | |
| 81 | C | | C | | | | C | |

A: $IC_{50} < 0.100\ \mu M$
B: $IC_{50} < 1.00\ \mu M$
C: $IC_{50} < 5.00\ \mu M$

The invention claimed is:

1. A compound represented by general formula (I):

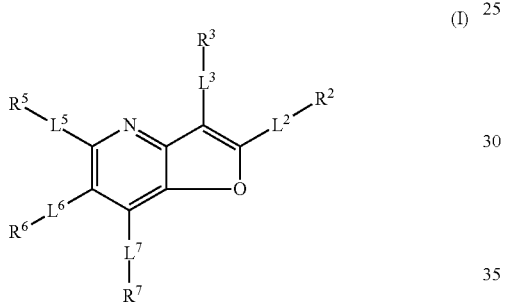

or a pharmaceutically acceptable salt, solvate or a prodrug thereof, wherein:
$L^2$ is selected from the group consisting of a bond, —O—;
$L^6$ is selected from the group consisting of a bond, —O—;
$L^7$ is selected from the group consisting of a bond, —N($R^{11}$)—;
-$L^5$-$R^5$ is heteroaryl, unsubstituted or substituted;
$R^2$ is selected from the group consisting of H; —$CF_3$; —OH; —$NH_2$; —Cl; —Br; —F; $C_1$-$C_6$ alkyl;
-$L^3$-$R^3$ is selected from the group consisting of aryl; biaryl; heterocyclylaryl; heteroarylaryl; wherein each of the substituent moieties is unsubstituted or substituted;
$R^6$ is selected from the group consisting of H; —$CF_3$; —OH; —$NH_2$; —Cl; —Br; —F; $C_1$-$C_6$ alkyl; aryl; heteroaryl; wherein each of the substituent moieties is unsubstituted or substituted;
$R^7$ is selected from the group consisting of H; $C_1$-$C_6$ alkyl; aryl; cycloalkyl; heterocyclyl; heteroaryl; biaryl; heteroarylaryl; arylheteroaryl; heterocyclylaryl; heterocyclylheteroaryl; wherein each of the substituent moieties is unsubstituted or substituted;
$R^{11}$ is selected from the group consisting of H, $C_1$-$C_6$ alkyl;
provided that the substituent in position 5 (L5-R5) is not oxadiazolyl or methyl-oxadiazolyl;
wherein:
"alkyl" means an aliphatic hydrocarbon group which may be straight or branched, whereas the alkyl is unsubstituted or substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N$(H, $C_1$-$C_4$ alkyl)$_2$, CHO, COO(H, $C_1$-$C_4$ alkyl), COH, C(O)N(H, $C_1$-$C_4$ alkyl), O(CH$_2$)$_p$N(CH$_3$)$_2$ and $NR^9R^{10}$;
"aryl" means an aromatic monocyclic or polycyclic ring system containing 6 to 14 carbon atoms, whereas the aryl is unsubstituted or substituted by one or more substituents which can be the same or different, each substituent being independently selected from the group consisting of F, Cl, Br, $CF_3$, $OCF_3$, $OR^9$, [H.K.1] $SO_2H$, $SO_2N$(H, $C_1$-$C_4$ alkyl)$_2$, CHO, COO(H, $C_1$-$C_4$ alkyl), COH, C(O)N(H, $C_1$-$C_4$ alkyl), $NR^9R^{10}$, —(CR$^9$R$^{10}$)$_p$R$^{9a}$, O(CH$_2$)$_p$N(CH$_3$)$_2$ and —(CR$^9$R$^{10}$)$_p$OR$^{9a}$;
"cycloalkyl" means an aliphatic monocyclic or bicyclic ring system comprising 3 to 10 carbon atoms, whereas the cycloalkyl is unsubstituted or substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N$(H, $C_1$-$C_4$ alkyl)$_2$, CHO, COO(H, $C_1$-$C_4$ alkyl), COH, C(O)N(H, $C_1$-$C_4$ alkyl), $NR^9R^{10}$, —(CR$^9$R$^{10}$)$_p$R$^{9a}$, O(CH$_2$)$_p$N(CH$_3$)$_2$ and —(CR$^9$R$^{10}$)$_p$OR$^{9a}$;
"heterocyclyl" means an aliphatic monocyclic or bicyclic ring system containing 3 to 10 carbon atoms, preferably 4 to 8 carbon atoms, and at least one heteroatom selected from the group consisting of nitrogen, oxygen and sulfur, whereas the heterocyclyl is unsubstituted or substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N$(H, $C_1$-$C_4$ alkyl)$_2$, CHO, COO(H, $C_1$-$C_4$ alkyl), COH, C(O)N(H, $C_1$-$C_4$ alkyl), $NR^9R^{10}$, —(CR$^9$R$^{10}$)$_p$R$^{9a}$, O(CH$_2$)$_p$N(CH$_3$)$_2$ and —(CR$^9$R$^{10}$)$_p$OR$^{9a}$;
"heteroaryl" means an aromatic monocyclic or bicyclic ring system containing 1 to 14 carbon atoms, and at least one heteroatom selected from the group consisting of nitrogen, oxygen and sulfur, whereas the heteroaryl is unsubstituted or substituted by one or more substituents which can be the same or different, each substituent being independently selected from the group consisting of F, Cl, Br, $CF_3$, $OCF_3$, $OR^9$, $SR^9$, SOH, $SO_2H$, $SO_2N(H, C_1-C_4 \text{ alkyl})_2$, CHO, COO(H, $C_1-C_4$ alkyl), COH, C(O)N(H, $C_1-C_4$ alkyl), $NR^9R^{10}$, $—(CR^9R^{10})_pR^{9a}$, $O(CH_2)_pN(CH_3)_2$ and $—(CR^9R^{10})_pOR^{9a}$;

"biaryl" means an aryl-aryl- group in which each of the aryls is independently as previously described;

"bi(heteroaryl)" means an heteroaryl-heteroaryl- group in which each of the heteroaryls is independently as previously described;

"cycloalkylaryl" means a cycloalkyl-aryl- group in which the cycloalkyl and aryl are as previously described;

"heterocyclylaryl" means a heterocyclyl-aryl- group in which the heterocyclyl and aryl are as previously described;

"heteroarylaryl" means a heteroaryl-aryl- group in which the heteroaryl and aryl are as previously described;

"arylheteroaryl" means an aryl-heteroaryl- group in which the aryl and heteroaryl are as previously described;

"cycloalkylheteroaryl" means a cycloalkyl-heteroaryl- group in which the heteroaryl and cycloalkyl are as previously described;

"heterocyclylheteroaryl" means a heterocyclyl-heteroaryl- group in which the heterocyclyl and heteroaryl are as previously described;

wherein each of aryl, cycloalkyl, heterocyclyl, heteroaryl, biaryl, bi(heteroaryl), cycloalkylaryl, heterocyclylaryl, heteroarylaryl, arylheteroaryl, cycloalkylheteroaryl, and heterocyclylheteroaryl can be bound directly or via a methylene or ethylene spacer;

p is an integer in the range of from 1 to 7;

$R^9$ is H or C1-C6 alkyl, unsubstituted or optionally substituted by —OH, —$NH_2$, —$N(CH_3)_2$;

$R^{9a}$ is H or C1-C6 alkyl, unsubstituted or optionally substituted by —OH, —$NH_2$, —$N(CH_3)_2$;

$R^{10}$ is H or C1-C6 alkyl, unsubstituted or optionally substituted by —OH, —$NH_2$, —$N(CH_3)_2$.

2. The compound of claim 1, wherein -L-$R^5$ is substituted by at least one substituent selected from the group consisting of F, Cl, Br, methyl, ethyl, propyl, isopropyl, butyl, isobutyl, tert-butyl, methoxy, ethoxy, propoxy, isopropoxy, OH, $NH_2$, $N(CH_3)_2$, $O(CH_2)_pN(CH_3)_2$.

3. The compound of any one of the preceding claims, wherein -$L^3$-$R^3$ is substituted by at least one substituent selected from the group consisting of F, Cl, Br, methyl, ethyl, propyl, isopropyl, butyl, isobutyl, tert-butyl, methoxy, ethoxy, propoxy, isopropoxy, OH, $NH_2$, $N(CH_3)_2$, $O(CH_2)_pN(CH_3)_2$.

4. The compound of claim 1, wherein the heteroaryl moiety is selected from a 5-membered or 6-membered ring, or a fused bicyclic system consisting of two 5-membered rings, two 6-membered rings or one 5-membered and one 6-membered ring, and wherein the heteroaryl moiety comprises at least one nitrogen atom and is unsubstituted or substituted.

5. The compound of claim 1, wherein the aryl moiety is selected from phenyl, naphthyl; biaryl moiety is biphenyl; heteroaryl moiety is pyrazolyl; wherein each moiety is unsubstituted or substituted.

6. The compound of claim 1, wherein -$L^2$-$R^2$, -$L^6$-$R^6$, -$L^7$-$R^7$ are hydrogens.

7. The compound of claim 1, wherein -$L^3$-$R^3$ is aryl or biaryl, unsubstituted or substituted, and -$L^5$-$R^5$ is heteroaryl, unsubstituted or substituted.

8. A pharmaceutical composition comprising at least one compound of formula (I) according to claim 1 and at least one pharmaceutically acceptable auxiliary compound.

* * * * *